US006566140B2

(12) United States Patent
Mann et al.

(10) Patent No.: US 6,566,140 B2
(45) Date of Patent: *May 20, 2003

(54) INHIBITION OF COAGULATION IN BLOOD AND BLOOD PRODUCTS

(75) Inventors: Kenneth G. Mann, Grand Isle, VT (US); Mathew D. Rand, Danvers, MA (US); Kevin M. Cawthern, Haverstraw, NY (US)

(73) Assignee: University of Vermont and State Agriculture College, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/844,209

(22) Filed: Apr. 27, 2001

(65) Prior Publication Data

US 2002/0042144 A1 Apr. 11, 2002

Related U.S. Application Data

(62) Division of application No. 09/327,806, filed on Jun. 8, 1999, now Pat. No. 6,403,381.
(60) Provisional application No. 60/088,488, filed on Jun. 8, 1998.

(51) Int. Cl.$^7$ .............................................. G01N 33/86

(52) U.S. Cl. ............................. 436/69; 436/6; 435/13; 73/64.41; 600/369

(58) Field of Search .......................... 436/63, 69, 175; 435/2, 13; 433/73; 73/64.41; 600/368, 369

(56) References Cited

U.S. PATENT DOCUMENTS

| 4,882,272 A | 11/1989 | Scott et al. ................... 435/13 |
| 5,314,826 A | 5/1994 | Baugh |
| 5,318,910 A | 6/1994 | LaDuca |
| 5,472,850 A | 12/1995 | Morrissey |
| 5,705,395 A | 1/1998 | Griffin et al. |
| 6,403,381 B1 * | 6/2002 | Mann et al. .................. 436/69 |

OTHER PUBLICATIONS

Brown. Hematology: Principles and Procedures. Third Edition, 1980, pp. 127–128.*
Rand et al. Blood Clotting in Minimally Altered Whole Blood. Blood, vol. 88, No. 9, 1996, pp. 3432–3445.*
Ewald et al. Plasma–Mediated Activation of Contact System in Repsonse to Pharmacological Thrombolysis. Circulation, vol. 91, No. 1, 1995, pp. 28–36.*
Doellgast, G.J. et al., *Clin. Chem.* 34/2:294–299 (1988).
Cornelis van't Veer et al., *J. Biol. Chem.* 14/7:4367–4377 (1997).
Cawthern, K. M., et al. "Regulation of Thrombin Generation By Tissue Factor, Factor VIIIs And Factor XIa In a Whole Blood Model", *Blood* 88:520a, Abstract 2067 (1996).
Rand, M.D. et al., *Blood* 88/9:3432–3445 (1996).

K. G. Mann, et al., "Surface–Dependent Reactions of the Vitamin K–Dependent Enzyme Compleses", Blood, vol. 76, No. 1, (1990), pp. 1–16.
M. Munakata, et al. "Evaluation of the Factor XIIa Assay Kit", Rinsho Byori, vol. 44, No. 9, (1996), pp. 883–888.
D. J. Moliterno, MD, et al. "Effect of Platelet Glycoprotein IIb/IIIa Integrin Blockade on Activated Clotting Time During Percutaneous Transluminal Coronary Angioplastyy or Directional Atherectomuy (The EPIC Trial)", The American Journal of Cardiology, vol. 75 (1995), pp. 559–562.
E. W. Davie, et al. "The Coagulation Cascade:Initiation, Maintenance, and Regulation", Biochemistry, vol. 30, No. 43 (1991), pp. 10363–10370.
D. J. Schneider, (MD), et al. "Differential Effects of Anticoagulants on the Activation pf Platelets Ex Vivo", Circulation, vol. 96, No. 9, (1997), pp. 2877–2883.
T. Ammar, MD, et al. "In Vitro Effects of the Platelet Glycoprotein IIb/IIIa Receptor Antagonist c7E3 Fab on the Activated Clotting Time", Circulation. vol. 95, No. 3, (1997), pp. 614–617.
B. Osterud, et al. "Activation of Factor IX By The Reaction Product of Tissue Factor and Factor VII: Additional Pathway For Initiating Blood Coagulation", Proc. Natl. Acad. Sci. (USA), vol. 74, No. 12 (1977), pp. 5260–5264.
O. D. Ratnoff, et al. "Inhibition of Ellagic Acid–Activated Hageman Factor (Factor XII) and Hageman Factor Fragments by Popcorn Inhibitor", Proc. Soc. Exp. Biol. Med., vol. 166, No. 2, (1981), pp. 297–299.
S. A. Kambhu, et al. "Inhibition of Hageman Factor (Factor XII) By Popcorn Inhibitor", J. Lab. Clin. Med. (USA), vol. 105, No. 5, (1985), pp. 625–628.
J. H. Lawson, et al. "A Model For The Tissue Factor Pathway To Thrombin", J. Biol. Chemistry, vol. 269, No. 37 (1994), pp. 23357–23366.
L. C. Pedersen, et al. "The Corn Inhibitor of Blood Coagulation Factor XIIa Crystallization and Preliminary Crystallographic Analysis", J. Mol. Biol. (England), vol. 236, No. 1, (1994), pp. 385–387.
S. I. Rapaport, et al. "The Tissue Factor Pathway: How It Has Become a 'Prima Ballerina'" Thrombosis and Haemostasis, vol. 74, No. 1, (1995), pp. 7–17.
Y. Hojima, et al. "Hageman Factor Fragment Inhibitor In Corn Seeds: Purification and Characterization", Thrombosis Research, vol. 20, No. 2, (1980), pp. 149–162.

(List continued on next page.)

*Primary Examiner*—Maureen M. Wallenhorst
(74) *Attorney, Agent, or Firm*—David G. Conlin; Robert L. Buchanan; Edward & Angell, LLP

(57) ABSTRACT

The present invention provides methods for inhibiting blood clotting. In general, the methods include adding corn trypsin inhibitor (CTI) to blood or a blood product in an amount sufficient to inhibit the clotting. The CTI can be used alone or in combination with other anti-coagulants. In one aspect, the invention features plasma clotting assays featuring substantially prolonged clotting times. Clotting assays using whole or minimally altered blood are also provided. Further provided are methods for storing blood or blood products at low temperature with the CTI.

26 Claims, 26 Drawing Sheets

OTHER PUBLICATIONS

Gregory A. Ewald M.D., et al.; "Plasmin–Mediated Activation of Contact System in Response to Pharmacological Thrombolysis", Circulation, vol. 91, No. 1, 1995, pp. 28–36.

Notification of Transmittal of the International Search Report or the Declaration (PCT/US99/12631).

* cited by examiner

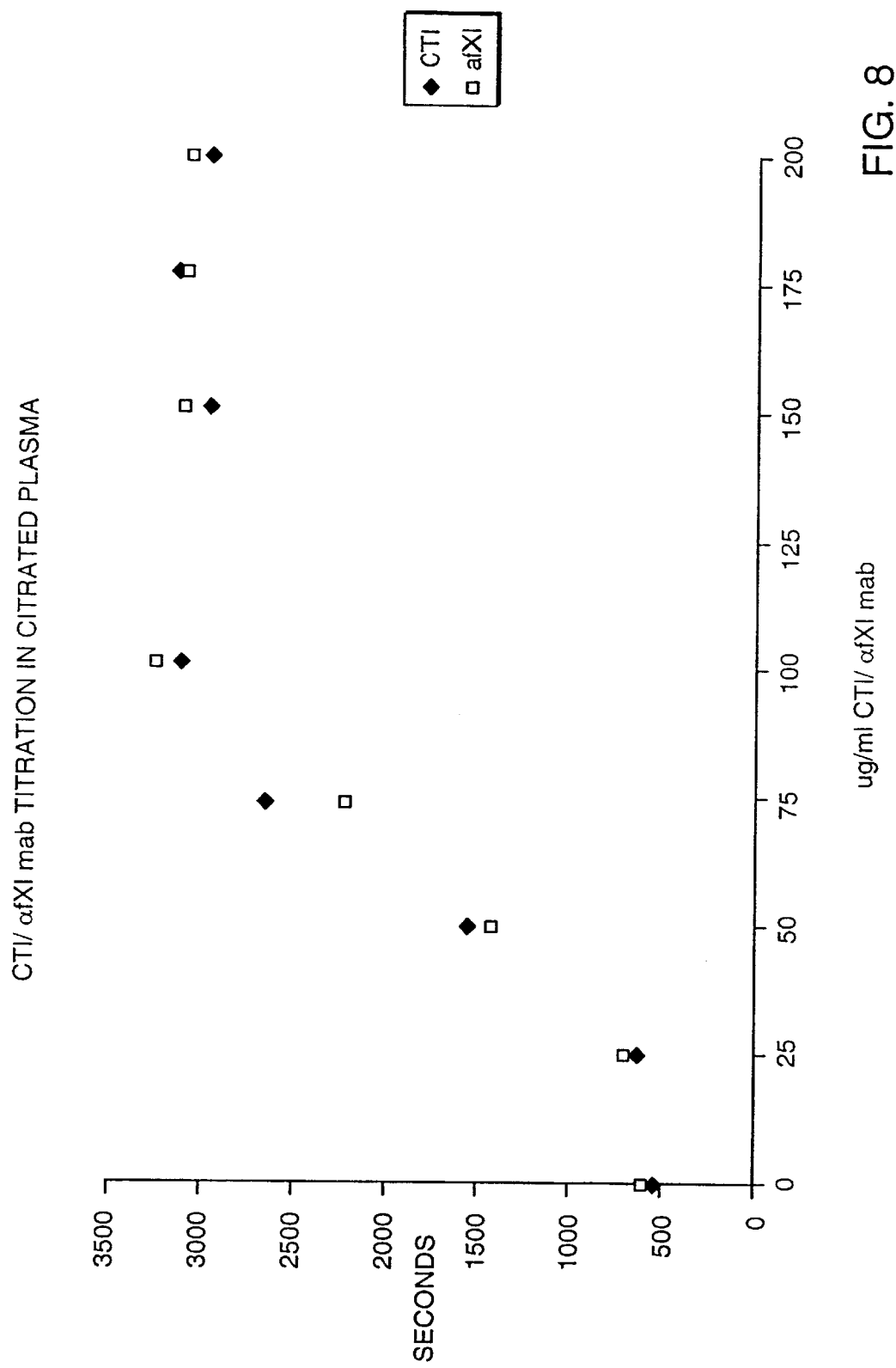

|  | American Red Cross | Hayes study |
|---|---|---|
| n(#individuals) | 25 | 26 |
|  | TFP assay seconds | cholesterol mg/dL |
| n | 103 | 204 |
| x | 80.78 | 197.26 |
| CVa (%) | 3.17 | 1.04 |
| CVi (%) | 5.42 | 9.28 |
| CVg (%) | 5.65 | 19.44 |
| Index.indiv | 0.96 | 0.48 |
| Index.het | 0.17 | 2.59 |
| Critical diff | 17.38 | 25.87 |

FIG. 13

CLOT TIME MEASUREMENT IN DEFICIENT PLASMA

| DEFICIENT FACTOR (0.1%) | CLOT TIME (SECONDS) 12.5 pM rTF | CLOT TIME (SECONDS) 0.5 nM rTF |
|---|---|---|
| FACTOR V | 606.0 | 306.2 |
| FACTOR VII | 595.0 | 230.0 |
| FACTOR VIII | 501.3 | 189.0 |
| FACTOR IX | 498.6 | 198.0 |
| FACTOR XI | 219.9 | 92.3 |
| PROTHROMBIN (II) | 651.2 | 309.1 |
| NORMAL POOLED PLASMA | 211.0 | 82.6 |

FIG. 14

TABLE 1

TISSUE FACTOR INITIATED CLOTTING TIMES (SECONDS)
CTI 200 μg/ml AND TISSUE FACTOR 10 pM

|  | INTRAINDIVIDUAL VARIATION IN 4 SUBJECTS ON 3 DAYS | | | | ALL SUBJECTS |
|---|---|---|---|---|---|
| SUBJECT | 1 | 2 | 3 | 4 | N = 20 |
| MEAN | 123 | 112 | 122 | 112 | 118 |
| S.D. | 9.6 | 4.9 | 15.9 | 3.2 | 9 |
| C.V % | 8 | 4 | 13 | 3 | 8 |

FIG. 19

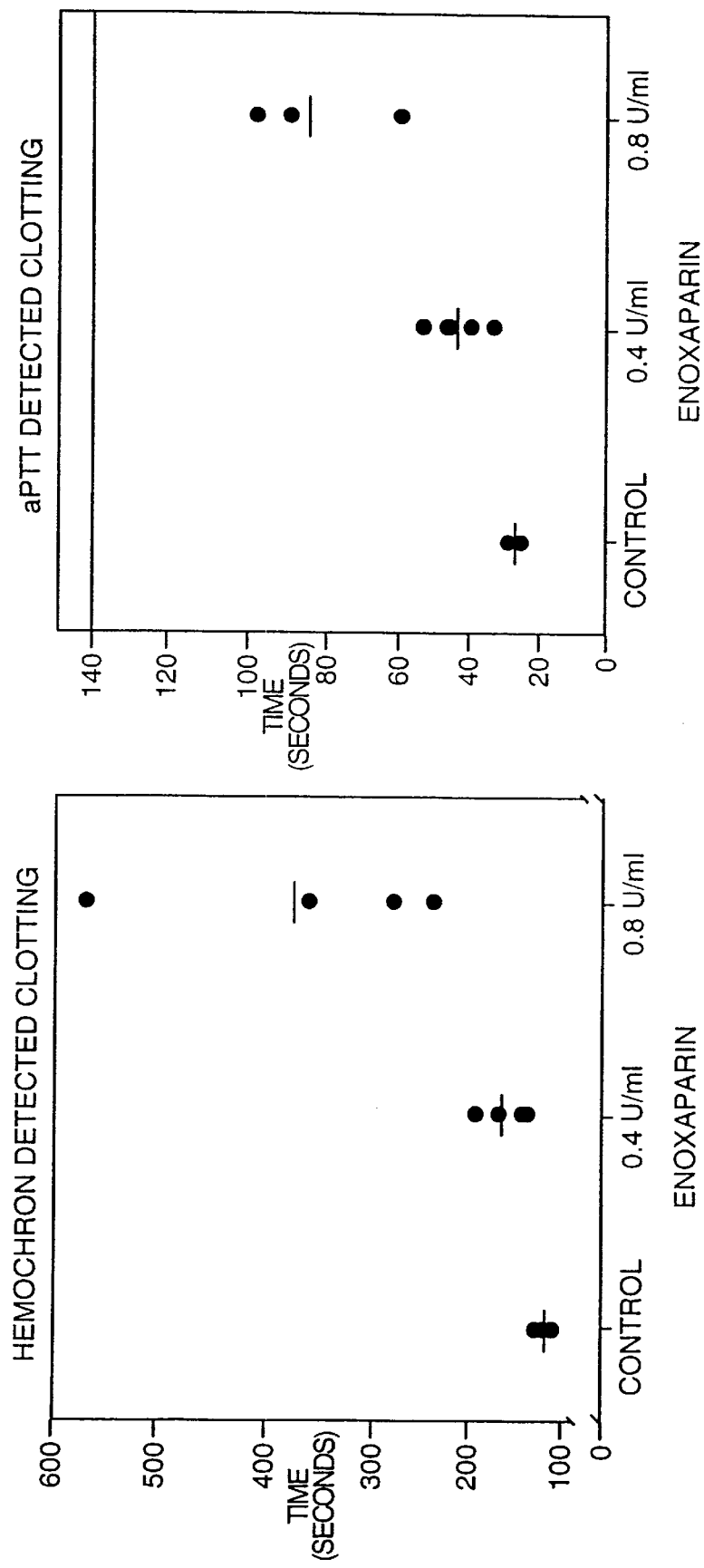

INHIBITION OF COAGULATION IN BLOOD AND BLOOD PRODUCTS

CROSS-REFERENCE TO RELATED APPLICATIONS

This application is a divisional of application Ser. No. 09/327,806, filed on Jun. 8, 1999 and now U.S. Pat. No. 6,403,381, issued on Jun. 11, 2002, which is a continuation of U.S. Provisional Application Ser. No. 60/088,488, filed Jun. 8, 1998, the disclosure of which is incorporated herein by reference.

FIELD OF THE INVENTION

The present invention generally relates to methods for measuring coagulation of blood and blood products, and more particularly, to the use of an inhibitor to minimize blood product coagulation in vitro, and obviate sources of inconsistency and errors in blood coagulation. The present invention has a variety of uses, e.g., prolonging plasma clotting times, optimizing sensitivity of plasma coagulation assays, and enhancing storage of blood and blood products such as plasma.

BACKGROUND OF THE INVENTION

Blood coagulation (clotting) assists homeostasis by minimizing blood loss. In vivo, clotting usually requires vessel damage, platelet aggregation, coagulation factors and inhibition of fibrinolysis. The coagulation factors have been reported to act through a cascade that relates vessel damage to formation of a blood clot. See generally L. Stryer, *Biochemistry*, 3rd Ed, W. H. Freeman Co., New York; A. G. Gilman et al., *The Pharmacological Basis of Therapeutics*, 9th Edition, McGraw Hill Inc., New York, pp.1341–1359; and Mann, K. G. et al. (1992) *Semin. Hematol.* 29:213.

Initiation of blood coagulation arises from two distinct pathways: the intrinsic (contact) and extrinsic pathways. The intrinsic pathway can be triggered in vitro by contact of blood borne factor with artificial negatively charged surfaces such as glass. In contrast, the extrinsic pathway can be initiated in vivo or in vitro when tissue factor (TF) on a phospholipid surface, normally sequestered from the circulatory system, comes into contact with blood following injury. Both pathways are characterized by the assembly of multiple protein complexes on procoagulant surfaces, which serves to localize the response to the site of injury. See e.g, Mann, K. G. et al. (1990) *Blood* 76: 1; Mann, K. G. et al. (1992), supra.

Current theories of coagulation maintain that interplay between the two pathways is required for efficient blood clotting. See S. I., Rapaport and L.V.M. Rao (1995) *Throm. Haemost.* 74: 7; and Stryer, L. supra and references cited therein.

The contact pathway has been further divided into early and late steps. These steps are typically associated with specific coagulation factors. For example, the early contact pathway is associated with activated prekallikrein and Factor XII, whereas the late contact pathway involves Factors VIII and IX. It has been reported that hemophilia A, B and C are each correlated with deficiencies in the late contact pathway (Factor VIII, Factor IX, and Factor XI, respectively). Hemorrhagic tendencies have not been found for prekallikrein or factor XII deficiency. Accordingly, these early contact factors are not thought to be relevant for initiation and maintenance of coagulation. See e.g., Davie, E. W. et al. (1991) *Biochem.* 30:10363.

Many activities of the extrinsic and intrinsic tenases (factor VIIIa-factor IXa) and the prothrombinase complex are facilitated by activated platelets and other phospholipid membranes. Characterization of the impact of therapeutic agents in vivo is usually analyzed by methods in which the contact pathway is attenuated or eliminated. See Nemerson, Y. (1988) *Blood* 71:1, Rand, M. D. et al. (1996) *Blood* 88: 1; and Monroe, D. M. et al. (1994) *Brit. J of Haemot.* 88: 364.

There have been attempts to understand how blood coagulation is initiated and controlled. One approach has been to reproduce blood coagulation as it is thought to occur in vivo. For example, by analyzing reactions associated with blood coagulation in vitro, it has been possible to detect relationships between certain blood coagulation factors. Specific attempts have involved analysis of fractionated blood and particularly blood products such as plasma. Current in vitro models of blood clotting focus on the activity of specific blood factors. See e.g., Davie, E. W. et al. supra.

Confusion about the role of these pathways in coagulation has arisen from several difficulties such as in processing, storing, and studying blood and blood products. Untreated whole blood or blood products such as plasma typically coagulate within minutes. The clotting can be reduced or eliminated by addition of a calcium-chelating agent such as citrate. In particular, citrate has been reported to interfere with the assembly and function of prothrombinase and extrinsic and intrinsic tenases. Citrated blood can be stored in liquid form for a limited period of time (e.g., days to weeks) , or can be manipulated to produce blood products such as blood cell isolates, platelet rich and platelet poor plasma. Plasmas that include citrate can be stored for extended periods (months to years) by freezing at temperatures below about $-70°$ C. In most instances, the plasma is recalcified for use. However, recalcified plasma will typically clot spontaneously due to contact activation in most storage vessels, where contact activation can occur within about 2 to 4 minutes. As a result, most coagulation assays are usually performed on citrated plasma fractions that have been frozen for storage then thawed. However, such fractions cannot be recalcified until immediately prior to use.

Coagulation tests are often performed either on blood or blood products. In simple tests such as bleeding time tests, wounds are made in a patient and the time until clot formation is noted. Additionally, whole blood coagulation tests have been devised by drawing blood directly into a tube, then rocking or agitating until a clot is observed. Such tests are not very informative, as the sources of initiation are not well controlled and comparisons among patients are difficult. In clinical settings, citrated plasma isolates are the most widely used blood product for coagulation testing, due to prominence of the prothrombin time (PT) and activated partial thromboplastin time (aPTT) tests. The PT is the more convenient assay, and is performed by addition of a large quantity of thromboplastin to the citrated plasma, with subsequent initiation of the reaction by calcium addition. The time to clot formation is noted, which for most normal donors is typically about 10 to about 14 seconds. The aPTT test involves about a 3 to about 5 minute preincubation of the citrated plasma with a mixture of phospholipids and solids possessing negatively charged surfaces. The reaction is initiated by calcium addition, and the clot time for normal donors typically falls between 25 and 43 seconds. While well established in the clinical venue, neither assay is entirely suitable to mimic the physiological coagulation reaction in its entirety. See generally *Williams Hematology*, infra.

For example, while the PT measurement employs the physiologically relevant initiator TF and the assay is sensitive to Factors V, VII, X, and prothrombin (II), the concentration used is sufficiently high that the reaction is usually insensitive to deficiencies or abnormalities in coagulation Factors VIII or IX. Clotting occurs rapidly in normal individuals (about 10 to about 14 seconds), and errors in measurement on the order of seconds are a significant fraction of the total clot time. When the assay is used to monitor administration of anti-coagulants, the target range for prolongation of the clot time is between about 2.5 to about 3.5 times normal, or between about 25 and 49 seconds. There has been recognition that this time range is often too small to permit accurate analysis.

The aPTT assay is also associated with problems. For example, since initiation proceeds through the early contact pathway members, Factor VII is bypassed in this reaction. As a result, this assay in insensitive to deficiencies or abnormalities in this biologically important coagulation factor. For this reason, the aPTT is not typically considered suitable for monitoring anti-coagulation by coumadin or other warfarin derivatives which strongly affect the ability of Factor VIIa to serve as an initiator of the coagulation reaction.

Additionally, most aPTT assays use plasma and are not compatible with whole blood. Thus, a source of phospholipid must often be provided, and the contributions of platelets and other cells or inhibitors of cellular processes cannot be assessed. Certain whole blood clotting assays and particularly the activated clotting time (ACT) are reported to be responsive to antiplatelet regimens. See e.g,. Moliterno, D. J. et al. (1995) *Am. J. Cardiol.* 75: 559; Ammar, T. et al. (1997) *Circulation* 95:614.

Furthermore, recalcified plasma will typically clot spontaneously owing to the contact pathway. Supraphysiologic concentrations of tissue factor must often be added to perform the PT with reproducible results. The resulting rapid time to clot (less than about 15 seconds) eliminates the contribution of the intrinsic tenase and substantially limits assay sensitivity to a variety of therapeutic agents. See e.g., Schultz, N.J. (1991) *Pharmacotherapy* 11: 312.

Although there has been some progress toward controlling coagulation of blood, plasma and other blood products in vitro, there is a need for improved methods for storage of these materials. For example, while citrate and other calcium chelators such as ethylene diamine tetraacetate (EDTA) are usually effective attenuators of prothrombinase and tenase assembly and function, these chelators have little effect on the early contact reactions involving Factor XII, Factor XI and prekallikrein activation which often proceed unchecked during storage. Other methods have been developed involving use of certain charged polymers such as heparinoids. These compounds are usually effective in reducing spurious clotting in blood and blood products. However, these compounds have drawbacks as well. See e.g., A. G. Gilnan et al. supra.

These and related problems have also hampered whole blood coagulation assays. For example, prior practice has dictated rapid analysis of the whole blood within minutes of sampling. One approach has been to prepare plasma from the whole blood to facilitate analysis at a later time. However as noted, it has been difficult to perform assays which are sensitive, reproducible, and produce accurate models of in vivo coagulation. See also Osterud, B. et al. (1977) *PNAS* (USA) 74:5260.

There has been some progress toward controlling whole blood coagulation in vitro. For example, corn trypsin inhibitor (CTI) has been used to reduce whole blood coagulation in vitro. See e.g., Rand, M.D. (1996) et al. *Blood,* 88: 3432; Hojima,Y. et al. (1980) *Thromb. Res.,* 20: 149; and Munakata, M. et al. (1996) *Rinsho Byori* (Japan), 44: 883.

However, prior use of CTI has been associated with drawbacks. For example, it has been unclear whether CTI can inhibit clotting of plasma and other blood products. In particular, there has been recognition that fractionation or prolonged storage of whole blood may adversely impact the capacity of CTI to prolong clotting times. Additionally, some blood products and especially plasma are routinely subjected to multiple cycles of freezing and thawing. Those cycles may also impact CTI effectiveness. Moreover, CTI may not always inhibit clotting of whole blood or blood products in a reproducible manner. These and other considerations have limited use of CTI as a coagulation inhibitor.

It would be desirable to have efficient and reproducible methods for measuring coagulation of whole blood and blood products such as plasma that more closely resemble in vivo coagulation. It would be especially desirable to have tissue factor initiated plasma coagulation assays that exhibit prolonged clotting times and enhanced sensitivity to late contact pathway factors and particularly Factors VIII and IX.

SUMMARY OF THE INVENTION

The present invention features methods for measuring coagulation of blood and blood products, and more particularly, to the use of a specific inhibitor to minimize blood product coagulation in vitro, and to obviate sources of inconsistency and errors in blood coagulation. In one aspect, the methods include adding corn trypsin inhibitor (CTI) to plasma in an amount sufficient to enhance coagulation analysis. The methods have several important uses, e.g., to increase the sensitivity and reproducibility of plasma coagulation assays, and to prolong lifetimes of blood cell or plasma isolates.

Additionally provided by this invention are methods for inhibiting coagulation of blood or a blood product. Preferred blood is whole or minimally altered blood from a mammal and particularly a human patient. A preferred blood product is plasma such as frozen plasma or other plasmas as described herein. In one embodiment, the methods significantly reduce or eliminate coagulation in the blood or blood product sufficient to provide for enhanced coagulation analysis or storage of the blood or blood product. Especially preferred methods-employ an effective amount of corn trypsin inhibitor (CTI) to inhibit coagulation of the blood or blood product The CTI can be used by itself as a sole anticoagulant or the CTI can be used in combination with a sufficient amount of at least one other anticoagulant as described below..

In particular, we have discovered that CTI can be used to provide enhanced and more accurate results in clotting analysis both in whole blood and blood products such as plasma. In one aspect, the invention features methods for substantially prolonging clotting of a blood product by adding a sufficient amount of CTI to reduce or eliminate intrinsic (contact) coagulation. In one embodiment, the CTI inhibits plasma clotting time by facilitating a significant reduction in contact coagulation. Preferably, the amount of added CTI is sufficient to inhibit the plasma clotting time in recalcified plasma in excess of between about 1000 to about 3600 seconds or longer when compared with a suitable control in the same coagulation assay. Additionally preferred use of the methods provide plasma clotting times wherein the desired International Normalized Ratio (INR) is between about 1 and about 3.5 and in some instances up to about 6.5. The substantially prolonged clotting times achievable by the present methods substantially enhances the sensitivity and reproducibility of a variety of coagulations assays such as those described below.

By reference herein to a "blood product" or like term is meant a purified composition derived from whole blood from a mammal and especially a human patient. Preferably, at least one blood component (e.g., blood cells, blood factors, or blood related proteins) has been removed from the whole blood. Particular blood products are deficient in at least one specific cell type such as red blood cells, white blood cells (immune cells), and platelets. A preferred blood product is plasma, ie. the fluid portion of blood. A particular type of plasma is referred to as "platelet poor" or "platelet deficient" plasma.

The amounts or specific activity of CTI used in the present methods varies depending on several parameters such as intended use and more specifically to the degree of inhibition desired. However, in most instances the amount or specific activity of the CTI will be sufficient to prolong the clotting time of a desired blood product by between about 100 to about 2000 seconds or longer up to about 3600 seconds when compared to a control in the same coagulation assay. In a specific embodiment, the amount of CTI used will be sufficient to prolong plasma clotting time and particularly the clotting time in platelet-deficient plasma as determined by a suitable coagulation assay.

We have also found that CTI extends the useful range of certain modified coagulation assays such as those described below. This extension is desirable to ensure responsiveness to blood coagulation factors and particularly Factors VIII and IX in certain assays. In particular, plasma clotting assays that mimic the physiological coagulation reaction will be improved by sensitivity to levels of the Factors VIII or IX in the range of between about 0 units/ml to about 1 unit/ml up to about 2 units/ml or more.

Importantly, it has also been found that the CTI provides for more uniform and reproducible analysis of coagulation especially using plasma. The sensitivity and reproducibility of the present methods makes them especially useful for characterizing blood disorders associated with abnormal levels of these and other coagulation factors including prothrombin Factor V, Factor VII, Factor X and Factor XI.

Without wishing to be bound by any theory, it is believed that CTI improves clotting assays by reducing or eliminating adverse effect of the contact pathway, the effect of which can vary depending on the compositions of the samples and the nature of the surfaces those samples contact. Importantly, it is also believed that use of CTI in accord with the present invention makes certain coagulation assays more representative of in vivo coagulation reactions.

Specific use of the methods involves adding plasma and particularly platelet-deficient plasma to a reaction vessel comprising a suitable amount of CTI. Preferred are methods in which the reaction vessel further includes at least one suitable anti-coagulant such as a buffered calcium-chelating compound. The CTI and anti-coagulant can be provided in any suitable form such as a pre-determined amount of a liquid, suspension or lyophilized material. More specific examples of anti-coagulants suitable for use with the present invention are provided below.

We have also found that CTI can be used to facilitate storage of whole blood or a blood product at reduced temperature e.g., about freezing or below freezing temperatures. More specifically, by supplementing the whole blood or blood product with an amount of CTI sufficient to reduce or eliminate contact coagulation, effective and reproducible analysis of the whole blood or blood product is more readily obtained. In particular, the CTI has been found to remain a potent anti-coagulant even if the blood or blood product is subjected to one or more freeze-thaw cycles.

Accordingly, in one aspect, the invention features methods for storing blood or a blood product which methods involve contacting same with a suitable amount of CTI. In one embodiment, the methods involve freezing blood or the blood product in the presence of the CTI, e.g., by adding the CTI to a freezing or previously frozen blood or blood product. In a specific embodiment, the CTI can be layered on top of the frozen blood or blood product. In this instance, the frozen blood or blood product exhibits substantially prolonged clotting time when subjected to a clotting permissive temperature. Significantly, the methods can be used to improve storage of whole blood or blood products such as plasma by decreasing or eliminating intrinsic coagulation if the whole blood or blood product is subjected to a clotting permissive temperature.

Further provided are methods for measuring clotting in blood or blood products and especially plasma. In one aspect, the methods involve adding a suitable amount of CTI to suitable coagulation assay to facilitate prolonged clotting. For example, the invention can be used with a PT assay with samples obtained from a patient receiving anti-coagulant therapy. In a more specific embodiment, the CTI can be used in a PT assay with platelet poor plasma. The CTI can be used to reduce or eliminate contact coagulation-in other assays such as the dilute thromboplastin assay or those specific assays sensitive to Factors VIII, IX or XI described below.

In one embodiment, the methods include treating a blood product with at least one anti-coagulant, e.g., a calcium-chelating agent or heparinoid, and then subjecting the blood to conditions conducive to making the blood product. In a more specific embodiment, the blood product is plasma and the conditions include conventional filtration or centrifugation steps to reduce or eliminate unwanted blood cells from the blood. In this embodiment, the plasma is also contacted with an amount of CTI sufficient to inhibit or eliminate contact coagulation. In cases in which the anti-coagulant is a calcium-chelating agent, the plasma is preferably recalcified. The recalcified plasma can then used in a desired coagulation assay.

If desired, the method can be modified by adding a suitable amount of CTI to the blood before or after treating with the anti-coagulant(s).

Also provided by this invention are novel blood clotting assays that are suitably adapted for use with whole or minimally altered blood. The assays have a wide spectrum of important uses including what is sometimes referred to as "point-of-care" analysis. That is, preferred blood clotting assays are compatible with bedside use, e.g., in a hospital, outpatient or home setting. This feature of the invention facilitates analysis of blood coagulation essentially in "real-time", thereby improving patient management and enhancing assessment of therapeutic agents in the blood. More particular blood clotting assays are sensitive to relevant plasma and cellular events involved in blood coagulation including management by pharmacological agents. In preferred blood clotting assays, coagulation is initiated with low concentrations of lipidated tissue factor while the contact pathway is suppressed with CTI. Significantly, the assay detects the activity of a wide variety of agents such as anticoagulants and especially antithrombotic and/or antiplatelet agents with increased sensitivity. The assay also facilitates detection of additive and synergistic effects of combinations of the agents. Additional uses and advantages of the point-of-care blood clotting assay are discussed below and in the Examples.

Additionally provided are methods for assaying clotting of blood products that have been subjected to freezing or below freezing conditions. As noted, use of CTI in accord with the present invention can provide potent anti-coagulant activity that is significantly resistant to one or multiple freeze-thaw cycles. In one aspect, the methods include treating whole blood with at least one anti-coagulant, preferably a calcium-chelating agent or heparinoid, and then subjecting the whole blood to conditions conducive to making the blood product. In one embodiment, the blood product is plasma and the treated whole blood is subjected to particular conditions described herein for making plasma. In this embodiment, the plasma is frozen and then contacted with a suitable amount of CTI. In a particular embodiment, a suitable amount of CTI is added to the frozen plasma in an amount sufficient to inhibit or eliminate contact coagulation. In another embodiment, the CTI is mixed with the plasma prior to or during freezing. In either chase, contact coagulation of the plasma can be significantly reduced or eliminated if the plasma is subjected to a clotting permissive temperature. In instances where the anti-coagulant is a calcium-chelating compound such as a citrate salt, thawed plasma is recalcified. The recalcified plasma can then be used in any suitable coagulation assay.

Also provided is what is sometimes referred to herein as an Extended Plasma Prothrombin Time (XpPT) assay. In one embodiment, the assay can be used to suitably measure coagulation in blood products such as plasma and especially frozen or previously frozen plasma. As discussed below, the assay is very flexible and has a number of important applications including use as a convenient tool for implementing nearly universal hemostasis management. More particularly, the assay can be used to monitor and quantify (if desired) clotting reactions indicative of abnormal bleeding such as those associated with congenital bleeding disorders. The assay is also useful for monitoring the impact of anti-coagulant therapy. Significantly, the assay can be titrated in accord with the I.S.I., thus leading to a nearly universally equivalent anticoagulant monitoring system that is usually independent of thromboplastin source. This advantage of the invention reduces or eliminates need to "stockpile" blood coagulation reagents, thereby making analyses more cost effective and easier to perform. As discussed below, the assay can be used to optimize "difficult-to-standardize" reagents such as thromboplastin.

The above-described methods can be modified according to intended use. For example, a suitable amount of CTI can be added to the whole blood prior to making the desired blood product. Preferably, the CTI is added in an amount sufficient to inhibit or eliminate coagulation of the blood or the blood product.

The invention features additional methods for significantly reiducing or eliminating contact clotting in a suitable coagulation assay. In one aspect, the methods include treating whole blood with a suitable amount of CTI and at least one other anti-coagulant, preferably a calcium-chelating agent or heparinoid. The treated whole blood is then subjected to conditions conducive to making the blood product. In a one embodiment, the blood product is plasma. In instances where the anti-coagulant is a calcium-chelating compound such as a citrate salt, the plasma is recalcified. The recalcified plasma can then be used in a suitable coagulation assay.

The present invention features significant advantages. For example, specific methods described herein involve a suitable coagulation assay to which CTI is added. In this example, the assay can utilize tissue factor (TF) and especially relipidated TF at much more dilute concentrations than could heretofore be used in most prior coagulation assays such as prior PT and thromboplastin assays. In particular, a plasma coagulation assay conducted in accord with the invention can initiate extrinsic coagulation with about 1 nM or less TF. The present methods also desirably prolong clotting times by inhibiting or eliminating unwanted contact coagulation. As discussed, contact coagulation often masks physiologically relevant coagulation reactions. Thus, the invention provides methods of assaying coagulation that more closely resemble in vivo coagulation. In particular, addition of CTI to the assay makes that specific assay less dependent on high levels of TF and more representative of in vivo clotting.

The invention provides further advantages. For example, the invention provides sensitivity to Factor XI at low TF concentrations, e.g,. below about 25 pM. Thus, the methods allow effective monitoring of coagulation factors for which analysis has been heretofore difficult to achieve.

Importantly, the invention provides an effective and reproducible means of assaying coagulation in patients receiving anti-coagulant therapy. For example, addition of CTI to a coagulation assay in accord with the invention provides more uniformity in INR value determinations. In particular, prior practice has made it difficult to obtain accurate INR values for those patients receiving anti-coagulants such as coumadin. The present invention allows for more uniformity by making linear relationships easier to obtain, ie., between clotting times and INR values.

The invention provides still further advantages. For example, particular methods described herein use citrated plasma to remove calcium. Addition of CTI to the recalcified plasma enhances use of that plasma by reducing or eliminating interference from contact activation. Thus, practice of the invention enhances the initiation of clotting by TF rather than calcium. In contrast, prior practice has generally dictated initiation of clotting by calcium addition. Thus, the present invention facilitates use of coagulation assays and especially the dilute TF assays by improving sample handling.

These and related advantages of the invention enhance practice of the present methods in a variety of settings such as those associated with commercial, medical, clinical, hospital or research applications.

As noted, the present invention is flexible and can be adapted to suit intended use. For example, the present methods can be modified if desired to combine platelet poor plasma with contact pathway inhibitors, thereby allowing advance recalcification of the plasma while avoiding opportunities for spurious contact-activated coagulation.

As also noted, the present invention can provide effective and reproducible inhibition of contact clotting in a blood product that is frozen or has been subjected to multiple freeze-thaw cycles. Thus, specific methods described herein can also be employed to facilitate more efficient handing and use of frozen or previously frozen blood products and particularly plasma such as platelet-deficient plasma.

Additional aspects and advantages of the invention are discussed infra.

BRIEF DESCRIPTION OF THE DRAWINGS

FIG. 8 is a graph showing citrated plasma clot time after recalcification in the presence of corn trypsin inhibitor (qTI) and anti-Factor XI antibody.

FIG. 13 is a table showing standardization of the extended plasma prothrombin time (XpPT) assay with tissue factor (TF).

FIG. 14 is a table showing coagulation time measurements in the extended plasma prothrombin time (XpPT) assay for deficient plasma measured with tissue factor (TF)

FIG. 19 is a table showing tissue factor initiated plasma clotting times (seconds) in human patients.

FIGS. 23A and 23B are graphs showing the effect of enoxaparin on clotting time. Shown are hemochron-detected clotting (FIG. 23A) and aPTT detected clotting (FIG. 23B).

DETAILED DESCRIPTION OF THE INVENTION

Figure 1:
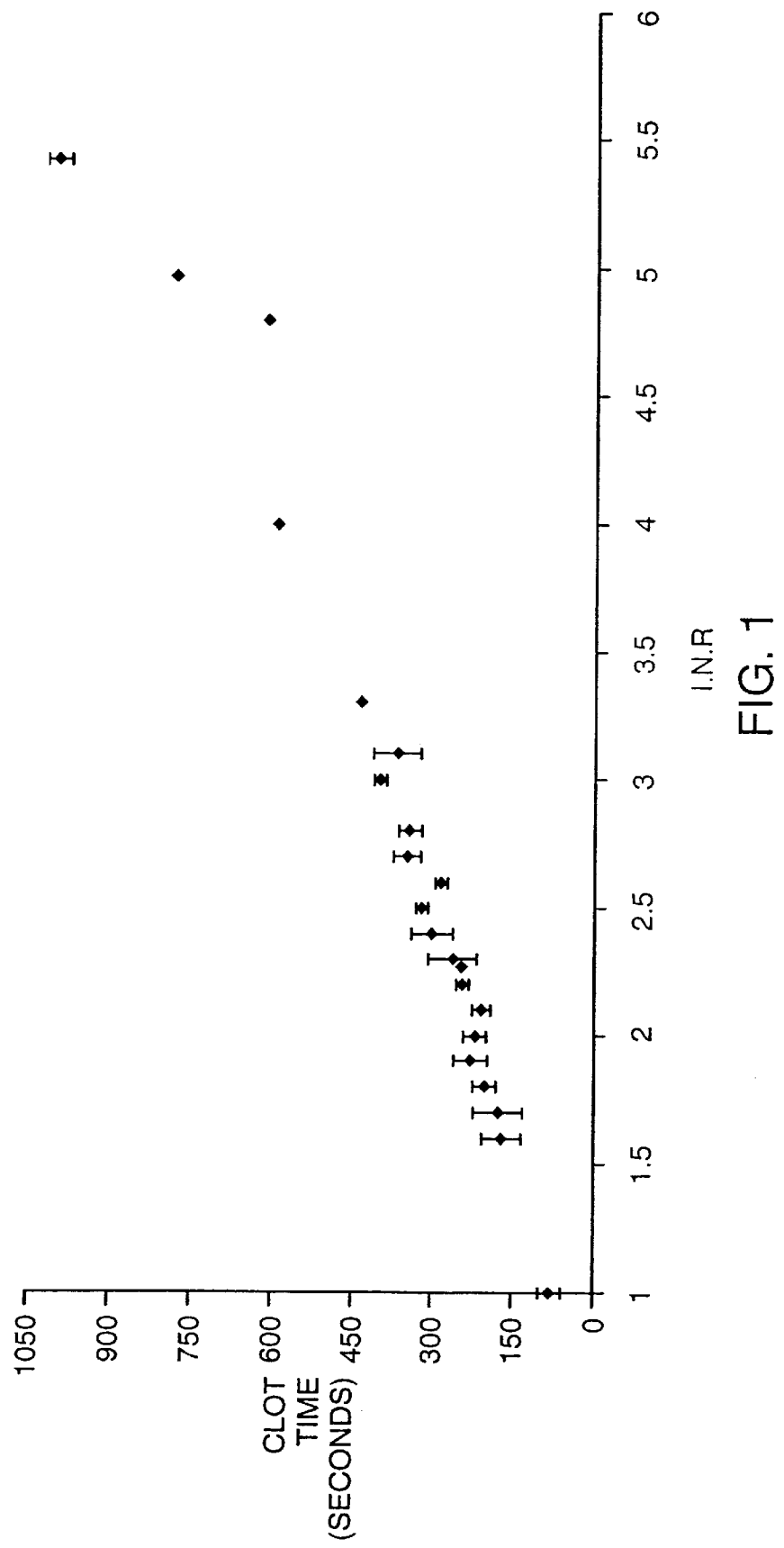
FIG. 1 is a graph showing TF pathway assay vs. I.N.R from PT in plasma from patients undergoing coumadin treatment. Recalcified plasma includes 0.10 mg/ml CTI.

As discussed, the present invention provides methods for measuring coagulation of blood and blood products, and more particularly, to the use of an inhibitor to minimize blood product coagulation in vitro, and obviate sources of inconsistency and errors in blood coagulation. Particular methods described herein allow for a significant reduction or elimination of intrinsic coagulation of certain blood products such as plasma and particularly platelet poor plasma. In particular embodiments, the present methods feature use of a suitable amount of corn trypsin inhibitor (CTI) to prolong plasma clotting in suitable coagulation assays such as those specifically described below. Significantly, practice of the present invention makes many prior coagulation assays and especially those using plasma more representative of in vivo coagulation, e.g, by enhancing responsiveness to coagulation Factors VIII and IX and reducing or eliminating dependence on high levels of added TF.

Additionally provided are methods for enhancing coagulation analysis of whole or minimally altered blood, as well as blood products such as plasma. Also provided are methods for enhancing storage of the blood or blood products. As discussed, the methods involve contacting the blood or blood product with an amount of CTI sufficient to reduce or inhibit coagulation over a desired period of time. The CTI can be used alone or if needed can be used in combined with a sufficient amount of at least one other naturally-occurring or synthetic anticoagulant such as a blood factor antibody to further decrease or eliminate the clotting. The methods are flexible and can be tailored to suit intended use. Examples of such use include monitoring and optionally measuring coagulation in the blood or blood product for several seconds up to about one to a few hours following isolation from a human patient. Additional use includes short- or long-term storage of the blood or blood product especially at reduced temperatures for about a few hours up to several days or weeks,. Preferred amounts of CTI for use in these and other methods of this invention are provided below.

The present invention addresses a need for coagulation assays and particularly plasma coagulation assays, that more closely resemble clotting in vivo. As discussed, use of CTI in accord with the present methods allows straightforward detection of coagulation while minimizing or eliminating interference from contact coagulation. Also, addition of CTI to a plasma coagulation assay allows clotting initiation with a lower TF concentration than has heretofore been possible using prior coagulation assays. At the lower TF levels achievable with the present invention, the assays are believed to be more sensitive to classical extrinsic pathway and the later members of the contact pathway (particularly factors VIII and IX, as in hemophilias A and B). Significantly, the use of the invention can minimize or exclude effects of the early contact pathway (particularly activation of prekallikrein and factor XII). See e.g., Rapaport, S. I. and Rao L. V. M. (1995) *Thromb Haemost*, 74:7.

Additionally, the invention facilitates use of coagulation assays by providing increased assay reproducibility and fidelity.

The plasma coagulation assays described herein are offer significant improvements over prior assays. For example, many prior plasma coagulation assays use TF levels of between about 5 nM TF or greater and do not usually detect abnormalities in Factors VIII or IX. Although some prior assays that use somewhat lower TF levels, those prior assays are still adversely affected by spurious activation of the early contact pathway. In contrast, the present methods can be used with exceptionally dilute TF concentrations, ie. in the range of 1 nM or less and particularly between about 1 pM to about 1 nM. Moreover, the present methods are fully sensitive to coagulation factors such as Factors VIII and IX. Thus, use of CTI in accord with the invention can provide an extended range of clot times at low TF concentrations while minimizing or excluding interference from some members of the early contact pathway (e.g., kallikrein or factor XIIa). Further, low TF levels that can be achieved through use of the invention can provide a more desirable coagulation rate (ie. slower) than most prior assays, thereby allowing more precise and reproducible analysis of clotting.

Practice of the present invention generally involves standard methods for preparing, testing and manipulating blood products. More specific techniques for obtaining blood, preparing plasma and particularly platelet-deficient plasma, and storing blood or blood products at low temperature have been disclosed. See e.g., *Williams Hematology*, infra, Chapters 151, 153, L33 and L53.

By the term "platelet deficient" or "platelet poor" is meant that the plasma includes negligible levels of platelets as determined by standard methods such as electric impedance or other automated methods. See e.g., M. W. Morris et al. in *Williams Hematology*, infra, Chapter L1.

Reference herein to suitable amount of CTI or related phrase means an amount of CTI sufficient to inhibit or eliminate contact clotting in a desired coagulation assay. Particular amounts of CTI to use will be governed by recognized parameters such as the extent of clotting inhibition needed.

By the term "coagulation assay" or related term is meant an assay featuring TF dependent coagulation such as the PT, dilute thromboplastin, aPTT, or specific Factor VIII, IX or XI assays described below. The coagulation assay will typically include a suitable amount of CTI sufficient to-inhibit or eliminate contact coagulation. Preferred are coagulation assays in which optimal coagulation is observed at dilute TF concentrations such as those below about 1 nM.

As discussed, the present invention is well-suited for use with whole blood or blood products such as plasma. Particular types of plasma that can be used with the present methods include "standard" plasma which typically includes platelets and platelet-deficient plasma. General methods for making plasma and particularly platelet deficient plasma are described below.

Other types of plasma are suitable for use with the invention. For example, the invention can be used to prolong clotting times in a suitable coagulation assay using fractionated plasma, ie., in which at least one plasma protein has been removed (e.g., a blood coagulation factor). Methods for fractionating plasma are known in the field and include conventional immunological techniques such as affinity chromatography. Additionally, the methods described herein can be used to prolong clotting times with "reconstituted" plasma in which at least one pre-determined plasma factor has been added to plasma, e.g, standard plasma or platelet poor plasma. Methods for making and using plasmas such as platelet-poor, reconstituted, and supplemented plasmas are known in the field and have been disclosed. See e.g., *Williams Hematology*, infra, Chapter L53.

Preferred use of the invention involves a plasma coagulation assay and particularly an assay using plasma be obtained from a mammal. Particular mammals of interest include primates and especially humans, e.g., patients. In one embodiment, the plasma is isolated from a patient who has or is suspected of having a blood coagulation disorder, e.g., a hemostatic or thrombotic abnormality, coagulation inhibitor deficiency, or a disseminated intravascular condition. More particularly, the patient will have or be suspected of having a deficiency in at least one blood coagulation factor, e.g., Factor VIII, IX ( or both) such as in hemophilia type a, b, or c. See e.g., *Williams Hematology*, infra, Table 126-1 in Chapter 126.

Additional patient samples are within the scope of the present invention. For example, plasma can be obtained from patient having or suspected of having a condition which predisposes to thrombosis, e.g., Factor $V^{Leiden}$, Protein C deficiency, or an anti-thrombin III deficiency.

In another embodiment, patients from which a plasma sample is obtained may not always be associated with history of a hemostatic or thrombotic abnormality. For example, in specific embodiment, the plasma may be provided by a patient who is undergoing, has experienced, or who is about to undergo an invasive surgical procedure. More specifically, the invasive surgical procedure may arise from a patient who has been subjected to insertion of a needle, stent or related device to obtain blood. As an illustration, the invasive surgical procedure may be conducted to ascertain coagulative capacity of patient blood. For example, the patient may be receiving or about to receive a heparinoid, e.g, heparin; warfin, coumadin, or related anti-coagulant; e.g., as a prophylactic to prevent or reduce occurrence of clotting in vivo. Importantly, the present invention provides for efficient and reproducible testing of plasma coagulation obtained from these patients.

A preferred thrombotic or disseminated intravascular condition may or may not be associated with a deficiency or abnormality in a coagulation regulator or an acquired deficiency or abnormality, e.g, acquired autoantibodies against Protein C or S.

As discussed above, preferred methods of the invention prolong clotting of plasma and particularly platelet-deficient plasma by adding a suitable amount of CTI. As also discussed, that amount of CTI is sufficient to reduce or eliminate contact coagulation in the assay. Preferably, the amount of added CTI is sufficient to inhibit the plasma clotting time from between about 10 to about 3600 seconds longer than a suitable control, particularly about 50 to about 1500 seconds, and more particularly about 150 to about 1050 seconds longer than the control. Additionally preferred are amounts of CTI that provide clot times with an International Normalized Ratio (INR) of between about 1 to about 6.5, particularly about 1 to about 3.5 with between about 3.5 to about 6.5 or greater being typical for samples obtained from patients undergoing anti-coagulant therapy. Additionally preferred are amounts of CTI that provide sensitivity to amounts of Factor VIII or IX in the range of between about units/ml to about 1 unit/ml. More particularly definitions for units of Factor VIII and IX units can be found in *Williams Hematology*, infra, Chapter L37.

By the term "normal" as it is used with respect to whole blood or a blood product such is plasma is meant material from a healthy donor as that term is understood in the field.

It is recognized that many healthy donors have Factor VIII and IX levels in the range of about less than 1 nM (Factor VIII) and 100 nM (Factor IX). Certain normal donors have been reported to have-Factor VIII and Factor IX levels of about 0.7 nM and 90 nM, respectively. Reference herein to a particular method of the invention being sensitive to Factor VIII or IX means that the method is responsive to the factors at about the specified ranges. See Examples 1–4 which follow.

A variety of controls are suitable for use with the present methods. For example, in embodiments where plasma clotting is measured, the control can be essentially the same plasma sample used in the (experimental) method except that the control will not usually include any added CTI. The increase in clotting time facilitated by adding the CTI to the experimental plasma sample can be readily observed by detecting and then comparing coagulation between the experimental and control samples. In some specific cases, the control will be whole blood or a blood product such as plasma that has been obtained from a healthy donor.

Methods for detecting coagulation are known in the field and can be conducted, e.g., by inspection of reaction vessels comprising a desired coagulation assay. As noted, preferred use of the present methods involves prolonging plasma clot times in a suitable coagulation assay. Specific methods for conducting coagulation assays such as the PT and aPTT assays can be found in the examples below. See also *Williams Hematology*, infra, Chapter L33.

As noted above, the amounts and specific activity of the CTI used in the present methods will sometimes vary. However, in most instances the amount or specific activity of the CTI will be sufficient prolong the plasma clotting time by between about 10 seconds to about 3600 seconds or longer when compared to a suitable control. In embodiments in which the PT or other suitable coagulation assay is used, the CTI is preferably capable of reducing or eliminating contact coagulation and prolonging the clot time with about 100 to about 1050 seconds being generally preferred for most applications. See Examples 1–3 below.

As discussed, the present methods can be conducted with a wide-spectrum of TF dependent coagulation assays such as the PT assay or other suitable coagulation assay. In specific embodiments of the invention in which the PT assay or other suitable coagulation assay is used, the amounts of TF used to initiate coagulation and the amounts of calcium used to recalcify plasma will vary depending on intended use. However, in many cases, the amount of added TF will be about 1 nM (TF) or less and between about 2 to about 30 mM calcium added as a suitable salt and particularly calcium chloride. Specifically preferred coagulation assays are described in the examples below.

In one embodiment, the methods involve adding plasma and particularly platelet-deficient plasma to reaction vessels (e.g., plastic or other suitable types vessels such as silanized glass tubes) used to conduct the assays. In this embodiment, the reaction vessels will typically include a pre-determined amount of CTI and optionally at least one additional anti-coagulant such as a heparinoid (ie, heparin or a heparin-related compound) or a buffered calcium-chelating compound such as salt of citrate, e.g., calcium chloride; ethylenediaminetetraacetic acid (EDTA), ethylene glycol-bis(P-aminoethyl ether) (EGTA), acid citrate dextrose, and citrate phosphate dextrose. Other recognized anti-coagulants may also be used as needed. In a specific embodiment, between about 0.05 to about 0.5 mg/ml CTI is used and between about 0.1 and 0.4% (w/v) buffered citrate. See the examples below.

Methods for recalcifying whole blood or blood products such as plasma and particularly platelet-deficient plasma are known in the field. Generally, recalcification involves adding at least a molar excess of a desired calcium salt (preferably buffered) with respect to the added calcium-chelating agent. Typically, an amount of a desired calcium salt such as calcium chloride is added to provide about 2 to about 30 mM calcium and preferably about 5 to about 20 mM calcium. Typically, addition of a suitable amount of calcium chloride or other acceptable calcium salt is preferred. Specific methods for recalcifying plasma are provided in the examples which follow.

Preferred amounts of CTI for reducing or eliminating contact coagulation in a whole blood or a preferred blood product such as plasma and particularly platelet-deficient plasma are between about 50 µg to about 200 µg or greater up to about 500 µg CTI per milliliter of whole blood or blood product with between about 80 to about 100 µg/ml being generally preferred. In most instances, the plasma will be recalcified with a suitable amount of a calcium salt such as calcium chloride. By the term "anti-coagulation effective" is meant an amount of the calcium-chelating agent sufficient to bind any endogenous calcium so that clotting is inhibited and preferably eliminated. Specific methods for making CTI for use with the invention are described in more detail below.

As discussed, preferred assays for measuring plasma clotting times and particularly platelet-deficient plasma clotting times employ suitable coagulation assays such as those disclosed in the examples. Preferred are coagulation assays performed at dilute TF concentrations in which an amount of relipidated TF has been added to initiate extrinsic coagulation. The amount of TF will vary depending on intended use and the extent and rapidity of coagulation desired but will generally be in the range of between about 0.005 to 5 nM TF, and preferably between 0.01 to about 2 nM TF, and more preferably between about 0.05 and 1 nM TF. Additionally preferred assays in accord with the invention will include between about a 500 to about a 2000 fold molar excess of phosphotidylserine (25 mol. %) and phoshotidylcholine (75% mol. %) (PSPC from Sigma, St. Louis, Mo.) in a suitable buffer when compared to the amount of TF used. A particularly preferred buffer is HEPES buffer as described below. Other clotting permissive lipids may be used e.g., PSPC including 0 to about 50 mol. % PS and about 50 to about 100 mol. % PC. Additionally, phosphotidyl glycerol may be substituted for the PS if desired. Preferred methods for making the TF are described below. See Example 9 for particularly preferred methods of making TF.

As noted above, the invention also features methods for storing blood or a blood product at reduced temperature and particularly at freezing or below freezing temperatures. Preferably, the blood or a blood product is contacted with an amount of CTI sufficient to reduce or eliminate coagulation. If the blood or blood plasma is subjected to a clotting permissive temperature, the methods significantly reduce or eliminate contact clotting. An especially preferred method includes at least one and preferably all of the following steps:

a) treating blood with a solution comprising an amount of a buffered citrate salt or other suitable calcium chelating agent sufficient to inhibit the clotting, wherein if plasma is desired, the treated blood is further subjected to conditions conducive to making plasma, b) freezing the treated blood or plasma, c) contacting the frozen blood or plasma with an amount of corn trypsin inhibitor (CTI) sufficient to inhibit the clotting; and d) freezing the CTI-treated blood or plasma, wherein the contact clotting is inhibited if the blood or plasma is subjected to a clotting permissive temperature.

The above-described method is flexible and can be modified as desired to facilitate storage of the blood or blood product. Preferably, the methods are performed under sterile conditions to improve storage and provide for safe patient use. In one embodiment of the method, the blood product is plasma and particularly platelet-deficient plasma. In a more specific embodiment, the buffered citrate salt (or other suitable calcium-chelator) is added to the blood (e.g., at step a)) in an amount between about 0.01%, to about 1% or greater (w/v) of the blood. The percentages of the buffered citrate salt or other suitable calcium-chelating agent will preferably result in a blood concentration of between about 10 mM to about 35 mM.

Preferred amounts of CTI for use in the storage method are generally sufficient to prolong clotting time in recalcified plasma in excess of about 100 to about 1000 seconds, preferably between about 1000 to about 3600 seconds or more. Specifically preferred amounts of CTI are between about 50 to about 200 μg/ml or greater up to about 500 μg/ml up to about 1000 μg/ml with between about 80 to about 100 μg/ml being generally preferred. In embodiments of the method in which plasma is used, the plasma is typically recalcified. If desired, the whole blood or blood product can be tested for coagulation by adding suitable amounts of TF and PSPC as discussed.

Specific freezing temperatures for storing the blood or blood product will vary depending on several parameters such as the length of storage time desired and intended use. However, in most cases, the freezing temperature will be between about −70° C., −80° C., −90° C. to about −100° C. or lower. The clotting permissive temperature will generally be sufficient to initiate detectable clotting in a desired clotting assay such as the PT or other suitable coagulation assay. Typically, the clotting permissive temperature will be between about 4° C. to about 50° C. with room temperature (about 25° C.) to about 37° C. being preferable.

As discussed, the invention also provides novel "point-of care" blood clotting assays that have a wide spectrum of important uses. In one embodiment, the assay involves collecting whole blood from a mammal and especially a human patient and inhibiting coagulation in collected blood by adding an amount of CTI sufficient to inhibit the coagulation. Clotting is preferably initiated with relipidated tissue factor and detected with one or a combination of standard implementations including a Hemochron ACT instrument as described in the Examples. Alternatively, the whole blood can be minimally altered prior to, during or after adding the CTI. The collected blood or minimally altered blood so treated with CTI is preferably used as material for the point of care blood clotting assay. For example, as discussed below, the CTI-treated blood can be used to monitor pharmacological concentrations of an agent in the blood, e.g., an anticoagulant such as an antithrombotic and/or antiplatelet agents. Use of the CTI in accord with this invention provides for more convenient analysis over a more workable time period. As discussed previously, that time period can be many hundreds of seconds, thereby facilitating coagulation analysis and particularly improving sample handling and reducing error. Illustrative agents are specific anticoagulants described in the Examples, e.g., heparin, tick anticoagulant peptide, enoxaprin, and an anti-Factor XI monoclonol antibody termed "abciximab". See Examples 16–19.

The point of care blood clotting assay provides additional advantages. For example, preferred use of the assay enhances monitoring of antithrombotic drugs alone and in combination with antiplatelet agents such as glycoprotein IIb–IIIa inhibitors. Titration of antithrombotic pharmacological agents both individually and in combination will facilitate implementation of therapies such as those that prevent thrombosis and/or preserve hemostasis sufficient to limit bleeding complications.

Further, use of the blood clotting assays provided herein can help to monitor and quantitate (define) additive or synergistic effects of conventional or experimental anticoagulant therapies. Preferred use of the assays will also assist in the identification of optimal dosing regimens of therapeutic agents and help to monitor possible synergistic or adverse effects.

Use of the point of care blood clotting assay is straightforward and should involve minimal investment of time or other resources. In particular, tubes can be prepared in advance and stored after addition of the lipidated tissue factor. Thus, in preferred embodiments blood can be drawn into a vacutairier tube with CTI present (Haematologic Technologies, Essex, Vt.) and added directly to the assay tube. With care taken to prevent introduction of endogenous tissue factor, the assay results are highly reproducible. The consistent lipidation of tissue factor is critical to the success of the assay. To control for potential lot-to-lot variability, a standardization procedure such as that used for the prothrombin time will be useful for many applications. See Palaretti, G. et al. (1987) *Thromb. Haemostas.* 58:905.

Preferred amounts of CTI to use in the point-of-care assay will generally be guided by intended use. However in embodiments in which reduction or inhibition of coagulation is needed from between about 100 to about 1000 seconds, preferably from between about 200 to about 800 seconds, and more preferably about 300 to about 400 seconds, the amount of CTI will generally be between from about 50 μg/ ml to about 500 μg/ ml with about 200 μg/ ml of CTI being preferred for most applications at about room temperature. Methods for measuring coagulation in blood and blood products are known and are discussed in more detail in the Examples below.

As discussed, the point of care blood clotting assays provided by this invention have many advantages. For example, such assays are especially useful for monitoring patient blood in an efficient and highly cost effective manner. In particular, a preferred assay is a simple tissue factor-initiated, contact pathway suppressed, minimally altered whole blood clotting assay with high sensitivity. Preferred use of the assay is sufficient to reflect effects of novel antithrombotic agents which can be applied at the point of care. The assay is highly reproducible with a coefficient of variation between individuals of less than about 10%. As also discussed, the assay has a wide range of uses including detecting and defining antithrombotic effects of hirudin and rTAP with increased sensitivity. The assay can also be used to detect antithrombotic effects of co-factor dependent anticoagulants such as enoxaparin and heparin. Significantly, the assay characterizes clotting in whole blood, thereby allowing analysis of additive and synergistic effects of antithrombotic or antiplatelet agents, as well as certain anti-blood Factor monoclonal antibodies. Particularly preferred assays are explained in the following Examples 16–19 below.

The point of care blood clotting assay of this invention has other important uses. For example, the assay can be employed to monitor therapeutic efficacy of more specific antithrombotic and antiplatelet agents such as low molecular weight heparins, direct thrombin inhibitors, and inhibitors of factor Xa, factor VIIa-tissue factor, and glycoprotein IIb-IIIa. For examples of these and other agents see Catella-Lawson F (1997) in Direct Thrombin Inhibitor in *Cardiovascular Disease. Coronary Artery Disease* 1997;8:105; Cohen M., et al. (1997) *N Engl J Med* 337:447; Vlasuk G. et al. (1997) *Am J Cardiol* 80:665; Stanssens P., et al. (1996) *Proc. Natl. Acad. Sci. USA*;93:2149; and Schulman SP. et al. (1996) *Circulation* 94:1083.

Many prior in vitro coagulation assays are insensitive to the effects of many of these agents. Accordingly, optimal monitoring of in vivo efficacy is often limited and therapeutic value of nearly any antithrombotic agent is typically defined by a reduction in clinical events. The present invention avoids these shortcomings by providing a point-of-care assay that provides accurate and highly reliable in vitro surrogate measures for monitoring and quantifying if needed clinical efficacy of a variety of pharmacological agents. These advantages improve patient management, provide for faster and less error prone results and facilitate clinical evaluation of new agents. The limited availability of accurate and sensitive assays often hampers or precludes pilot studies that could accelerate and reduce costs of clinical investigations. The present assays avoid this drawback by providing for good inhibition of blood coagulation and especially contact inhibition.

Significantly, the point-of-care blood clotting assays of this invention are flexible and can be used to monitor individual patients exposed to diverse drug classes such as antithrombotic, antiplatelet and fibrinolytic drugs.

The invention also provides methods for assaying clotting of blood products. Preferred use of the methods involves assaying clotting in plasma by at least one and preferably all of the following steps:
  a) treating blood with a solution comprising an amount of at least one calcium-cheating agent, preferably one calcium-chelating agent, the treating being sufficient to inhibit clotting,
  b) subjecting the blood to conditions conducive to making plasma,
  c) contacting the plasma with an amount of corn trypsin inhibitor (CTI) sufficient to inhibit clotting,
  d) recalcifying the plasma; and
  e) assaying the recalcified plasma.

Preferred use of the method includes assaying clotting in platelet-deficient plasma although other types of plasma as discussed herein can be used. The method is flexible and can be readily modified to suit intended use. For example, step a) of the method can include adding a suitable amount of CTI. It is preferred that the amounts of CTI used in the method be sufficient to prolong clotting time in recalcified plasma in excess of at least 100 to about 1000 seconds, preferably between about 1000 to about 3600 seconds or more. Specifically preferred amounts of CTI are between about 50 to about 200 µg/ml or greater up to about 500 µg/ml up to about 1000 µg/ml with between about 80 to about 100 µg/ml being generally preferred. The plasma is preferably tested for coagulation by adding suitable amounts of TF and PSPC as discussed.

It is possible to determine amounts or specific activity of CTI using certain coagulation assays and particularly the aPTT assay. For example, an amount of CTI can be added to plasma, e.g., citrated plasma or citrated platelet deficient plasma, and clot times can be evaluated by the aPTT assay. The amount of CTI can be determined by comparing the clot time to a control experiment in which a standard curve has been generated with known amounts of CTI. In particular, most aPTT assays exhibit clot times in the range of about 25 to about 43 seconds. In contrast, when about 500 µg/ml CTI is added, the clot time is prolonged in the range of between about 100 to about 150 seconds or more up to about 240 seconds. Accordingly, the aPTT assay provides a convenient method of measuring CTI made by preferred methods discussed below.

The present invention also provides related methods for assaying clotting of blood products that have been subjected to freezing or below freezing conditions. Preferred methods include at least one and preferably all of the following steps:
  a) treating blood with a solution comprising an amount of at least one calcium-cheating agent, preferably one calcium-chelating agent, the treating being sufficient to inhibit clotting,
  b) subjecting the blood to conditions conducive to producing plasma,
  c) freezing the plasma,
  d) contacting the frozen plasma with an amount of corn trypsin inhibitor (CTI) sufficient to inhibit clotting,
  e) thawing the frozen plasma,
  f) recalcifying the thawed plasma; and
  g) assaying the clotting in the plasma.

The method is flexible and can be readily modified to suit intended use. Preferred use of the method includes assaying clotting in platelet-deficient plasma. For example, step a) of the method can include adding CTI if desired. It is preferred that the amounts of CTI used in the method be sufficient to prolong clotting time in excess of at least 100 to about 1000 seconds, preferably between about 1000 to about 3600 seconds or more as determined by a suitable coagulation assay. Specifically preferred amounts of CTI are between about 50 to about 200 µg/ml or greater up to about 500 µg/ml up to about 1000 µg/ml with between about 80 to about 100 µg/ml being generally preferred. The plasma is preferably tested for coagulation by adding suitable amounts of TF and PSPC as discussed.

An especially preferred method for prolonging plasma clotting time are the coagulation assays described below in Examples 1–6.

Further provided are related methods for prolonging plasma clotting time. The methods generally include at least one and preferably all of the following steps:
  a) treating blood with a solution comprising an anti-coagulation effective amount of corn trypsin inhibitor (CTI) and a calcium-cheating agent,
  b) subjecting the blood to conditions conducive to producing plasma,
  c) recalcifying the plasma; and
  d) assaying the clotting in the recalcified plasma.

Preferred use of the method involves producing platelet-deficient plasma. It is preferred that the amounts of CTI used in the method be sufficient to prolong clotting time in excess of at least 100 to about 1000 seconds, preferably between about 1000 to about 3600 seconds or more as determined by a suitable coagulation assay. Specifically preferred amounts of CTI are between about 50 to about 200 µg/ml or greater up to about 500 µg/ml up to about 1000 µg/ml with between about 80 to about 100 µg/ml being generally preferred. The plasma is preferably tested for coagulation by adding suitable amounts of TF and PSPC as discussed.

See Examples 10–15 below for additionally preferred assays and especially the $X_pPT$ assay in which CTI is used to reduce or inhibit coagulation in blood products such as plasma. The assay is fully compatible with use of a variety of specific plasmas including frozen or previously frozen plasma.

As discussed, the invention is highly flexible and can be readily modified to suit intended use. For example, in some instances it may useful to modify the methods and assays disclosed herein by substituting the CTI with an effective amount of at least one other anticoagulant. Examples include heparin, warfin, recombinant tick anticoagulant (rTAP), huridin, enoxaparin, and an antibody against a blood coagulation factor. A particularly preferred antibody is a monoclonal antibody reactive against blood Factor XI such as the abcixmab antibody described below in Example 19.

In other instances however, it may be more useful to supplement the CTI in the methods and assays with at least one other anticoagulant, e.g., to increase or prolong anti-clotting activity over a desired time period. In this embodiment, the amount of the anticoagulant to use will be guided by intended use but will generally be sufficient to substantially reduce or block coagulation as determined by the standard assays disclosed herein. See also Williams Hematology, supra, at Chapter L33. Particular coagulation assays are disclosed in the Examples including specific plasma (e.g., aPTT, XpPT assays), blood clotting assays, and coagulation as detected by the Hemochron ACT instrument.

In embodiments of the invention in which the assays or methods described herein in which the coagulation factor used is a suitable antibody against a blood coagulation factor and particularly blood Factor XI, the amount of that antibody to use will depend in most instances on parameters such as the amount of anticoagulation activity needed and the duration of activity required. In particular, when the antibody is the abcixmab antibody described below in Example 19, the amount of antibody to use will generally be in the range of between from about 0.001 U/ml to about 10 U/ml, preferably between from about 0.01 U/ml to about 1U/ml with about 0.01 to 0.05 U/ml being preferred for most applications. Unit definitions are those used by a preferred manufacturer (Eli Lilly). Alternatively, the abcixmab can be added to a particular sample in an amount sufficient to inhibit coagulation, ie., between from about 0.1 µg/ml to about 30 µg/ml, preferably between from about 1 µg/ml to about 10 µg/ml, with about 3 to 5 µg/ml being preferred for many applications.

By the term "specific binding" or similar term is meant a molecule and particularly an antibody or fragment thereof as disclosed herein which binds another molecule, typically a ligand, to form a specific binding pair. That specific binding pair does not recognize and bind to other molecules as determined by, e.g., Western blotting, ELISA, RIA, gel mobility shaft assay, enzyme immunoassay, competitive assays, saturation assays or other suitable protein binding assays known in the field.

As discussed, whole blood, minimally altered blood, or a blood product for use with the present invention is suitably drawn from a mammal an especially a human patient. In embodiments in which material is taken from the human patient, that patient can be normal as that term is defined herein. Alternatively, that patient may be suffering from or suspected of having one or a combination of thrombolytic or fibrinolytic disorders known in the field. More particular patients suitable for providing the blood or blood product have or are suspected of having a platelet deficiency or abnormality such as thrombocytopenia.

The following specific examples are illustrative of the present invention.

EXAMPLE 1

Plasma Purification with Added Corn Trypsin Inhibitor (CTI)

The following describes a method for the direct collection of plasma into contact inhibitor solutions comprising CTI (Method A). The procedure was typically employed to collect plasma from normal donors (PT=10–14 seconds, aPTT=26–40 seconds, and normal fibrinogen levels).

Blood was drawn through a sterile Vacutainer brand butterfly needle (19 ga., ¾ in. needle with 12 in. tubing and Luer adapter, Becton-Dickinson and Co., Rutherford, N.J., product #4919) into a sterile 30 cc syringe (product # 309662, Becton-Dickinson and Co.) containing a solution of 3 mg corn trypsin inhibitor in 330 mM sodium citrate (pH 6.5). The citrated blood with the contact inhibitor included was transferred into 50 mL conical tubes (Falcon brand # 2070). Following centrifugation at 980 rpm in a Beckman model TJ-6 centrifuge (rotor model 792) for 30 min (4° C.), the supernatant plasma was aliquotted (1 mL each) into 1.7 mL non-stick conical centrifuge tubes with caps (VWR; West Chester, Pa.; product # 20170-650) for subsequent immediate use or storage at −80° C. Prior to use in the assays, platelet poor plasma is further isolated by centrifugation in an Eppendorf model 5415 C bench top microcentrifluge (14,000 rpm; 10 minutes; standard rotor model F-45-18-11, 25° C.), and the top two-thirds (~0.7 mL) is placed in a separate 1.7 mL conical microcentrifluge tube (as above). Platelet poor plasma can be stored at 1°–4° C. until used in the assay (<2 hrs., 4° C.).

The example illustrates a method by which CTI can be added to whole blood prior to plasma purification. On recalcification of plasma made by the method, clot times in the absence of any inhibitor is in excess of about 2000 seconds or greater.

EXAMPLE 2

Corn Trypsin Inhibitor (CTI) Inhibits Plasma Clotting

The following describes a method for addition of CTI after plasma has been collected (Method B). The procedure was, routinely employed for samples drawn from patients. The workup was performed within the Hematology Laboratory at Fletcher-Allen Health Care in Burlington, Vt.

Blood was drawn directly into sterile buffered 3.8% sodium citrate tubes (Vacutainer brand, product # L10318-00, Becton-Dickinson and Co.), and the tubes were centrifuged at 4227 RCF for 3 minutes (Baxter Stat 60 bench top centrifuge). The supernatant was decanted and an automated PT was established for each patient sample. Platelet poor samples were isolated by further centrifugation for 10 minutes at 14,000 rpm, and the top two-thirds of the plasma was transferred to a Sarstedt rectic cup where it was stored for subsequent analysis at −80° C. Prior to thawing, CTI (stock concentration 1–5 mg/mL) was layered onto the frozen sample in an amount sufficient to give a final concentration of 100 µg CTI/mL plasma. Such citrated plasma containing CTI was used within 0–2 hours (stored at 2–8° C.).

The example illustrates a method by which CTI may be added to blood plasma.

EXAMPLE 3

Plasma Clotting Assay Using Corn Trypsin Inhibitor (CTI)

Platelet poor plasma collected as described in Example 1 or 2 from either patients or normal donors, was delivered (100 μL) into a 12×75 mm disposable polystryrene tube (VWR Scientific, product #60818-361). Calcium chloride (10 μL, 300 mM $CaCl_2$) was added, followed immediately by an amount of concentrated PSPC (prepared as described above, typical stock concentration ~1–5 mM in HBS, pH 7.4) so that the final concentration of lipid in the mixture was 50 nM. To initiate the reaction at zero time, 20 μL of stock tissue factor reagent (described below) was added to a final TF concentration of 1 nM. The tube was rocked in a 37° C. bath until a clot was observed, at which point the time was noted.

EXAMPLE 4

Sensitivity of the Plasma Clotting Assay Using Corn Trypsin Inhibitor (CTI) To Blood Coagulation Factor Deficiency Under the conditions of dilute TF used in the plasma clotting assay (Example 3), it was important to establish whether the assay is responsive to deficiencies in Factor VIII or Factor IX. Therefore, plasma from Factor IX deficient patients (<1% factor IX, George King Biomedical, made platelet poor as in method described in Example 2 with 100 μg/mL CTI) was shown to clot under the present conditions within 113–130 seconds, while normal plasma (isolated by the method of Example 1 with 100 μg/mL CTI) clots between 60–75 seconds. Similarly, plasma from Factor VIII deficient plasma (<1% factor VIII, George King Biomedical, made platelet poor as in Method B with 100 μg/mL CTI) clotted between 125–140 seconds.

In both cases the prolongation in clotting time from the normal was approximately twofold. In contrast, manual PTs for all three cases did not deviate significantly, and were found to be in the normal range for this test (normal plasma, method A=14.7 seconds; Factor IX deficient plasma, method B,=14.8 seconds; and Factor VIII deficient plasma=15.0 seconds). Therefore, the present example indicates that the assay described in Example 3 reflects deficiencies in factor VIII and factor IX better than the traditional PT assay, and is therefore a more biologically and clinically relevant assay than the PT at high TF. Citrated normal plasma that had been recalcified as in Example 3 above did not clot without TF addition even after 3600 seconds.

EXAMPLE 5

Monitoring Plasma Coagulation in Patients Receiving Anti-Coagulant Therapy

The plasma clotting assay described above in Example 3 can be generally employed to monitor patient blood and particularly to measure blood coagulation in patients receiving anticoagulant therapy. For example, the plasma clotting assay can be used to effectively and reproducibly monitor clotting in patients receiving one or more recognized anti-coagulants, e.g., heparin or an oral anti-coagulant such as warfarin, dicumarol or coumadin. See A. G. Gilman et al. supra for examples of other known anti-coagulants.

For many applications, it is useful to standardize the PT assay to an accepted thromboplastin standard. While a laboratory standard thromboplastin is available (WHO standard thromboplastin), laboratories typically do not always use this reagent in the PT assay. Instead, a value for the PT is first determined for a given patient using a commercial thromboplastin reagent calibrated against the WHO standard. This PT data is then used to compute the ratio of the patient PT to the geometric mean from a range of normal control PT values (N>20). From this PT ratio, an International Normalized Ratio (INR) is obtained by raising the PT ratio to the power of the ISI value that is reported for the thromboplastin reagent in use. Using the foregoing approach, the INR can then be reported for a given patient as a measure of the relative reactivity of patient versus normal plasma in the PT assay that would be obtained if WHO standard thromboplastin reagent was used in the procedure. See e.g., Miletich, J P (1995) in *Prothrombin Time* (Chapter L33) in *Williams Hematology*, 5th Ed. (Beutler, E. et al. Eds.) McGraw-Hill, Inc., Health Professions Div., New York, pages L82–L84.

To examine the relationship between the plasma clotting assay described above in Example 3 and the INR obtained for a series of patient plasmas, plasma from patients on stabilized coumadin therapy (with INRs ranging from 1.7–5.5) were obtained through Flecher-Allen Health Care (Burlington, Vt.). These plasmas have extended clot times versus normal. For example, the current assay shows that plasma from normal patients (with an INR.=1) yields clot times ranging from 60–75 seconds. A patient with an INR of 2.0 typically yields clot times in the range of 215–240 seconds while patients with an INR of 5.0 have clot times between 700–800 seconds.

FIG. 1 shows a near linear relationship between clot times as determined in the current assay and the INR established by a normalized PT assay. The data exhibit a high degree of linearity over the INR. range between 1.0 and 5.5, which includes even the most stringent level of anticoagulant therapy that might be clinically employed. Therefore, the plasma clotting assay described in Example 3 is capable of effectively and reproducibly detecting differences in coagulation between normal individuals and patients receiving coumadin therapy. More specifically, the plasma clotting assay is surprisingly responsive to the contribution of the later portion of the intrinsic pathway in both normal and patient plasma.

The following Examples 6–9 demonstrate that at low tissue factor (~25 pM) clotting in whole blood is dependent on factor VIII, and that in plasma a dependence on factor XI can be documented between 25 pM TF and ~5 pM TF. Similar observations to the factor VIII-deficient case have also been made in factor IX-deficient whole blood.

EXAMPLE 6

Clotting in Factor XI Deficient Plasma as a Function of TF

Figure 3:
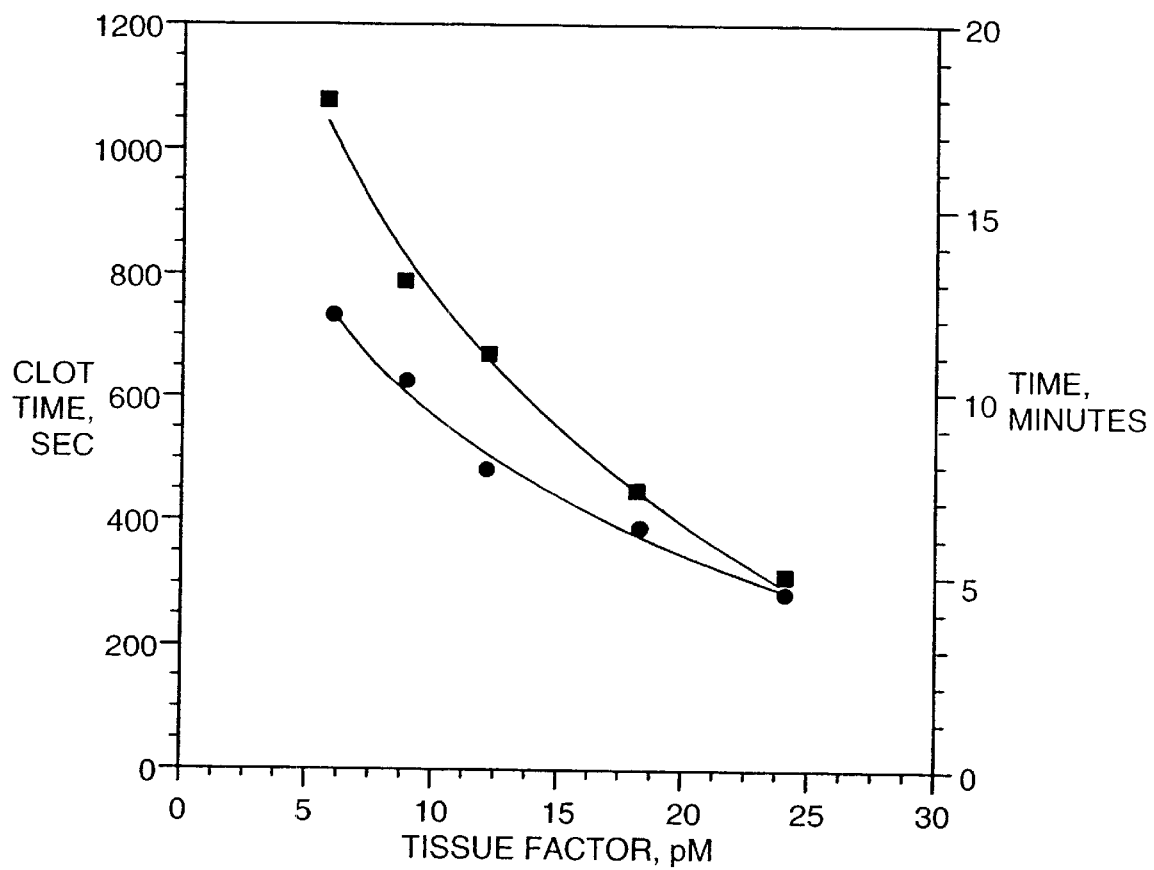
FIG. 3 is a graph showing clotting in Factor XI-deficient plasma as a function of TF and Factor XI.

Von dem Borne, P. A. K. et al. (1995) *Blood* 86: 3035, showed an effect of factor XI on fibrin formation in Factor XII deficient plasma at very low thromboplastin concentrations. Using decreasing concentrations of relipidated tissue factor, a similar dependence on factor XI was demonstrated for clotting in factor XI deficient plasma, measured with suppression of contact activation in the presence of corn trypsin inhibitor (FIG. 3). Clot times with (filled circles) and without (filled squares) factor XI lie along curves that intersect near 24 pM TF, but diverge at concentrations of TF below 24 pM. Clotting at 24 pM is 28 seconds slower without factor XI, whereas by 6 pM TF, the difference reaches 5.7 minutes. Based upon these observations, blood coagulation in hemophilia C was investigated at 25 and 5 pM.

FIG. 3 is explained as follows: clot time in factor XI deficient plasma (<1%) was measured as a function of tissue factor and factor X (as described in Methods). The ordinate is shown in seconds (left-hand axis) and minutes (right-hand axis). Two curves are presented: one for factor XI deficient plasma without factor XI replacement (<1%, filled squares) and a second curve for the same plasma with 1 U/mL factor XI (25 nM, filled circles). To connect the data, smooth curves were drawn which meet near 24 pM TF. The curves become increasingly divergent as tissue factor concentration is reduced to 6 pM TF, where the difference is most pronounced.

Example 6 shows that conditions of Examples 4 and 5 can be further modified by reducing TF concentration to make the assay more sensitive to Factor XI.

EXAMPLE 7

Blood Coagulation in Hemophilia A

Figure 2A:
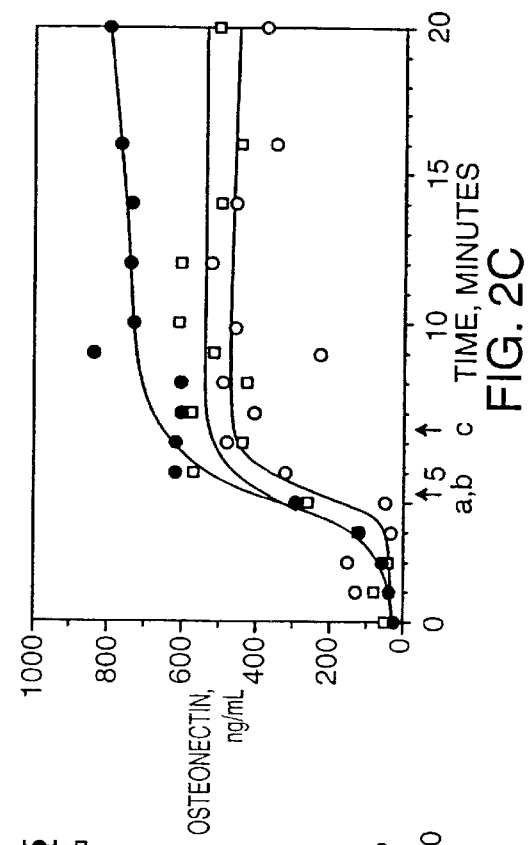
FIGS. 2A–D are graphs showing coagulation and normal and hemophilia A blood with and without replacement.

Coagulation in blood from a patient with severe hemophilia A (<0.5% VIII:C) was compared to coagulation in blood from normal donors following initiation with 25 pM TF (FIGS. 2A–D). Depicted in FIG. 2A are the time courses for TAT generation in normal and factor VIII deficient blood, with and without factor VIII replacement. The normal profile (filled circles) is constructed from averaged data ("s.e.m.") from a series of 14 experiments conducted over a period of 18 months with 4 normal subjects. Little TAT is detected throughout the initiation phase; subsequently, the bulk of the TAT produced is generated explosively (54.6 nM/min) during the propagation phase after clot time (4.0+/−0.2 minutes, arrow a). In factor VIII deficient blood (open circles), clot time is delayed until 6.5 min (arrow c), representing an increase in the initiation phase of approximately 60% over the normal case. The explosive thrombin generation ordinarily observed in normal blood after clot time is greatly depressed (maximum rate 1.9 nM/min, 4% of normal). Replacement with recombinant factor VIII (open squares, 1 U/mL) shortened the clot time (4.1 minutes, arrow b) and increased TAT formation to 45.9 nM/min between 5 and 16 minutes.

Figure 2B:
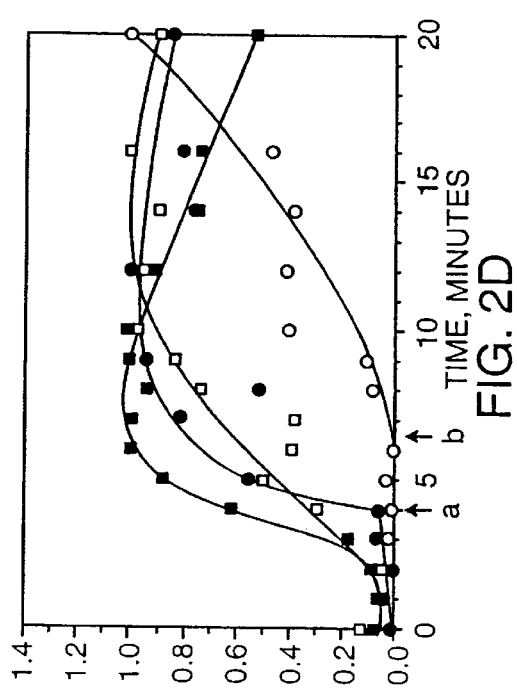
Figure 2C:
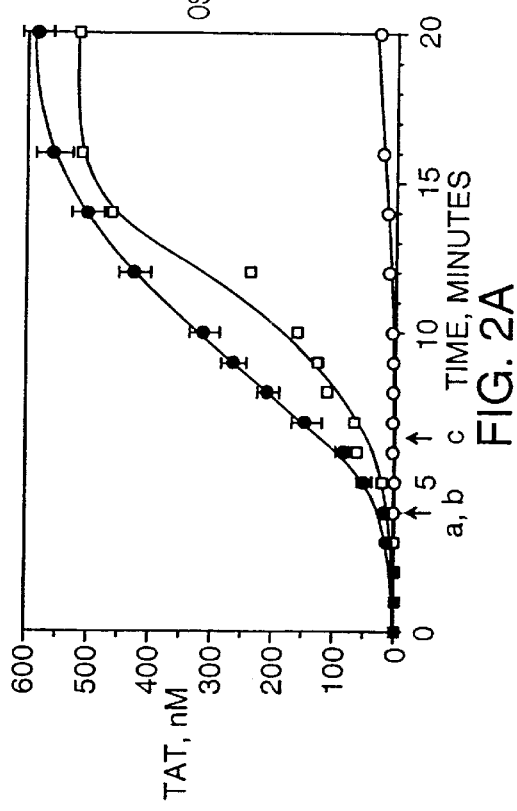

Progress curves for FPA release in these experiments is given in FIG. 2B. The normal profile (filled circles) is the average of a series of 9 experiments on two individuals. FPA is liberated at a maximum rate of 5.2 $\mu$M/min (between 4 and 6 minutes), with about 4.8 $\mu$M (30% maximum) observed at clot time (arrow a). In factor VIII deficiency (open circles) the maximum rate of FPA release is reduced to 1.6 $\mu$M/min (30% of normal). However, fibrinopeptide A production is nearly quantitative by the end of the experiment (20 minutes). The extent of FPA release in the hemophilic case at clot time (arrow c) is the same as in the normal profile (approximately 30% maximum). Replacement of factor VII (open squares) increases the maximum FPA rate to 6.4 $\mu$M/min, in excess of the normal rate by 23%. At clot time the extent of FPA release is 35% (7.4 $\mu$M), similar to the estimates from normal and factor VIII deficient blood.

Profiles for osteonectin release as a measure of platelet activation (Stenner, D. D., et al. (1986) Proc Nat Acad Sci. (USA) 83: 6892 and Kelm, R. J. Jr. and Mann, K. G. (1990) Blood 75: 1105) are given in FIG. 2C. In the blood of a normal individual (filled circles, contemporaneous control), osteonectin release is approximately 50% by clot time (arrow a) and is complete by 5 minutes. In factor VIII deficient blood (open circles), the progress curve is slightly delayed versus normal. Complete osteonectin release is observed by 6 minutes, reaching maximum levels prior to clot time (6.5 minutes, arrow c). A curve similar to the control was obtained when factor VIII was replaced in the deficient blood (open squares). The similarity of these profiles indicates that platelet activation at 25 pM TF is only slightly affected by the absence factor VIII.

Figure 2D:
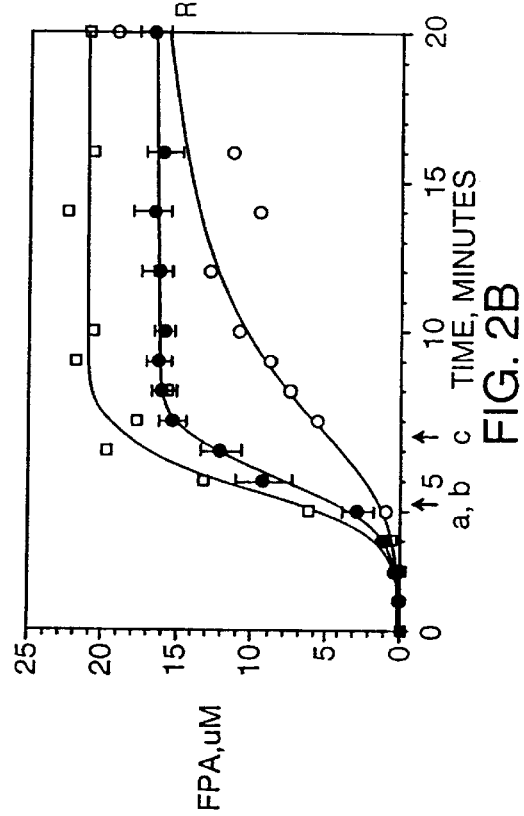

Time courses for factor $Va^{HC}$ generation in hemophilia A blood are shown in FIG. 2D with and without factor VIII replacement. When factor VIII is present (filled squares), significant generation of factor $Va^{HC}$ begins at 3 minutes and is complete by 6 minutes. In the absence of factor VIII (open squares), generation of factor $Va^{HC}$ is slowed and does not reach a maximum until 12 minutes. At clot time in each experiment, approximately 60–65% of the heavy chain is generated. When factor VIII is present, formation of the light chain (LC, filled circles, FIG. 2D) is first detected at clot time (4.1 minutes, arrow a) and is complete at 6 minutes. In contrast, factor $Va^{LC}$ generation is dramatically delayed in factor VIII deficient blood (open circles), with traces observed at 8 minutes and rapid generation after 9 minutes. Thus, LC production, the limiting step in expression of factor Va cofactor activity (Rand, M. D., et al. (1996) Blood 88: 3432 and van't Veer C. et al. (1997) J. Biol. Chem. 272: 7983 ) is significantly delayed in the absence of factor VIII.

The impaired factor V activation is probably a significant factor limiting prothrombin conversion in hemophiliacs. In normal blood Rand, M. D., et al. (1996) supra during the propagation phase of thrombin generation, prothrombinase concentrations have been estimated from TAT generation rates as 7 pM at clot time increasing to a maximum of 150 pM three minutes later Rand, M. D., et al. (1996) supra. Factor Xa was observed to be the limiting component of prothrombinase, since factor Va levels and platelet activation could be demonstrated at concentrations in excess of 150 pM. In the present study, using TAT data for the normal case, approximately 35 pM prothrombinase is calculated at clot time, which increases to a maximum of 106 pM by 12 minutes into the reaction; estimates in hemophilic blood with factor VIII replacement were similar (19 pM at clot time, 136 pM at maximum). However, in factor VIII deficient blood, approximately 1 pM prothrombinase was indicated at clot time and did not exceed 6 pM throughout the experiment. Therefore, limiting factor Xa is generated in hemophilia A, and its incorporation into prothrombinase will be slow as a result of delayed generation of factor Va. Free factor Xa is a less efficient enzyme for prothrombin conversion Mann, K. G., et al. (1990) Blood. 76: 1 and Mann, K. G., et al. (1992) Seminars in Hematology 29: 213 and lacks the relative protection against inactivation by AT-III and TFPI that factor Va provides in the prothrombinase complex. See Marciniak, E. (1973) Br J Haematol. 24: 391 and Mast, A. E. and Broze, G. J. (1996) Blood 87: 1845.

The present example indicates that when compared with normal coagulation at 25 pM TF coagulation in factor VIII deficient blood is characterized by modest lengthening of the clot time. Therefore, the sensitivity to Factor VIII is maintained under these conditions. In addition, detailed studies in Factor VIII deficient blood shows slowed FPA release, and major reductions in the rates of formation of factor Va, factor Xa and thrombin. Related experiments have been preformed with Factor IX.

FIG. 2 is explained as follows:

Using 25 pM TF, coagulation was initiated in normal and hemophilia A blood (see Methods and Rand, M. D., et al. (1996) supra, with and without factor VIII replacement (1 U/mL blood). Smooth curves have been drawn by hand through the points to approximate the data. A. Time courses for TAT in normal blood (filled circles), hemophilia A blood (open circles), and hemophilia A blood with factor VIII replacement (open squares). Each point on the normal curve represents an average TAT from 14 experiments on 4 normal subjects (with error bars, s.e.m.). Average clot time for the composite normal curve is 4.0+/−0.2 minutes (arrow a). Clotting in factor VIII deficient blood occurred at 6.5 minutes (arrow c) which was shortened to 4.1 minutes with factor VIII replacement (arrow b); a control tube without TF in the factor VIII deficient experiment did not clot (>20.6 min.), and the replacement control clotted at 17.8 minutes. B. FPA generation in normal blood, factor VIII deficient blood, and factor VIII deficient blood with replacement (symbols as in panel A). The normal curve represents the averaged results from 9 experiments performed on two individuals, with error bars (s.e.m.). The average clot time for the normal profile was 4.1+/−0.2 (standard error of the mean, s.e.m.) minutes (arrow a), with the other clot times as in panel A. C. Osteonectin release was measured to examine platelet activation (symbols as in panel A). The normal curve is constructed from blood taken from a single normal donor (clot time=4.1 minutes, arrow a), drawn contemporaneously with the factor VIII deficient patient. Other clot times and symbols are as in panel A. D. Following analysis of factor V activation by immunoblotting, profiles were constructed by densitometric analysis as in Methods. Time courses are given for formation of the heavy (squares) and light chains (circles) of factor Va (factor $Va^{HC}$ and $Va^{LC}$), with (closed symbols) and without (open symbols) factor VIII replacement. For clarity, the normal profile is omitted, but is similar to the profile with factor VIII replacement. Clot times are 4.1 minutes (hemophilia A with factor VIII replacement, arrow a) and 6.5 minutes (hemophilia A, arrow b).

EXAMPLE 8

Coagulation in Factor XI Deficient and Normal Whole Blood at 25 pM TF

Table 1 below reports the clot times for coagulation in factor XI-deficient blood, deficient blood with replacement and normal whole blood initiated at 25 and 5 pM TF with suppression of contact activation by corn trypsin inhibitor. Table I below shows Clot times for experiments in normal and factor XI deficient whole human blood, with controls. Data are given for each of the experiments described in the text, along with phlebotomy control values i(in parentheses) for clotting in the absence of added tissue factor initiator. Where phlebotomy controls exhibited no clotting by the end of the experiment, times are indicated as lower limits (denoted by a "greater-than" symbol). In all experiments, including controls, factor XIIa activity was suppressed by the addition of corn trypsin inhibitor at the level of 48 μg/mL of blood (see Methods for brief description of the experiments). For the experiments with 25 pM initiator, patient A was the donor; in the 5 pM experiments, the donor was patient B.

TABLE I

| | Initiator concentration: | |
|---|---|---|
| Donor: | 25 pmol/L TF | 5 pmol/L TF |
| XI-deficient | 3.5 min. (control, −TF > 20.5 min.) | 15.7 min. (control, −TF > 20.8 min) |
| XI-deficient with replacement | 3.7 min. (control, −TF > 20.3 min.) | 9.7 min. (control, −TF > 20.8 min.) |

TABLE I-continued

| | Initiator concentration: | |
|---|---|---|
| Donor: | 25 pmol/L TF | 5 pmol/L TF |
| Normal | 3.3 min. (control, −TF = 12.1 min) | 11.1. min. (control, −TF = 18.1 min.) |

Figure 4A:
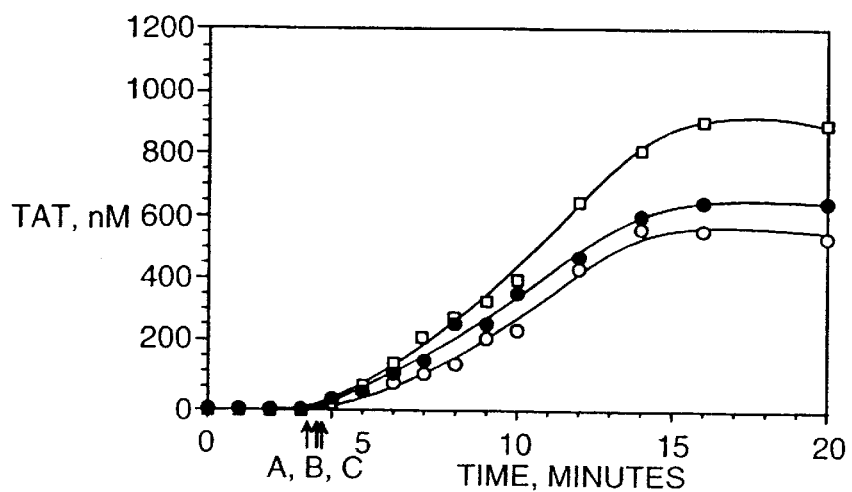
FIGS. 4A–C are graphs showing coagulation and normal and hemophilia C blood at 25 pmol/L initiator with and without replacement.

At 25 pM TF, where deficiency of factor VIII results in impaired clot formation and suppression of the propagation phase of thrombin generation, factor XI deficiency has a negligible effect. Clot time is 3.5 minutes (contemporaneous normal control=3.3 minutes), and is not shortened by factor XI replacement (3.7 minutes). In the control tubes (corn trypsin inhibitor present, no TF added), clotting is significantly prolonged or non-existent, indicating that other sources of initiation contribute negligibly in these experiments. At 25 pM TF, thrombin generation profiles for the normal (filled circles) and factor XI deficient (open circles, patient A) are almost identical, while the profile for factor XI replacement (open squares) exhibits somewhat faster thrombin generation (FIG. 4A). The maximum rates of thrombin generation are nearly identical in the normal (61 nM/min) and factor XI deficient (63 nmol L/min) experiments, and factor XI replacement increased the rate of thrombin generation to 85 nmol L/min. This increase leads to a 65% higher concentration of final TAT in the replacement case (950 nM) than in the deficient case (575 nM). These results indicate that factor XI is not required for explosive thrombin generation in blood initiated with 25 pM, but modestly influenced the rate of thrombin generation after clot formation in this individual.

Figure 4B:
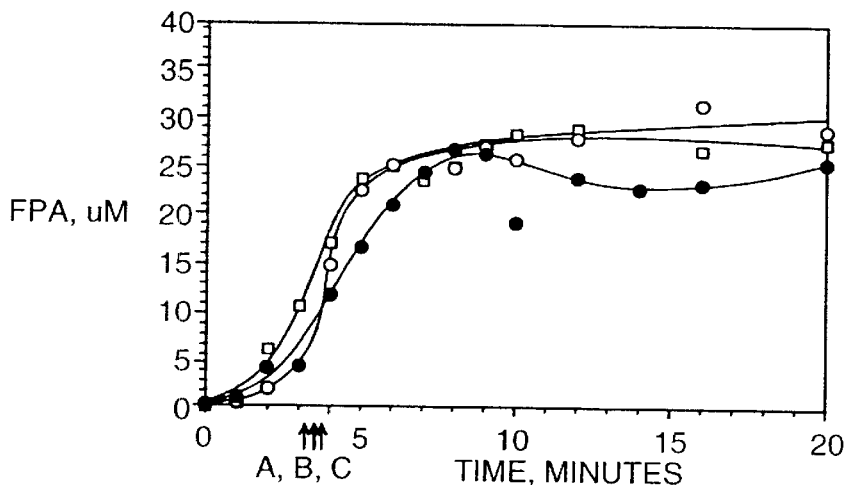

FIG. 4B shows the FPA profiles obtained at 25 pM TF. For each case, the reaction progress occurs over similar time scales and to similar extents. In factor XI deficient blood (open circles), FPA is released at a maximum rate of 6.1 μM/min (5.6 μM/min in normal blood, filled circles), while replacement of factor XI increased this rate to 7.3 μM/min (open squares). Fibrinogen conversion at clot time was between 30–41% in all cases. In addition, osteonectin release profiles (FIG. 4C) show that platelet activation is not strongly influenced by the presence or absence of factor XI when the reaction is initiated with 25 pM TF. In all cases, the profiles were similar and exhibited maximal release by 5 minutes. Evaluation of factor Va generation in normal and factor XI.deficient blood showed identical activation profiles. Densitometric profiles of the heavy chain and light chain (open symbols, FIG. 5A) show that factor $Va^{HC}$ is detectable within 1 minute of initiation in all reactions, and by clot time approximately 33–45% is observed in each profile. Likewise, the profiles for light chain formation in the factor XI deficient (open triangle), replacement (open square) and normal (open circle) experiments are similar to each other. Levels of factor $Va^{LC}$ are below the limits of detection throughout the initiation phase and only a small fraction is generated at clot time. After clot time, light chain is generated quantitatively within 1–2 minutes (4 and 5 minutes post-initiation). Together, the factor $Va^{HC}$ nd $Va^{LC}$ profiles demonstrate that cofactor activation is unaffected by factor XI.

Example 8 shows that in the assay using 25 pM TF, clotting in whole blood was insensitive to Factor XI.

Figure 4C:
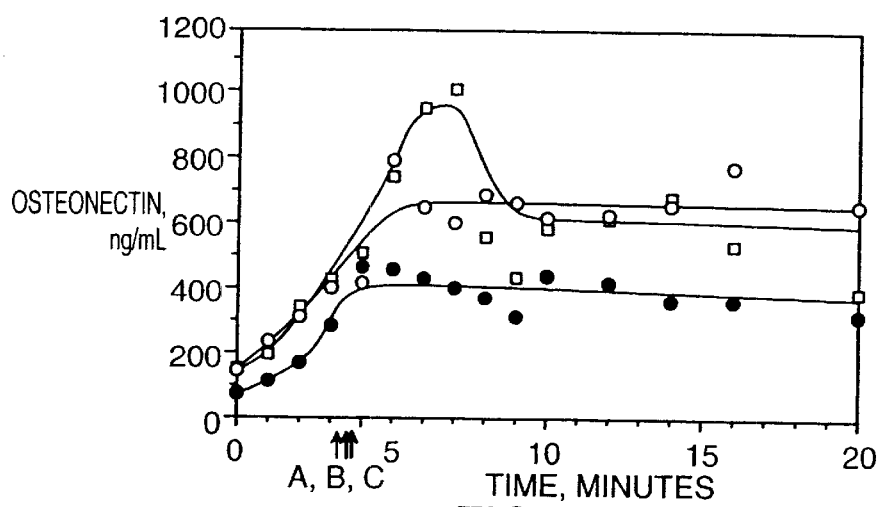

FIGS. 4A–C are explained as follows:

Using 25 pM TF, coagulation was initiated in normal and hemophilia C blood (see Methods; Rand, M. D., et al. supra with and without factor XI replacement (1 U/mL blood). Time courses for TAT are provided (A) following immunoassay analysis of quenched samples from the normal blood (filled circles), hemophilia C blood (open circles), and hemophilia C blood with factor XI replacement (open squares). Clot times for the experiments and control tubes are as given in Table 1, and are denoted by arrows for blood from normal (arrow a), hemophilia C (arrow c) and hemophilia C donors with factor XI replacement (arrow b, 1 U/mL). In addition to TAT, FPA (B), and platelet osteonectin (C) profiles are provided. (Symbols and clot times as in panel A).

Figure 5A:
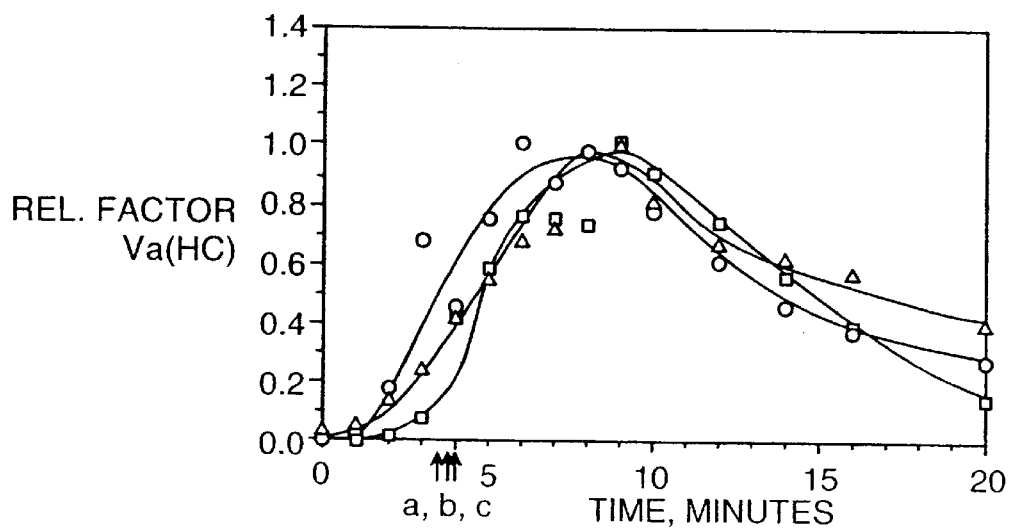
FIGS. 5A and B are graphs showing factor Va generation during coagulation in normal and hemophilia C blood at 25 pmol/L initiator with and without replacement.

FIGS. 5A and B are explained as follows. The graphs show Factor Va generation during coagulation in normal and hemophilia C blood at 25 pmol/L initiator, with and without replacement. For experiments described in FIG. 4, analysis of Factor V activation was performed by immunoblotting. Profiles following Factor Va heavy chain (A) and light chain (B) were constructed by densitometric analysis as described below. Time courses are given for formation of the heavy and light chains in normal blood (open circles) and hemophilia C blood (patient C1), with (open squares) and without (open triangles) Factor XI replacement. Clot times are as in Table 1 and FIG. 4, and curves have been drawn through the points by hand.

EXAMPLE 9

Coagulation in Factor XI Deficient and Normal Blood at 5 pM TF

Coagulation in normal and factor XI deficient blood following initiation at 5 pM TF are summarized in table 1 and FIG. 4 (patient B). Confirmation of the data has been obtained in a separate experiment with a third factor XI deficient individual. Clotting in factor XI deficient blood at 5 pM initiator (15.7 minutes, table 1) was delayed 4.6 minutes relative to normal (11.1 minutes, contemporaneous donor). Factor XI replacement shortened the clot time in hemophilia C blood by 6 minutes (9.7 minutes), in agreement with the predictions of the plasma assay (FIG. 3). In the absence of TF (corn trypsin inhibitor only), the controls for hemophilia C did not clot, with or without factor XI replacement (over 20.5 minutes), confirming that factor XIa contamination was not significant in the factor XI preparations.

Figure 6A:
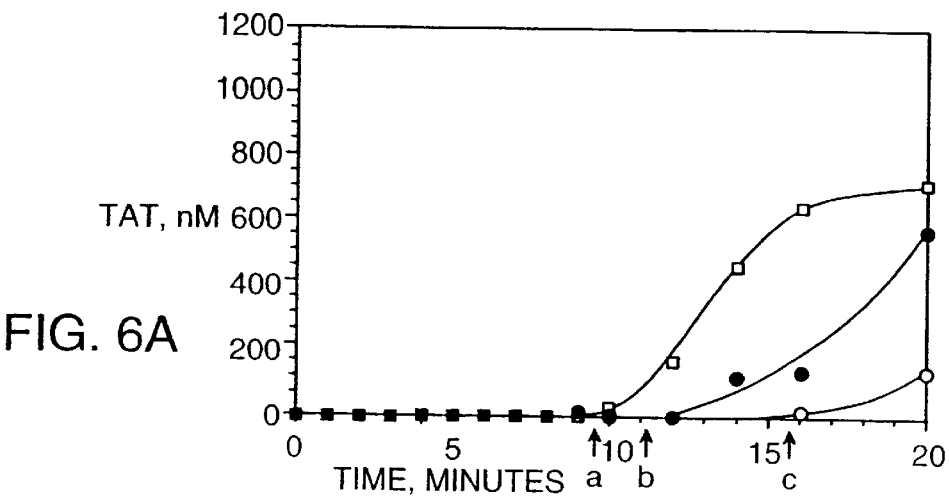
FIG. 6A–C are graphs showing coagulation in normal and hemophilia C blood at 5 pmol/L initiator with and without replacement.

In the TAT profiles of FIG. 6A, the bulk of the thrombin is formed after clot time, and factor XI replacement increases the rate of thrombin generation during the propagation phase in hemophilia C blood. In normal blood (filled circles, FIG. 6A), TAT is generated at 110 nM/min after clot time (arrow b), compared with ~37 nM/min after clot time (arrow c) in factor XI deficient blood (open circles). Factor XI replacement (open squares) increases the TAT rate to 119 nM/min at clot time (arrow a). The result is that final levels of TAT are higher in the normal and replacement experiments (750 nM and 600 nM), but only reached ~150 nM when the factor XI deficient experiment was terminated. But even at 5 pM TF, thrombin production in hemophilia C blood is in excess of levels observed in hemophilia A blood at 25 pM, consistent with the relative clinical severity of the two congenital diseases.

Figure 6B:
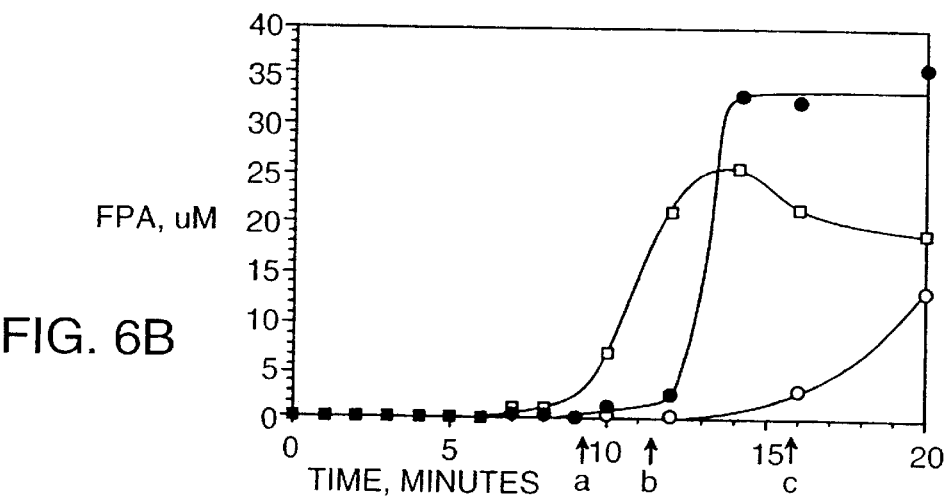

FIG. 6B displays profiles for the release of fibrinopeptide A, which also becomes dependent on factor XI at 5 pM TF. Fibrinopeptide A release occurs more slowly in hemophilia C blood at 5 pM initiator (open squares, maximum rate 2.7 $\mu$M/min) than in normal blood (15.5 $\mu$M/min), and is incomplete by the end of the experimental period. Replacement of factor XI (open squares) increases FPA formation to 7.4 $\mu$M/min, and provides complete fibrinogen conversion within 2–2.5 minutes of clot time.

Platelet activation in blood initiated at 5 pM TF was estimated by osteonectin release (FIG. 6C), and contrasted starkly with the data at higher levels of initiator (FIG. 3C). In factor XI deficient blood (open squares), osteonectin release is very slow during the initiation phase, reaching approximately 65% by clot time (arrow c). During this period, aggregates were noted as grainy accumulations at the walls of the reaction tubes. With factor XI replacement (open squares), osteonectin again increases slowly over the initiation phase reaching 67% by clot time (arrow a); the remaining osteonectin is released within 2 minutes. This was similar to the normal profile (filled circles) in which 42% fluid phase osteonectin is detected at clot time (arrow b) followed by rapid and immediate release of the remaining protein. In general, at 5 pM TF platelet activation is slow and incomplete at clot time (42–67%), associated with limited thrombin generation during the initiation phase. Following clot formation, the observed thrombin burst activates the platelets rapidly, ensuring maximal activation. Thus unlike hemophilias A and C at 25 pM TF, platelet activation at 5 pM TF is significantly influenced by the absence of factor XI.

At 5 pM TF, generation of factor $Va^{HC}$ in hemophilia C blood (FIG. 7A, open triangles) like FPA release and platelet activation, is slower than normal (open circles). The bulk of the heavy chain does not appear until 20 minutes ($\Delta$), whereas in the replacement (open squares) and normal profiles the maximum occurs following clot time in each case near 12 and 15 minutes, respectively. Only small amounts of factor $Va^{HC}$ appear prior to clot formation in these experiments. In contrast, factor $Va^{LC}$ (FIG. 7B) is undetectable until after clot time in all three experiments, and again appears to be the limiting step in cofactor activation. Thus, at 5 pM TF, factor V activation is affected by the presence or absence of factor XI, with the bulk of factor V activation occurring after clot time in each case.

Examples 7–9 provide results of coagulation in hemophilia A and hemophilia C blood. In severe hemophilia A at 25 pM TF, clotting was delayed versus normal (~2.4 minutes), reflecting modestly reduced levels of thrombin during the initiation phase leading to clot formation. See Example 7. A more striking observation was the severely depressed thrombin generation in the propagation phase (after clotting was detected), measuring less than 4% of the normal rate. The impaired thrombin generation was accompanied by a reduced rate of fibrinogen cleavage and drastically delayed factor Va generation. Replacement of factor VIII restored normal clotting and thrombin generation in the propagation phase. These results support earlier observations of reduced prothrombinase activity in the absence of functional intrinsic tenase. Osterud, B. and Rapaport, S. I. (1977) *Proc Natl Acad Sci.* 74: 5260; Lawson, J. H., et al. (1994) *J. Biol Chem.* 269: 23357; Van't Veer, C. and Mann, K. G. (1997) supra; Biggs, R. and Nossel, H. L. (1961) *Thromb Diath Haemorrh.* 6: 1; and Hoffman, M. et al. (1995) *Blood* 86: 1794. In addition, Example 7 shows that reduced thrombin generation in the absence of factor VIII also leads to severely reduced factor Va generation, which further reduces the effectiveness of the limited factor Xa produced during coagulation in hemophilia A.

Although thrombin generation, fibrinogen cleavage, and platelet activation were diminished during coagulation in hemophilia A blood, Examples 8 and 9 show relatively slight delay in platelet activation versus normal (~1 minute). These results are in essential agreement with other studies. See e.g., Hoffman et al. (1995) Blood 86:1794. Platelet activation was found to be largely independent of the intrinsic tenase. Together, the examples show complete platelet activation and slow fibrinogen formation correlate with the description of clotting in the bleeding time wounds of hemophiliacs and where the primary platelet plug is devoid of normal fibrin stabilization, leading to a friable clot which ultimately ruptures. Hovig T, et al. (1968). *Am J Pathol* 53:355, 1968; and Sixma J J, van den Berg A (1984) *Br J Haematol* 58:741.

Examples 8 and 9 also point to a dependence on factor XI when TF concentrations are employed below 25 pM. This indicates that blood contains components to produce biologically sufficient factor XIa activity on a physiologically relevant time scale. In addition, the examples describe not only thrombin generation and fibrin conversion, but also platelet and cofactor (factor V) activation. Further, the examples provide the first results in which platelets and other blood cells are available as the procoagulant surface. Compared with plasma coagulation studies on exogenous lipids (see Examples 3 to 6), these whole blood studies provide for a description of the processes on endogenous blood cells during the coagulation reaction.

Examples 8 and 9 extend these observations to thrombin, factor Va, and platelets in hemophilia C blood. In contrast with the results for hemophilia A at 25 pM TF, coagulation was hardly affected in hemophilia C blood. Clotting was identical in hemophilia C and normal experiments, as was explosive thrombin generation in the propagation phase. Replacement of factor XI modestly increased thrombin generation after clot time, but all other products of the reaction (factor V activation, osteonectin release from activated platelets, and FPA) were unaffected by the presence or absence of factor XI. Reducing the initiator concentration to 5 pM prolongs the initiation phase of hemophilia C blood coagulation by 4.6 minutes versus normal, and factor XI replacement shortens this clot time by nearly 6 minutes.

The results indicate that impaired coagulation in hemophilia C will only occur at lower initiator concentrations than those observed for impaired coagulation in hemophilia A. Furthermore, the results show that in hemophilia C, maximum thrombin generation rates decrease as tissue factor is reduced from 25 pM to 5 pM. However, in normal blood as well as in hemophilia C blood with factor XI replacement, such a decrease in thrombin generation was not observed. In fact, an increase was detected: from 61 and 85 nmol TAT/L/min in the normal and replacement experiments using 25 pM TF, respectively, to 110 and 119 nmol TAT/L/min with 5 pM TF. These observations indicate that factor XI may play an increasingly significant role in supplementing prothrombinase levels as the initiator concentration is reduced.

The results correlate with the clinical severity of the disorders. At 25 pM TF in hemophilia A, clotting and product formation are measurably affected by deficiency of factor VIII. Conversely, factor XI deficiency appears to have little consequence for coagulation at 25 pM TF. Only when initiator concentration falls below 25 pM does the reaction become sensitive to the presence of factor XI. But even at 5 pM TF, thrombin generation is not ablated, as in factor VIII deficiency at 25 pM TF, consistent with the clinical observation that hemophilia C is a less severe disease than hemophilia A.

Figure 6C:
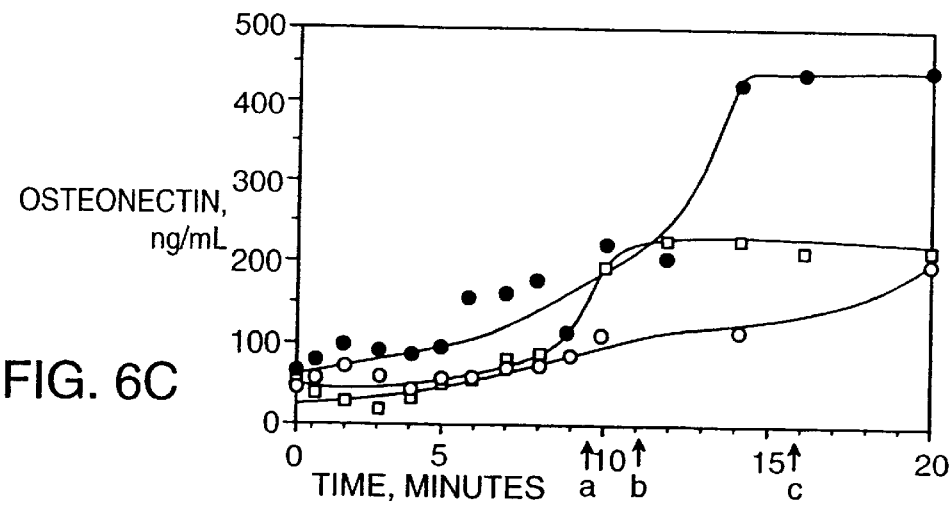

FIGS. 6A–C are explained as follows: Using 5 pM TF, coagulation was initiated in normal and hemophilia C blood (see Methods; Rand, M. D., et al. (1996), supra with and without factor XI replacement (1 U/mL blood). Time courses for TAT are provided (A) following immunoassay analysis of quenched samples from the normal blood (filled circles), hemophilia C blood (open circles), and hemophilia C blood with factor XI replacement (open squares). Clot times for the experiments and control tubes are as given in Table 1, and are denoted by arrows for blood from normal (arrow a), hemophilia C (arrow c) and hemophilia C donors with factor X replacement (arrow b, 1 U/mL). In addition to TAT, FPA (B), and platelet osteonectin (C) profiles are provided. (Symbols and clot times as in panel A).

Figure 5B:
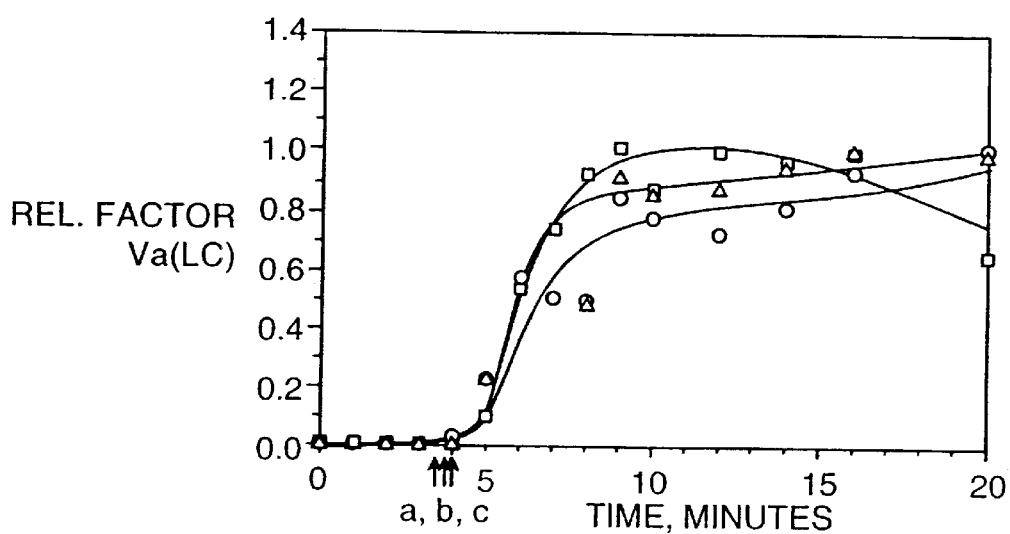
Figure 7A:
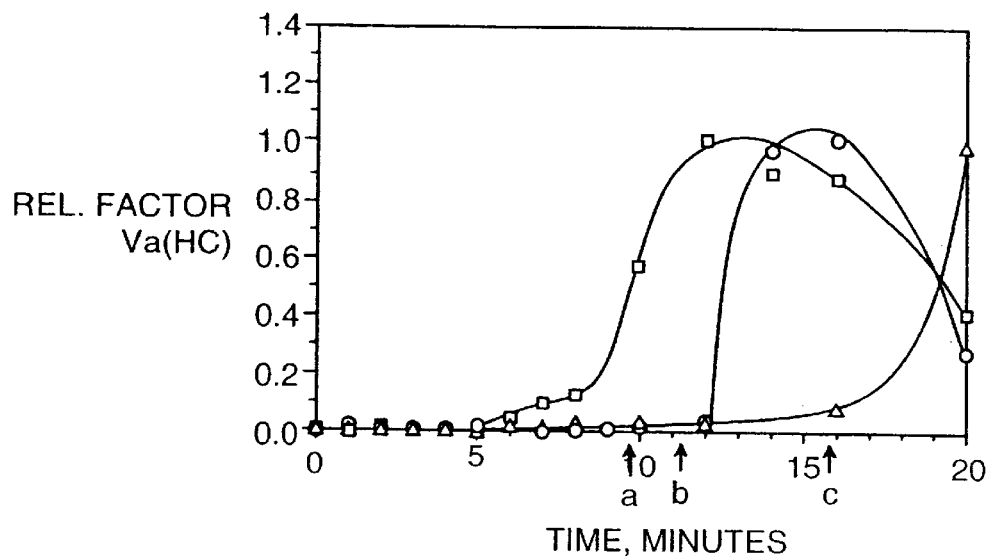
FIG. 7A and B are graphs showing factor Va generation during coagulation in normal and hemophilia C blood at 5 pmol/L initiator With and without replacement.
Figure 7B:
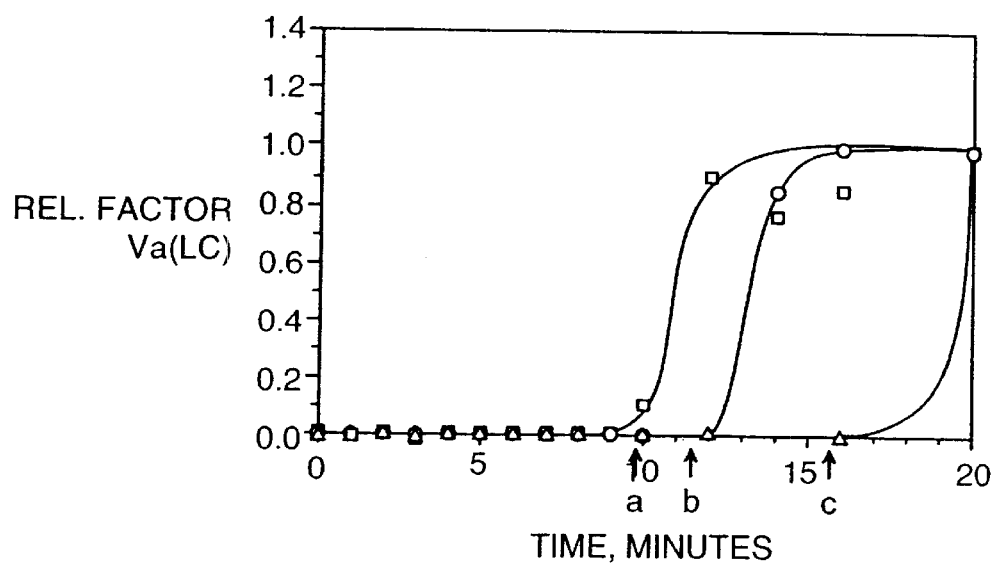

FIGS. 7A and B are explained as follows: The graphs show Factor Va generation during coagulation in normal and hemophilia C blood at 5 pmol/L initiator, with and without replacement. For the experiments described in FIG. 6, analysis of factor V activation was performed by immunoblotting. Profiles following factor Va heavy chain (A) and light chain (B) were constructed by densitometric analysis as discussed below. Time courses are given for formation of the heavy and light chains in normal blood (open circles) and hemophilia C blood (patient C2), with (open squares) and without (open triangles) factor XI replacement. Clot times are as in Table 1 and FIG. 5, and curves have been drawn through the points by hand.

Example 9 shows that while the assay is performed at a concentrations of TF (25 pM) it is not sensitive to Factor XI.

The following materials and methods were used in Examples 1–9 as needed:

1. Preparation of tissue factor/lipid reagent:
    Recombinant human tissue factor (Baxter-Hyland Health Care, lot no.HY8003) in 1.2% v/v octyl β-D-glucoside was relipidated into small unilammelar vesicles of PSPC (25 mol % PS/75 mol % PC, 10 μM total lipid) in HBS (HEPES, 20 mM; NaCl, 150 mM; pH 7.4) plus calcium (2 mM) for 30 minutes at 37° C. Concentrated sucrose (60% w/v) was subsequently added to the relipidation mixture to 10% final in order to stabilize the vesicles for long-term freezer storage (up to 12 months). Aliquots of the reagent (200 μL) were lyophilized and stored at −20° C., which were rehydrated 60 minutes before each experiment and used with reproducible results. See Barenholz, Y. et al. (1997) *Biochem.* 16: 2806; and Lawson, J. H et al. (1994) *J. Biol. Chem.* 269: 23357.

2. Prothrombin time (PT) and Activated Partial thromboplastin time (aPTT) assays:
    Automated PT or automated aPTT assays were performed on patient or normal plasma (100 μL) in the Hematology Laboratory at Fletcher-Allen using either an ACL Futura coagulometer (Instrumentation Laboratories), or a model ST4 automated coagulometer (Diagnostic Stago), according to the recommendations of the manufacturers.
    For the manual PT method, 100 μL of citrated test plasma was pre-warmed at 37° C. for 30 seconds. The reaction was initiated at zero time with 200 μL of Simplastin Excel (product # 52001, Organon Teknika, Durham, N.C.), and the sample was rocked in a 37° C. bath until a clot was observed, at which point the time was noted. Manual aPTT assays were performed in plastic tubes (VW Scientific, no. 60818-270) on 100 μL samples of fresh frozen, citrated human plasma using the manual "tilt-tube" approach described by the manufacturer of the PT or aPTT reagent. When testing the effect of buffer or antibody, no more than 5 μL of the additive was mixed with 95 μL of plasma, to minimize dilution errors.

3. Assaying contact inhibitor activity

Activity of contact pathway inhibitors used in these experiments was estimated by the prolongation of the aPTT in normal plasma upon addition of the reagent. The activated partial thromboplastin (aPTT) assay was performed manually on test plasma containing 90 μL of pooled normal citrated plasma (FACT standard plasma, George King Biomedical, Highland Park, Kan.) with 10 μL of either buffer or test solution (such as corn trypsin inhibitor extract), following the instructions provided by the manufacturer of the aPTT reagent (Automated APTT reagent, manual method, product # 35513, Organon Teknika Corp., Durham, N.C.). Incubation of the test plasma with the automated APTT reagent (100 μL) was carried out at 37° C. for exactly 3 minutes prior to initiation by addition of calcium (100 μL of 25 mM $CaCl_2$).

4. Preparation of corn trypsin inhibitor:

For these experiments, a Hageman.factor (i.e., factor XIIa) inhibitor was purified from corn (corn trypsin inhibitor, CTI) according to the procedure of Hojima, et al., supra, with a few modifications. Dry popcorn seed (3 kg) was obtained from a local grocery, and was repeatedly extracted until no further prolongation of the aPTT in normal plasma was observed (see above procedure, "Assaying contact inhibitor activity"). This large volume of extract (approximately 6–8 L) was concentrated to a limiting volume near 400 mL in an Amicon model LP-1 concentrator fitted with an RA-2000 reservoir and S1Y3 spiral-wound cartridge. Acetone precipitation was performed as described and the resuspended material was applied to a column (2.5×60 cm) of DEAE-Sephacel, as described in Hojima, et al. supra. The major peak of inhibitory activity was pooled and applied to a second column (2.5×94 cm) of Sephadex G-50, and the final pooled fraction was concentrated using an Amicon model 8050 stirred cell concentrator (YM-5 filter, 3000 molecular weight cutoff) with four exchanges into Hepes-buffered saline (HBS; containing Hepes, 20 mM; NaCl, 150 mM;pH 7.4). The final product exhibited predominantly a single band near 12,000 molecular weight by sodium dodecylsulfate-polyacrylamide gel electrophoresis (8–18% gradient gel), and was stored at −20° C. without further purification, since isoforms of this inhibitor all exhibit similar inhibitory potential with factor XIIa. See Hojima et al. supra.

5. Factor XI preparations

Using a factor Xa amplification assay, other investigators Von dem Borne, P. A. K. (1994) *Thromb Haemost.* 72: 397 and Von dem Borne, P. A. K et al. supra have shown that traces of contaminating factor XIa in factor XI preparations (pM down to fM can significantly affect levels of the intrinsic tenase, leading to artificially high levels of factor Xa generation. Factor XI preparations were routinely treated to remove traces of factor XIa. Concentrated factor XI stocks (approximately 300–350 U/mg, ~3–5 mg/mL) were loaded into a Slide-A-Lyzer dialysis cassette (molecular weight cutoff 10,000; Pierce Chemical, Rockford, Ill.) and were treated initially with FPRck (10 μM, 30 minutes, 25° C.) in EBS. Following dialysis versus HBS (2 changes, 2 h., 4° C.), an additional treatment was performed with DFP (2 mM) for a 15 minute interval. Final dialysis was performed versus HBS (2×2 hr., 4° C.), and the factor XI stock was aliquotted into capped non-stick microcentrifuge tubes (VWR Scientific, West Chester, Pa.), quick-frozen inside the capped tubes by immersion in a dry ice/methanol bath, and stored at −70° C. aPTT clotting assays indicated that the specific activity of factor XI was unaffected by these treatments. Following FPRck and DFP treatments, analysis of residual factor XIa activity was performed using an aminonaphthalenesulfonamide derivative (Butenas, S. et al. (1997) *J Biol Chem.* and Butenas, S. et al. (1992) *Biochem.* 31: 5399) of the tripeptide D-Leu-L-Pro-L-Arg, with $k_{cat}/K_m = 7.10 \times 10^5$ $M^{-1}$ $s^{-1}$. In factor XI preparations (typically 200 nM), factor XIa concentrations were below the limits of the assay (<100 fM factor XIa activity). Therefore, at plasma concentrations of factor XI (25–30 nM), potential contamination by factor XIa was less than 12.5 fM. No clotting (>20 minutes) was observed in factor XI deficient blood when factor XI and corn trypsin inhibitor were added in the absence of TF. However, as a final precaution for the replacement experiments using a very low TF concentration (5 pM), human $\alpha_1$-protease inhibitor (0.5 mg/mL, 9.6 μM) was added to the factor XI preparations (1.5 mg/mL, 9.4 μM) Bolton-Maggs, P. H. B. et al. (1992) *Thromb Haemost.* 67: 314. The $\alpha_1$-protease inhibitor added to the blood with these factor ) XI preparations was insignificant (22 nM) relative to the level plasma inhibitor already present (~47 μM).

6. Assay for tissue factor dependence in factor XI-deficient plasma

Relipidated tissue factor reagent (see above) was rehydrated (200 μl) and diluted with HBS/calcium (2 mM) to obtain a stock reagent containing 552 pM TF and 1.10 μM PCPS. This initial stock was further diluted with PCPS (1. 10 μM) in HBS/calcium (2 mM) to obtain a set of working TF stock concentrations ranging from 17.25 to 552 pM TF at constant lipid concentration. The assay was performed according to the following protocol: Into a polystyrene tube (12×75 mm) was added 200 μL human plasma (XI-deficient, <1% XI:C; or XI-deficient with factor XI replaced at 3.5 μg/mL, 100 U/dL) and 10 μL corn trypsin inhibitor (1.15 mg/mL in HBS). After a 30 second equilibration at 37° C., 10 μL of working TF stock was added, followed immediately by addition of 10 μL 390 mM $CaCl_2$ in water. Upon addition of the calcium, a timer was started and the tube rocked in the 37° C. water bath until strands of fibrin or a solid clot could be identified, at which point the time was noted.

7. Coagulation in whole blood

The protocol employed is a modification of Rand, M. D., et al. supra performed under the supervision of one of the authors (R. F. B.) at the Clinical Research Center, Fletcher Allen Health Care (Burlington, Vt.). Clotting in freshly drawn, non-anticoagulated whole blood was carried out in 32 capped polystyrene culture tubes as described, except that two series were performed per experiment (16 tubes/series). Reagents were loaded in the following amounts: corn trypsin inhibitor (all tubes, to give 50 μg/mL blood); relipidated TF (lipid:protein=2000) in HBS with 5 mM calcium (all tubes in each series except phlebotomy control tube, to give 25 or 5 pM TF/mL blood); factor VIII or factor XI (all tubes, replacement series only, to give 1 U/mL final); equivalent volume factor VIII/XI dilution buffer (HBS, pH 7.4, all tubes, deficiency series only). No more than 45 µL reagent were loaded in each tube. The zero tube of each series was pre-treated using 1 mL inhibitor cocktail (containing 50 mM EDTA and 20 mM benzamidine-HCl in HBS, pH 7.4), and 10 µL of 10 mM FPRck (diluted in 0.01 M HCl).

Patient or normal donor blood was drawn by venipuncture under a protocol approved by the Human Studies Committee at the University of Vermont, as described Rand, M. D., et al. supra. Clotting was initiated by delivery into the reagent-loaded tubes, and with periodic quenching of the tubes with inhibitor cocktail and FPRck as described above. Two series of quenched samples were obtained following reaction progress up to 20 minutes after initiation; both reducing (1% β-mercaptoethanol) and non-reducing SDS-PAGE samples were prepared from each tube (60 µL supernatant, 190 µL 2% SDS-PAGE sample solution Rand, M. D., et al. supra heated exactly 5 minutes at 98+/−2° C.). An aliquot from each tube was filtered to remove cellular contaminants for osteonectin assays (200 µL, 0.2 µm AcroDisc, Gelman Sciences, Ann Arbor, Mich.). The remaining serum and cell pellets/clots were aliquotted to screw cap tubes, frozen and stored at −20° C. for immunoblot or immunoassay analysis.

8. Immunoassays and western analysis

Commercial ELISAs for fibrinopeptide A (FPA), thrombin-antithrombin-III (TAT) and platelet α-granule release (osteonectin) were performed according to manufacturers protocols, with corrections for sample dilution by added quench solution (1.00 mL) and hematocrit (typically 40% of the total blood volume). For analysis of factor Va, samples were separated on SDS-PAGE according to Laemmli, U.K. (1970) *Nature* 227: 680 as modified by our laboratory Rand, M. D., et al. (1996) supra. Separate gels were run for heavy chain and light chain analysis. Gels were loaded with a pre-stained molecular weight standard mixture (14–200 kDa) and dilute standards (3 samples) allowing comparison and quantitation of analyte amounts horizontally on the immunoblots. Transfer from the gel to nitrocellulose (BioRad, Hercules, Calif.) was performed for 1.5–3 hours via an SDS-free tank transfer procedure as described (Towbin H, et al. (1979) *Proc Natl Acad Sci. (USA)* 76: 4350 and Gallagher, S. et al. (1993) *Current Protocols in Molecular Biology. J. Wiley and Sons.* 10.8.1.) with subsequent immunoblot analysis according to Rand, M. D., et al.(1996) supra.

Immunoblot images on Kodak X-Omat film were scanned on a Hewlett-Packard ScanJet 4C/T. Analysis of the .TIFF files was performed on a Power Macintosh 9500/200 computer using the public domain NIH Image program (v. 1.60, Spring 1994, developed at the U.S. National Institutes of Health and available from the internet by anonymous FTP from zippy.nimh.nih.gov or on floppy disk from the National Technical Information Service, Springfield, Va., part number PB95-500195GEI). Density of the bands of interest were converted to concentrations via standard curves which were obtained by running samples of known concentrations on the same gel. From these values, concentrations relative to maximum were determined.

9. Materials

Recombinant human tissue factor and recombinant factor VIII were provided as gifts by Drs. Roger Lundblad and Shu-Len Liu (Hyland Div., Baxter Healthcare Corp., Duarte, Calif.), and human factor XI was a gift from Dr. Richard Jenny (Hematologic Technologies, Inc., Essex Junction, Vt.). Trypsin inhibitor from corn was purchased from Fluka (Ronkonkoma, N.Y.). 1-Palmitoyl-2-oleoyl phosphatidylserine (PS) and 1-palmitoyl-2-oleoyl phosphatidylcholine (PC) were purchased from either Sigma Chemical Co. (St. Louis, Mo.) or Avanti Polar Lipids, Inc. (Birmingham, Ala.). D-Phenylalanyl-L-prolyl-L-arginine chloromethyl ketone (FPRck) was obtained as a gift from Hematologic Technologies, Inc. (Essex Junction, Vt.) or purchased from Calbiochem, LaJolla, Calif.. See Kettner C, et al. (1979) *Thromb Res* 14:969, 1979. Diisopropyl fluorophosphate (DFP) was obtained from Sigma Chemical Co, diluted to working concentration (1 M) in anhydrous isopropanol, and stored at −20° C. Pooled standardized normal (FACT,-lot D12S1) and factor XI-deficient (lot GK1122-N17P1) plasmas were obtained from George King Biomedical (Overland Park, Kans.). Thromboplastin (Simplastin Excel) and aPTT (Activated partial thromboplastin time Automated APTT) reagents were purchased from Organon Teknika (Durham, N.C.). The following analytes were estimated using ELISAs kits obtained from the manufacturers: thrombin-antithrombin-III (Enzygnost TAT, Behring, Westwood, Mass.), fibrinopeptide A (Asserachrom FPA, Diagnostica Stago/American Bioproducts, Parsippany N.J.). The assay for the determination of platelet osteonectin was provided as a gift from Dr. Richard Jenny (Hematologic Technologies, Inc., Essex Junction, Vt.), and was used according to the manufacturers instructions.

A murine monoclonal antibody ($\alpha FVa_{HC}$#17, 5–10 µg/mL) which recognizes an epitope between residues 307 and 506 in the heavy chain (HC) of factor V/Va (Kalafatis, M. (1995) *J Biol Chem.* 270: 4053) was prepared according to previously published procedures Kalafatis, M. et al. (1996) *Blood* 87: 4695. The reactivity and specificity of this antibody in western analyses are similar to one described previously ($\alpha FVa_{HC}$#6) Church, W. R. et al. (1988) *J Biol Chem.* 263: 6259. A second murine monoclonal antibody, directed against the light chain of the cofactor ($\alpha FVa_{LC}$#9, 5–10 µg/mL), was prepared as described elsewhere Foster, W. B. (1983) *Blood* 61: 1060.

10. Human donors

All donors, normal and deficient, were recruited and advised according to a protocol approved by the University of Vermont Human Studies Committee. Normal individuals (age range 22–36) were selected so as to exclude donors with a personal or familial history of thrombosis/hemorrhage, or regular aspirin or drug use. All individuals exhibited values in the normal range for the PT (11.6–13.8 seconds), aPTT (27–36 seconds), fibrinogen and platelet counts (172,000–376,000 mm$^3$). Subsequent to each control experiment, factor XI levels were assayed for the normal donors (range 95–119 U/dL), falling within the accepted normal adult range (75–130 U/dL) Kitchens, C. S. (1991) *Semin Thromb Hemost.* 13: 86.

The hemophilia A donor used in these studies was a 46 year old male with severe factor VIII deficiency (VIII:C<0.5%) who exhibited a lifelong tendency toward bleeding. The propositus suffered recurrent hemarthroses in the elbows, knees and ankles, and has a limited range of motion with pain in the shoulders, elbows, and ankles; he had received no replacement therapy for two-and-one-half weeks prior to the experiment. As is common among hemophilia A patients transfused with human products, the patient had developed a CDC Class A-III HIV infection. Treatment with indinevir resulted in thrombocytopenia, which partially resolved upon discontinuation of the drug. Platelet count on the day of the experiment was 97,000 plts/mm$^3$ but has dropped since then (December 1995); there is no evidence of anti-platelet antibodies. Current medications are trimethoprim-sufamethoxazole, zidovudine, lamivudine and zalcitabine.

Three hemophilia C (factor XI-deficient) donors have been studied; results with two of these patients are described here. Patient A is a 53 year old female with no family history of bleeding. She had exhibited easy bruising as well as frequent nosebleeds, but no menorrhagia. At age 33, she had surgical correction of a deviated nasal septum because of the nosebleeds, but afterward continued to experience mild nose and gum bleeding. At age 48, she was found to have a prolonged aPTT during a pre-operative evaluation for osteoarthritis of the left hip. The patient had a PT of 12.4 seconds and prolonged aPTT (factor XI:C=2%). Factor XII, fibrinogen and platelet counts are in the normal range; there was no evidence of an inhibitor. The patient underwent successful total hip replacement after replacement with fresh frozen plasma to normalize the aPTT, and experienced no complications.

Patient B is a 49 year old male with a personal history of episodic bleeding, but no family history of hemorrhage. At age 8 he had a tonsillectomy which required an extra day of hospitalization due to excessive bleeding, and at age 10 experienced two days of oozing following a dental extraction. A fracture of the clavicle at age 25 was not accompanied by significant bleeding. Following his 38th birthday, he was evaluated for a possible bleeding disorder, which yielded a PT of 11.1 seconds, a prolonged aPTT (factor XI:C=10%), bleeding time of 4.5 minutes and levels of factors VIII, IX and XII in the normal range (90–103%, with no evidence of an inhibitor). At the time of the experiment, patient B also presented with a platelet count (I45,000/mm$^3$) slightly below the normal range (172–376,000/mm$^3$); this platelet count was observed for this individual on two separate occasions.

EXAMPLE 10

Universal Hemeostasis Management Using an Extended Plasma Prothrombin Time (xpPT) Assay The xpPT assay was developed as follows.

A. Assay Development

The time for spontaneous coagulation of recalcified citrate plasma samples with either corn trypsin inhibitor or an inhibitory antifactor XI monoclonal antibody was evaluated as shown in FIG. 8. The presence of antibody or corn trypsin inhibitor at concentrations $\geq 100$ μgm/ml produced a stable extension of the adventitious coagulation time of plasma. Subsequent studies showed the addition of corn trypsin inhibitor at 100 μgm/ml from fresh blood in citrate with subsequent plasma preparation or the defrosting of the standard 11 mM citrate plasma sample in the presence of 100 μgm/ml corn trypsin inhibitor (final concentration) provided samples of equivalent quality for further analyses.

In particular, FIG. 8 shows evaluation of the spontaneous clotting time of citrated plasma upon decalcification in the presence of various concentrations of either corn trypsin inhibitor (CTI) or antifactor XI monoclonal antibody (α-fXI). Supression of the contact pathway is observed at concentration $\geq 100$ μgm/ml of either reagent.

Figure 9:
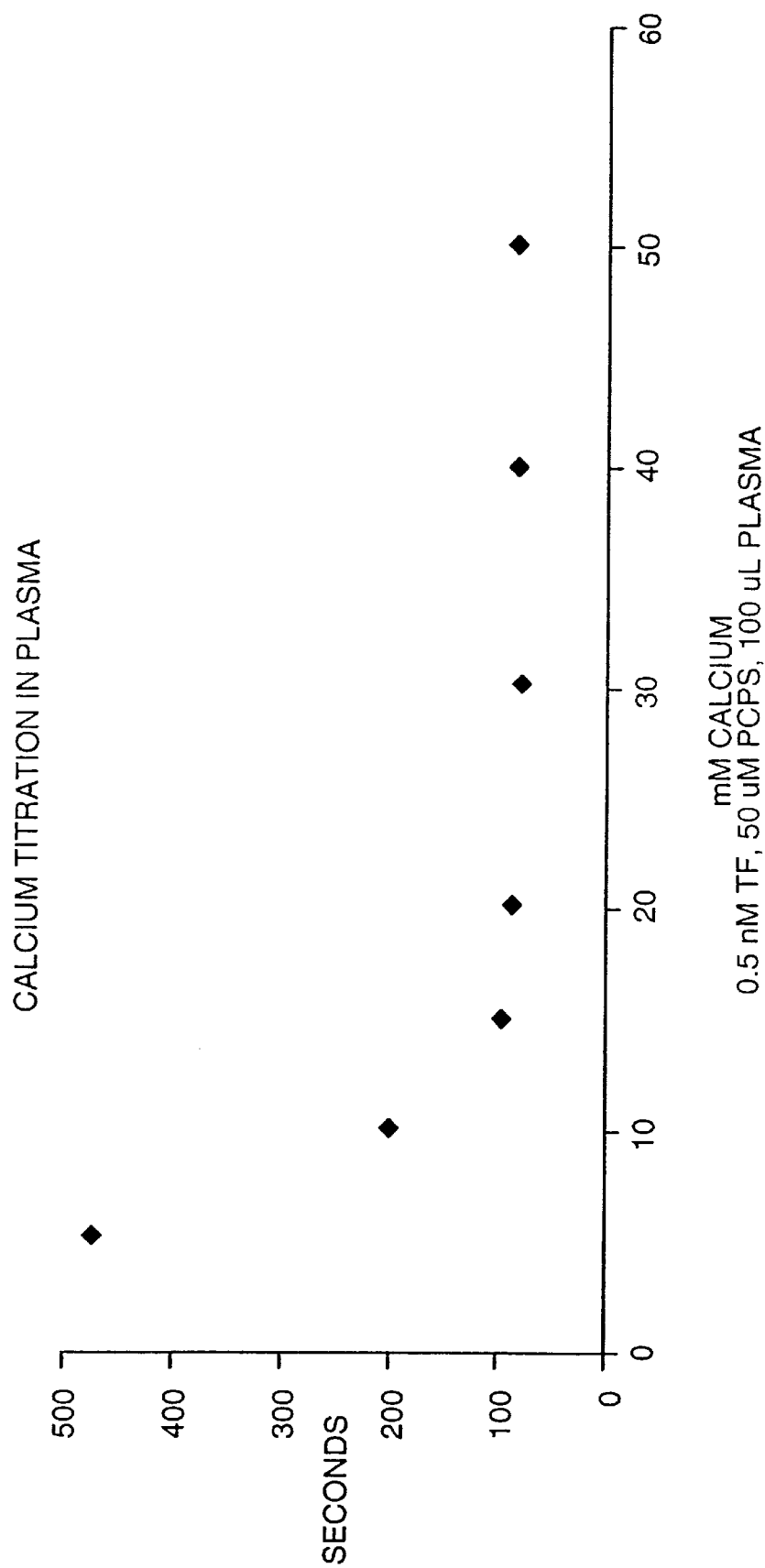
FIG. 9 is a graph showing of tissue factor (TF), phosphatidyl-choline/phsphatidyl-serine (PCPS) vesicles with calcium chloride
Figure 10:
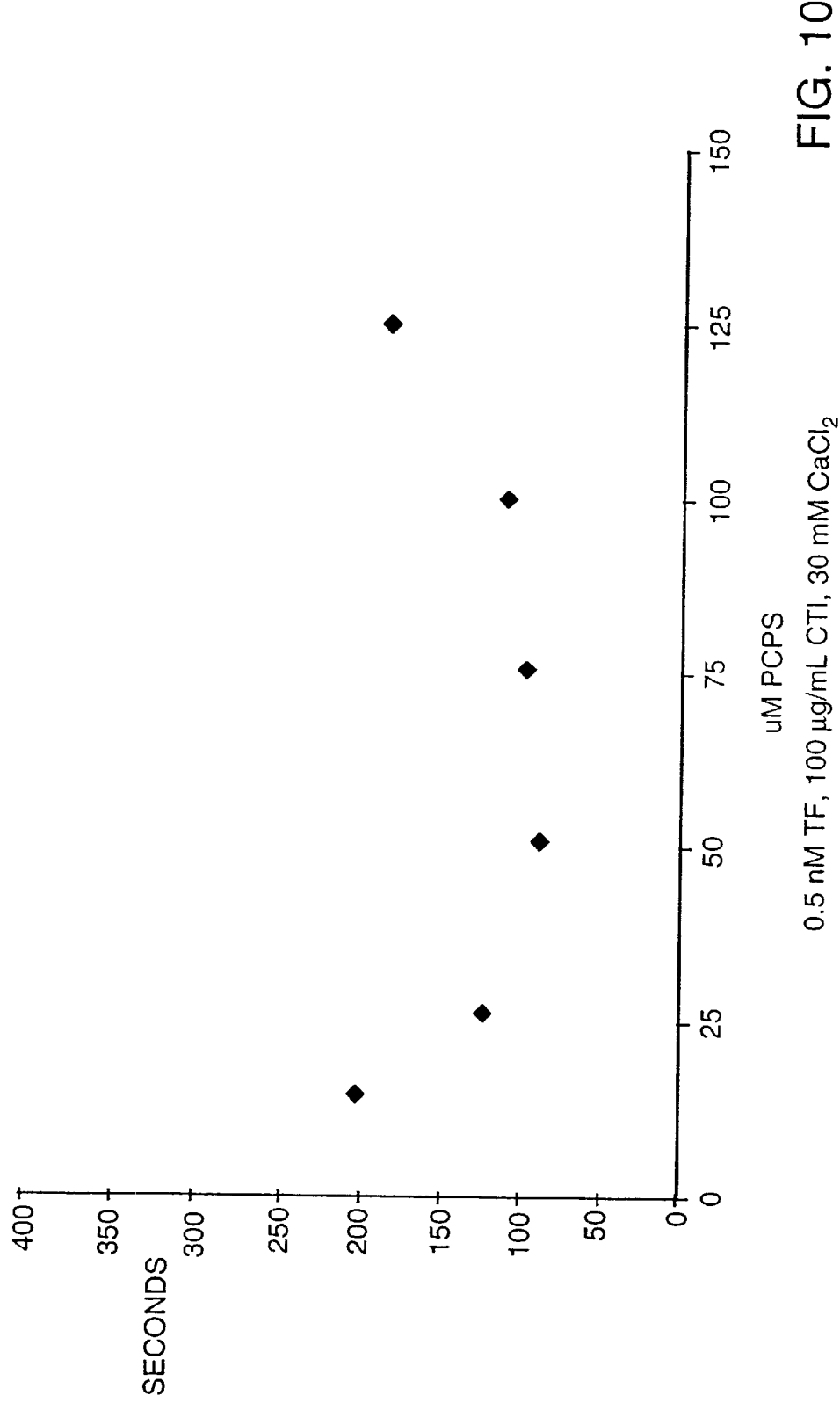
FIG. 10 is a graph showing phospholipid titration of the extended plasma prothrombin time (XpPT) assay.

Various concentrations of tissue factor, phospholipids and Ca++ were screened with the intention of developing the xpPT assay. Titration of clotting activity with increasing concentrations of phospholipid and CaCl$_2$ at 0.5 nM tissue factor are illustrated in FIGS. 9 and 10. The concentration intervals of these reagents to produce reproducible coagulation times within which a plateau is reached without sensitivity to small variations of reagents is displayed in the assay results.

The result was a standard system of coagulation evaluation in which a plasma sample collected in 11 mM trisodium citrate was frozen (standard pathology laboratory collection system) defrosted in the presence of 100 μgm/ml corn trypsin inhibitor (final concentration) and the assay ultimately conducted described in Materials and Methods section below. The final concentrations in the tissue factor clotting sample included 100 μgm/ml CTI 30 mM CaCl$_2$, 50 μM 75% PC:25PS vesicles and 0.5 nM tissue factor. This system is referred to as the XpPT assay.

FIG. 9 shows titration at 0.5 nM TF, 50 μM PCPS with CaCl$_2$ Concentrations above 20 mM are sufficient to make the assay an independent of Ca++ variable. Additionally, FIG. 10 shows phospholipid (75% PC:25% PS) titration of the XpPT. Both high and low concentrations prolong the XpPT. Concentrations between 50 and 75 μM provide reasonably stable results.

EXAMPLE 11

Using the Extended Plasma Prothrombin Time (xpPT) Assay to Monitor Coagulation

A. Sensitivity of the Assay to normal clotting

Figure 11:
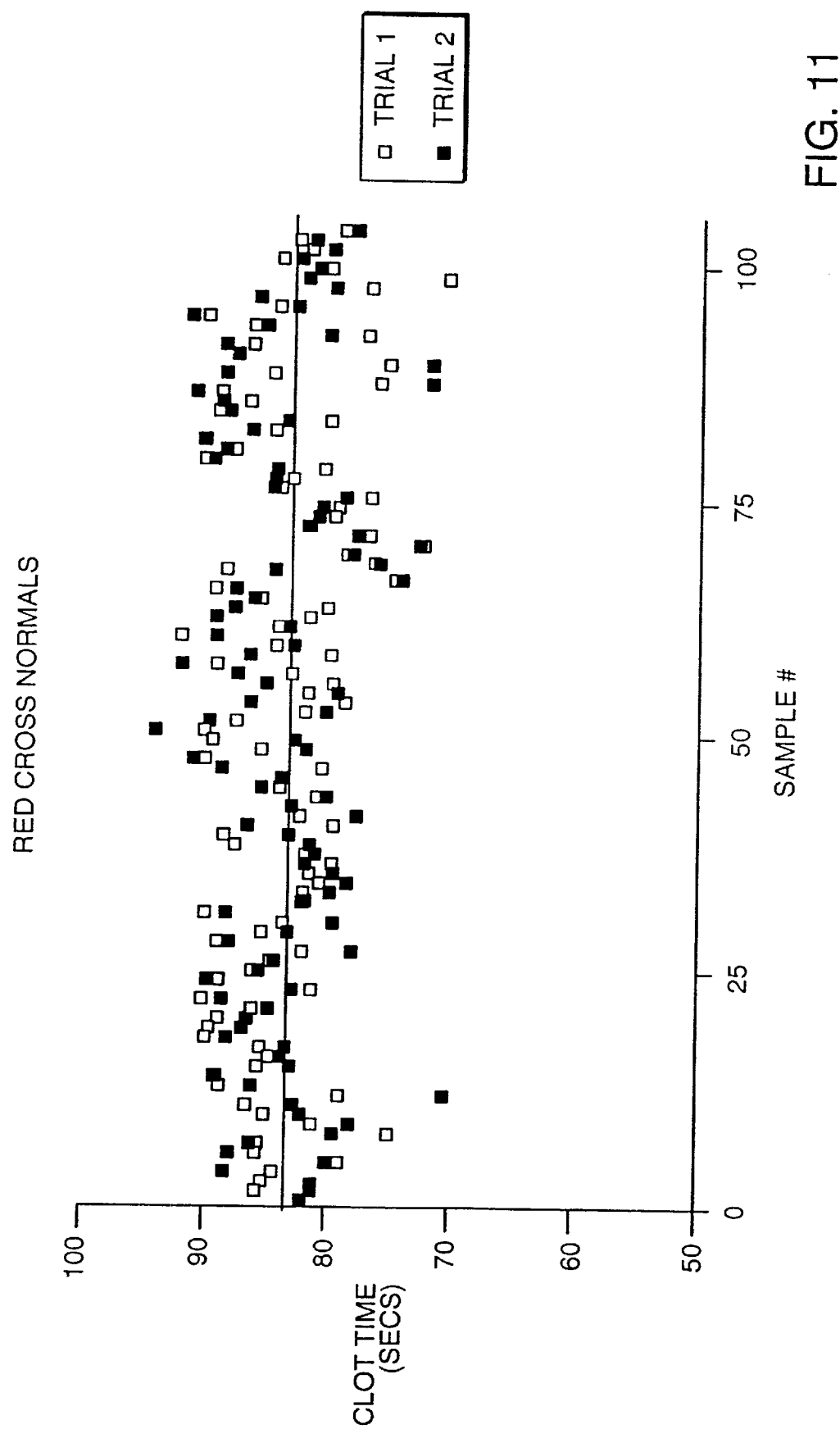
FIG. 11 is a graph showing data collection using normal plasma from volunteers obtained over an eight (8) month period.

A normal value study was conducted with plasma samples using plasma taken from 25 individuals who were normal Red Cross blood donors. The blood collected at four to five periods for each individual for a period of eight months. The values of the XpPT for these individuals are illustrated in FIG. 11 with analyses of the data presented in FIG. 14. With 103 assays performed the mean clotting time was 80.78 seconds with cv of a little over 3%. It is essentially noteworthy (FIGS. 12 and 13) that the within subject CVi and the between subjects CVg using this assay are almost the same, indicating that any single point measurement for any individual will be valid to compare that individual to the rest of the cohort.

Figure 12:
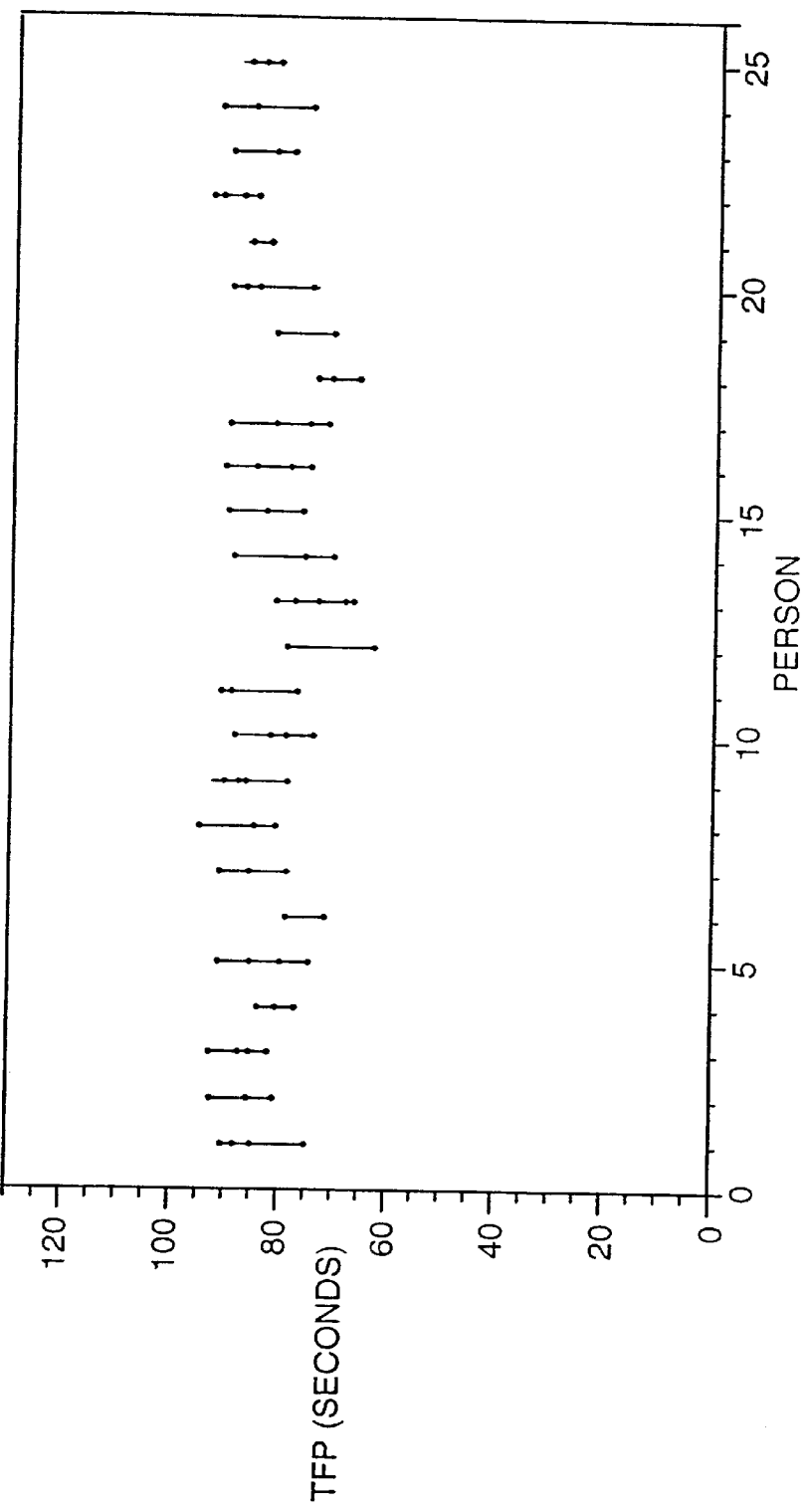
FIG. 12 is a graph showing extended plasma prothrombin time (XpPT) assay times from samples obtained from plasma donors.

In particular, FIG. 11 shows data collection using Red cross normal plasma obtained from 25 volunteers at various (4–5) intervals over an eight month period. Duplicate analyses (open and closed squares) were conducted on separate dates are presented. FIG. 12 shows XpPT times for the individual's samples obtained from twenty five plasma donors obtained at various (3–4) times.

Additionally, the table in FIG. 13 shows assay Standardization at 0.5 nM Tissue Factor in the XpPT normal value study in plasma of 25 individuals for a total of 103 plasma samples. The coefficient of variation (CVa) for the overall analysis 3.17%. The coefficient of variation across the individuals (CVi) is 5.42% while the variation from individual (CVg) to individual is 5.65%. The values are contrasted to similar variables with a recent (Hayes) cholesterol study. FIG. 14, also a table, shows coagulation time measurements in the XpPT for deficient plasmas measured with 12.5 pM and 0.5 nM tissue factor.

B. Sensitivity of the Assay to Therapeutic Agents

To study the effects of heparin, 0–3 U/mL (10,000 u/mL stock) were titrated into normal, CTI (100 μg/mL), citrated plasma. Into reaction cuvettes, 100 mL of plasma, 10 μL of 300 mM CaCl$_2$ (final, 30 mM) and 1.3 L of 3.72 mM PCPS (final concentration, 50 μM) were added. Appropriate volumes of heparin (10,000 U/mL) were added to give 0.25, 0.5, 1.0, 1.5, 2.0, and 3.0 U/mL final concentration in 100 μL plasma. The reaction was initiated by adding 10 μL of 5 nM rTF (0.5 nM final concentration).

C. Sensitivity of the Assay to Platelet Factor 4 (PF4).

To examine the effects of platelet factor 4 (PF4) on heparin treated plasma, normal patient plasma (FACT plasma, George King Biomedicals) was treated with 3 U/mL heparin and 100 µg/mL CTI. Clotting times were measured in this plasma with 0–60 U/mL heparin and 100 µg/mL CTI. Clotting times were measured in this plasma with 0–60 U/mL PF4 (3.1 mg/ml stock at 125 units/mg).

D. Sensitivity of the Assay to Tissue Factor Pathway Inhibitor (TFPI).

The assay was used along lines discussed previously except that TFPI was added (50 µg/mL stock) at 5.0, 10.0, 20.0, 60 nM final concentration and initiating with 10 µL of 5.0 nM rTF (0.5 nM).

EXAMPLE 12

Clot Time Measurement of Deficient Plasma Using the XpPT Assay

Clotting times for commercially available plasmas deficient in factors V, VII, VIII, and IX (<1.0%) were determined. Measurements were performed at 125 pM and 0.5 nM rTF. FIG. 14 displays the influence of various plasma deficiencies on the coagulation time evaluated in the XpPT. As anticipated from previous analysis of the protime, factor V, factor VII, and prothrombin deficiencies extend the XpPT however it can also be seen that factor VIII, factor IX and factor XI deficiencies also promote extension of the XpPT.

The sensitivity of the assay to factor VIII, factor IX and factor XI is dependent upon concentration of tissue factor used to initiate the assay. Under "standard assay conditions" (0.5 nM tissue factor) factor VIII and factor IX deficiency states provide greater than 100 second extensions, of the clot time observed for the pooled plasma sample used in this study. Factor XI deficiency provides only a modest extension of clotting time under all circumstances; a result consistent with observations in whole blood at the relatively high concentrations of tissue factor used.

EXAMPLE 13

Figure 15:
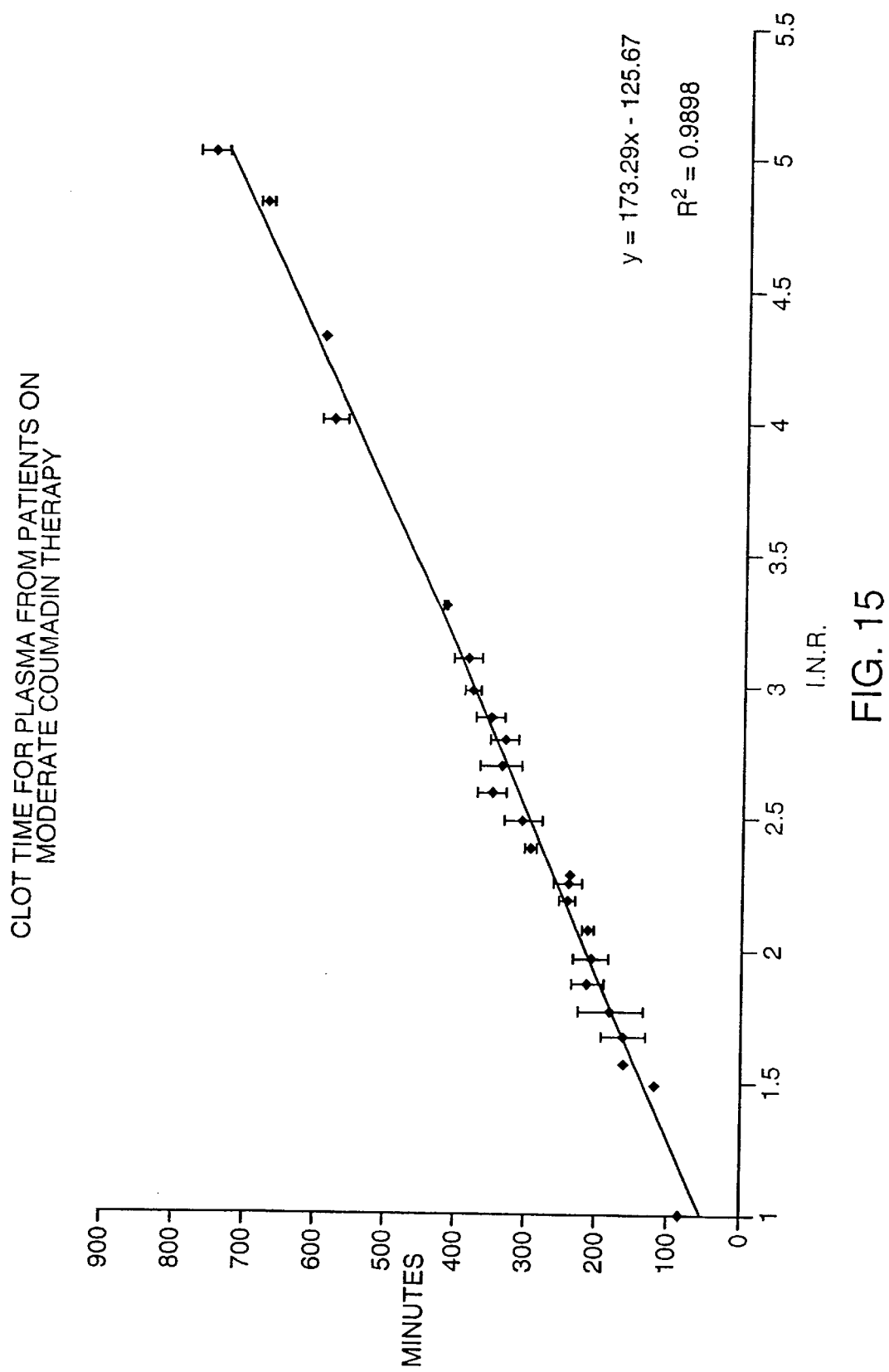
FIG. 15 is a graph showing analysis the extended plasma prothrombin time (XpPT) assay with tissue factor (TF) for individuals on warfin therapy.

Correlation of International Normalized Ratio (INR) to Clot Time Using the XpPT Assay Relationship between the assay values disclosed above in Examples 10–12 and the I.N.R. for a cohort of 150 patients on moderate Coumadin therapy was evaluated at 0.1 M tissue factor (FIG. 15). The samples used in this study were either obtained from Fletcher Allen Medical Center or from commercial sources, an almost linear dependence of clotting time on INR is observed from an INR of 1 to 5. The assay is extremely sensitive to small variations in INR with an INR of 2 producing a two minutes extension in coagulation time. Compared with normal (INR, 1.0, 82.5±0.63 [s.e.m.] seconds), patients with INR of 2.0 clot at 212.6±2.2s and patients with an INR of 4.3 clot at 610.8±4.2s.

More particularly, FIG. 15 shows an analysis of XpPT clotting time at 0.1 nM tissue factor for individuals on warfarin therapy who have been assessed to be at various INRs.

EXAMPLE 14

Standardization Of Thromboplastin Reagents Using The XpPT Assay

In contrast to the standard prothrombin time (PT) discussed above, the XpPT separates the contributions of tissue factor and phospholipids to the coagulation reaction in whole plasma. A major difficulty in the standard prothrombin time application in the clinical setting of anticoagulation is associated with the "sensitivity" of thromboplastin reagents in anticoagulant management. As a consequence of these variations, the complex and sometimes unwieldy technique of standardizing "thromboplastins" in terms of their international standardized index (ISI) which is then used to standardize the extension of coagulation time associated with anticoagulation using the international normalized ratio (INR). Since the most significant component in the variation of "thromboplastin" is associated with phospholipid content and quality and since this component is separate from the tissue factor component of the XpPT, it is possible to normalize "thromboplastins" using the XpPT,: ie to a relative ISI is one.

Figure 16:
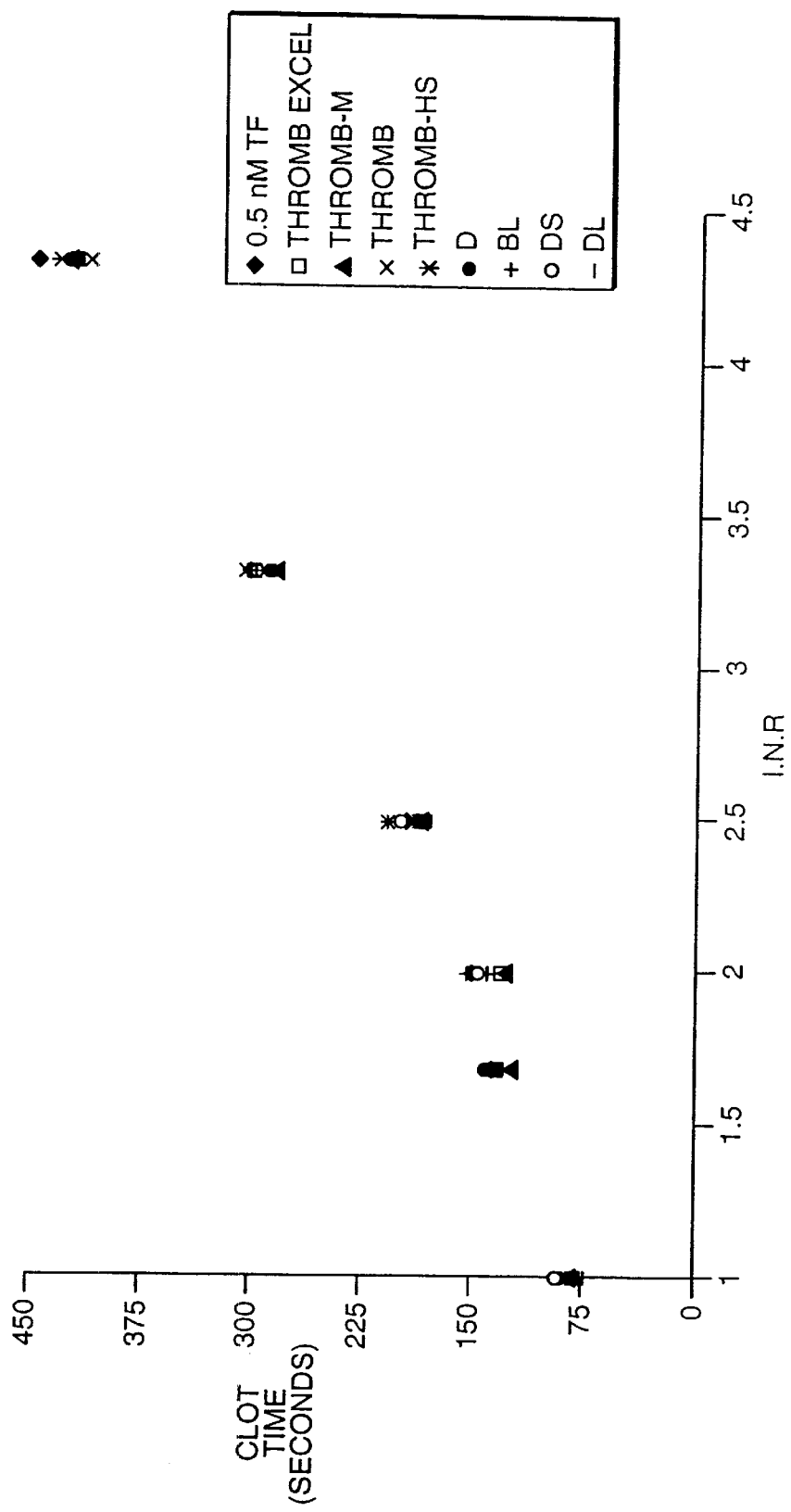
FIG. 16 is a graph showing a comparison of the the extended plasma prothrombin time (XpPT) assay clot times of various INR plasmas activated with thromboplastins from various standardized sources.

Simplastin Excel, Thromboplastin-HS, Thromboplastin-M, Thromboplastin (SIGMA), Thromboplastin-D, Bovine Lung thromboplastin (ICN), Thromboplastin-DS and Thromboplastin-DL were standardized at an INR of 1 by titration. For each thromboplastin source, the volumes used were equivalent in clot time up to an INR of 4.3 and maintained a nearly linear correlation [FIG. 16]. This figure shows a comparison of the XpPT clot times of various INR plasmas activated with thromboplastins from various sources standardized at INR=1.

EXAMPLE 15

Sensitivity of the XpPT Assay to Heparin and Tissue Factor Pathway Inhibitor (TFPI)

The sensitivity of this assay to heparin was assessed in normal patient plasma (INR,1). Heparin was added to plasma after re-calcification in concentrations from 0 to 3 U/mL. A dose dependent prolongation of clot time was observed, from 82.0s to 516.8s. To study the effects of TFPI on clotting time in normal patient plasma (INR, 1), 0.5 nM TF was used. TFPI was added from 0–60 nM to plasma after re-calcification. A dose dependent prolongation of the clot time (88.0 to 549.7s) was observed.

The Examples 10–15 show how to make and use an assay for evaluating coagulation as well as product/precursor relationships in blood or a blood product such as plasma. As discussed above, the assay is robust, reproducible and it can be used to monitor nearly all common congenital bleeding disorders in mammals and especially human patients. In addition, the assay can be used to monitor effectiveness of anti-coagulant intervention including treatment with heparin, coumidin or other recognized therapuetics. Significantly, the assay is titratable with respect to I.S.I., thus leading to a universally equivalent anti-coagulant monitoring system which is independent of thromboplastin source.

The following Materials and Methods were used in Examples 10–15 above as needed:

1. Materials.
   Recombinant human tissue factor (1-242) was provided by Hyland Div., Baxter Healthcare Corp. 1-Palmitoyl-2-oleoyl phosphatidylserine (PS) and 1-palmitoyl-2-oleoyl phosphatidylcholine (PC) were purchased from either Sigma Chemical Co. (St. Louis, Mo.) or Avanti Polar Lipids, Inc. (Birmingham, Ala.). Trypsin inhibitor from corn (CTI) was prepared as previously described. Monoclonal antibodies to factor IX and XI were obtained from the Antibody facility, University of Vermont College of Medicine. Tissue Factor Pathway Inhibitor (TFPI) was a gift from Chiron Corp. Recombinant factor VIIa was purchased from Novo Nordisk. Pooled standardized normal plasma (FACT) and factor V, factor VII, factor VIII and factor IX deficient plasmas (≦1.0% of each factor) were purchased from George King Biomedicals. Plasma for normal/value studies was obtained from 25 individuals (Red Cross volunteer donors) with 4–5 blood collection over a period of 8 months. Plasma samples from patients on moderate coumadin therapy were obtained from the Department of Pathology, University of Vermont College of Medicine. All citrated plasma samples were stored at −80° C. Thromboplastin (Simplastin Excel) was purchased from Organon Teknika (Durham, N.C.). Thromboplastin-HS, Thromboplastin-M and Thromboplastin with calcium were purchased from Sigma Chemical Co. (St. Louis, Mo.). Thromboplastin-D, Thromboplastin-DS and Thromboplastin-DL were purchased from Pacific Heamostasis (Huntersville, N.C.). Bovine Lung Thromboplastin was purchased from ICN (Costa Mesa, Calif.). An ST4 clot detector (Diagnostica-Stago) was used for clot time measurements.

2. Preparation of PCPS Vesicles:

Phosphatidyl-choline (PC) [100 mg/mL] and Phophatidyl-serine [10 mg/mL] were allowed to come to room temperature. PC and PS were mixed in the appropriate ratio (75:25, respectively) in a 30 mL glass Corex tube. The solutions were dried under nitrogen while rolling the tube on its side, making a thin coat along the walls, for 20 minutes. The tube was then washed with 11 mLs of HBS, pH 7.4. The PC/PS/HBS mixture was then sonicated on and ice bath-while purging with nitrogen for 45 minutes. The PCPS mixture was then centrifuged in a Beckman L5-50 ultracentrifuge, rotor SW50.1, at 35K rpm for 30 minutes. The speed was increased to 40K rpm and continued spinning for 3 hours. The top ¾ of the supernatant was removed and assayed to determine concentration. (Barenholz and Higgins). After concentration is determined, sucrose was added to 10% v/a and the mixture was divided into 100 μL aliquots, flash frozen and lyophilized overnight. The resulting lyophils were reconstituted with 100 μL HBS, pH 7.4 prior to use.

3. Preparation of tissue factor/lipid reagent.

Recombinant tissue factor reagent (2222 nM stock) in octylglucoside was added to 40 mLs of HBS+5 mM CaCl$_2$, pH 7.4 (90 μLs) for a final concentration of 5 nM. 107.5 μLs of PCPS vesicles (3.72 mM, 3/99 preparation) was then added to the rTF/HBS for a final concentration of 10 μM. The mixture was then incubated in a 37° C. water bath for 30 minutes. After incubation was complete, 10 mLs of 40% (w/v) sucrose was added to the mixture to give a 10% (v/v) final concentration. 240 μL aliquots were flash frozen and lyophilized overnight. The resulting lyophils were stored at −20° C., these were rehydrated with 200 μL distilled water to give 5 nM rTF/10 μM PCPL) 60 minutes before each experiment.

4. Plasma Clot Time Measurements.

Citrated platelet poor plasma (PPP) from a normal pool, patient cohorts, or factor V, VII, VIII and IX deficient pools was treated with 3.7 μL of 2.72 mg/mL (100 μg/mL final concentration) corn trypsin inhibitor (CTI) prior to thawing at 37° C. The thawed plasma was spun at 16,000×g (Eppendorf model 5415-C bench top centrifuge) for 10 minutes. Clot times were done by either a manual, tilt-tube method or using a Stago ST-4 detector. (Results were equivalent with each method.) For both methods test tubes made of clear polystyrene or similar clear plastic were used.

Reaction cuvettes for the ST4 clot detector were equilibrated to 37° C. (3 minutes) in the appropriate incubation chambers. Calcium equilibration was started by adding 10 μL of 300 mM CaCl$_2$ (final, 30 mM) to 100 μL of the CTI treated citrated PPP (normal, patient or deficient) for 15 seconds followed by 1.3 μL of 3.72 mM PCPS (25:75 PC/PS) (final concentration, 50 μM) 15 seconds. The reaction was initiated by adding 10 μL of 5.0 nM rTF (final 0.5 nM TF) or 2.5 μL of 0.5 nM rTF (12.5 pM final). End point clot times were determined visually or mechanically on the ST4 using the PTT mode, no incubation, with an upper end timing limit of 999 seconds.

5. Standardization of Thromboplastin Reagents.

Standardization of several commercially available thromboplastin reagents against a pooled normal plasma (I.N.R., 1; FACT, George King Biomedicals) clot time with 0.5 nM rTF was performed by making dilutions of the reagents in water and using volumes that provided a clot time identical with the rTF reagent in the FACT plasma. Volumes from a 1:10 dilution of each stock were used. To assay the plasmas from patients on moderate coumadin therapy, 6 μL of thromboplastin "Excel", 3 μL of thromboplastin, 3 μL of "Thromboplastin-HS", and 4 L of Sigma thromboplastin, 6 μL of Pacific Hemostas thromboplastin-D, 6 μL of ICN Bovine Lung thromboplastin, 7 μL of Pacific Hemostas thromboplastin-DS and 2 μL of thromboplastin-DL were used in lieu of the rTF tock; otherwise, the assay was performed as described above.

EXAMPLE 16

Inhibition of the Contact Pathway in Whole Blood

Optimal use of modem antiplatelet and antithrombotic drugs requires improved methods for assessment of therapeutic efficacy. Accordingly, the following assay was developed as follows to increase sensitivity based on initiation of clotting by tissue factor in minimally altered whole blood.

Figure 17:
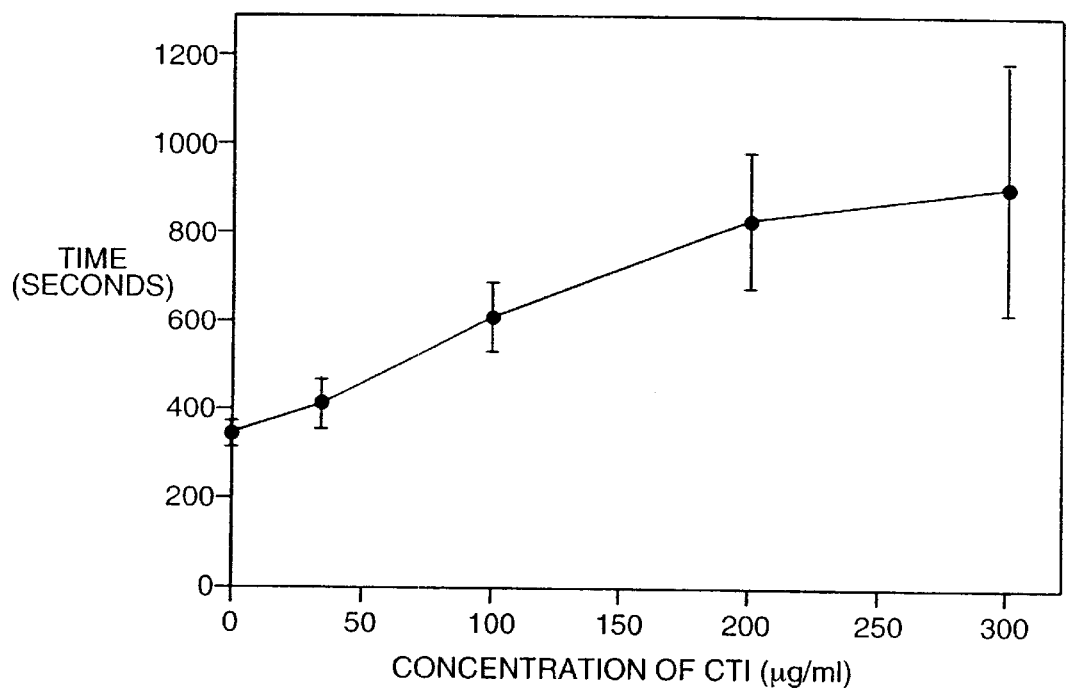
FIG. 17 is a graph showing effect of corn trypsin inhibitor (CTI) on plasma clotting time.

Corn trypsin inhibitor (CTI) was used to selectively inhibit the contact pathway of coagulation that is ordinarily inititiated when blood comes into contact with an artificial surface. Experiments to determine the effect of CTI on clotting times within the Hemochron instrument were performed in 8 subjects. For this series of experiments, no exogenous tissue factor was present. Blood without CTI clotted in 360±30 seconds. The addition of CTI led to a concentration dependent increase in the time to clot (FIG. 17). A plateau of effect was apparent with concentrations of CTI greater than 200 μg/ml. Subsequently all assays in Examples 16–19 were performed after addition of 200 μg/ml of CTI.

This assay uses an anti-coagulation sufficient amount of CTI to inhibit clotting in minimally altered whole blood. The assay is more particularly referred to herein as "tissue factor dependent clotting assay" or similar phrase. The assay is particularly useful for monitoring coagulation in whole or minimally altered whole blood. As an example, the assay is especially useful as a novel bedside tool that permits improved therapuetic assessment including standard antithrombotic and antiplatelet therapies. The assay should also facilitate improved dose selection, titration and monitoring of multicomponent antithrombotic, antiplatelet, and fibrinolytic treatment.

FIG. 17 is explained in more detail as follows. Blood was obtained by peripheral venipuncture from healthy subjects and exposed to selected concentrations of corn trypsin inhibitor (CTI). CTI is a specific inhibitor of factor XIIa without effect on other coagulation factors. Clotting was detected with an ACT instrument. Values represent means±S. D. for 8 subjects. There was a concentration dependent increase in the time to clot with CTI. Concentrations greater than 200 μg/ml did not prolong further the time to clot.

EXAMPLE 17

Initiation of Blood Coagulation with Tissue Factor

The effect of lipidated tissue factor on Hemochron-detected clotting was assessed in twelve subjects. Effects of concentrations of tissue factor ranging from 1.0 to 60 pM were evaluated. Tissue factor led to a concentration dependent decrease in the time to clot as shown in FIG. 18.

Figure 18:
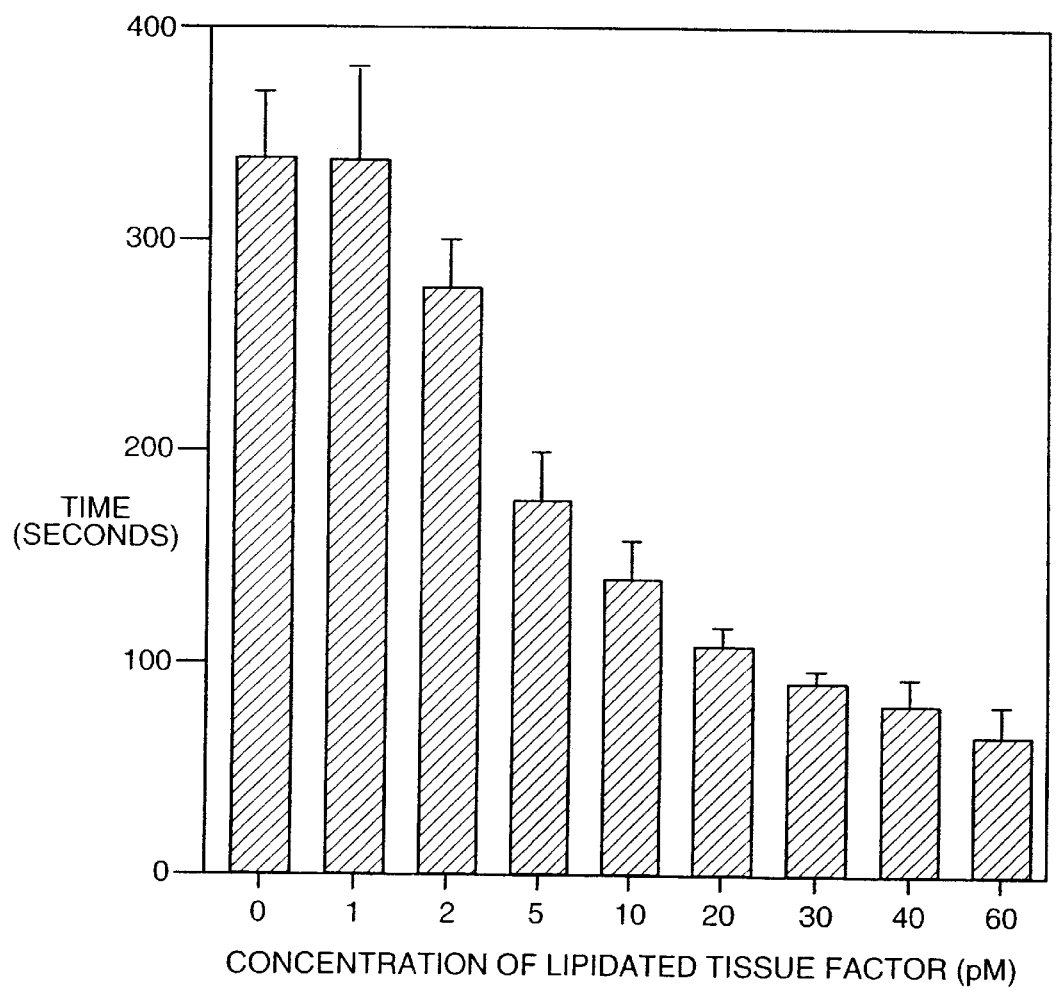
FIG. 18 is a graph showing effect of lipidated tissue factor on the clotting time.

FIG. 18 is explained as follows. Blood from healthy subjects was exposed to selected concentrations of lipidated tissue factor. Clotting was detected with an ACT instrument. Values represent means±S. D. for 12 subjects. Addition of lipidated tissue factor led to a concentration dependent decrease in time to clot.

EXAMPLE 18

Variability of the Tissue-Factor Dependent Clotting Assay

The time to clot was characterized in blood samples from twenty healthy subjects. Clotting was initiated with 10 pM tissue factor in blood pretreated with 200 μg/ml of CTI. Thus in subsequent studies, when clotting occured in less than 12 minutes, prolongation of the time to clot by antithrombotic and antiplatelet agents could be identified and attributed to inhibition of thrombin generation initiated by tissue factor rather than the contact pathway. The time to clot in samples from 4 individual subjects obtained on 3 successive days and from 20 subjects drawn and assayed on a single day are displayed in the table shown in FIG. 19. The intra-individual and inter-individual coefficients of variation were less than 10% (FIG. 19).

EXAMPLE 19

Effect of Various Agents on Clotting Time in the Tissue Factor Dependent Clotting Assay A. Hirudin Blood from 5 subjects was exposed to 0.4 and 0.8 anti-IIa U/ml of hirudin, a direct thrombin inhibitor. See FIGS. 20A and 20B. Hirudin significantly prolonged the time to clot at both concentrations tested (by 21 seconds with 0.4 U/ml and by 37 seconds with 0.8 U/ml, p<0.05 for each). The aPTT was significantly prolonged only with the higher concentration, 0.8 U/ml, of hirudin (by 16 seconds, p<0.05).

Figures 20A, 20B:
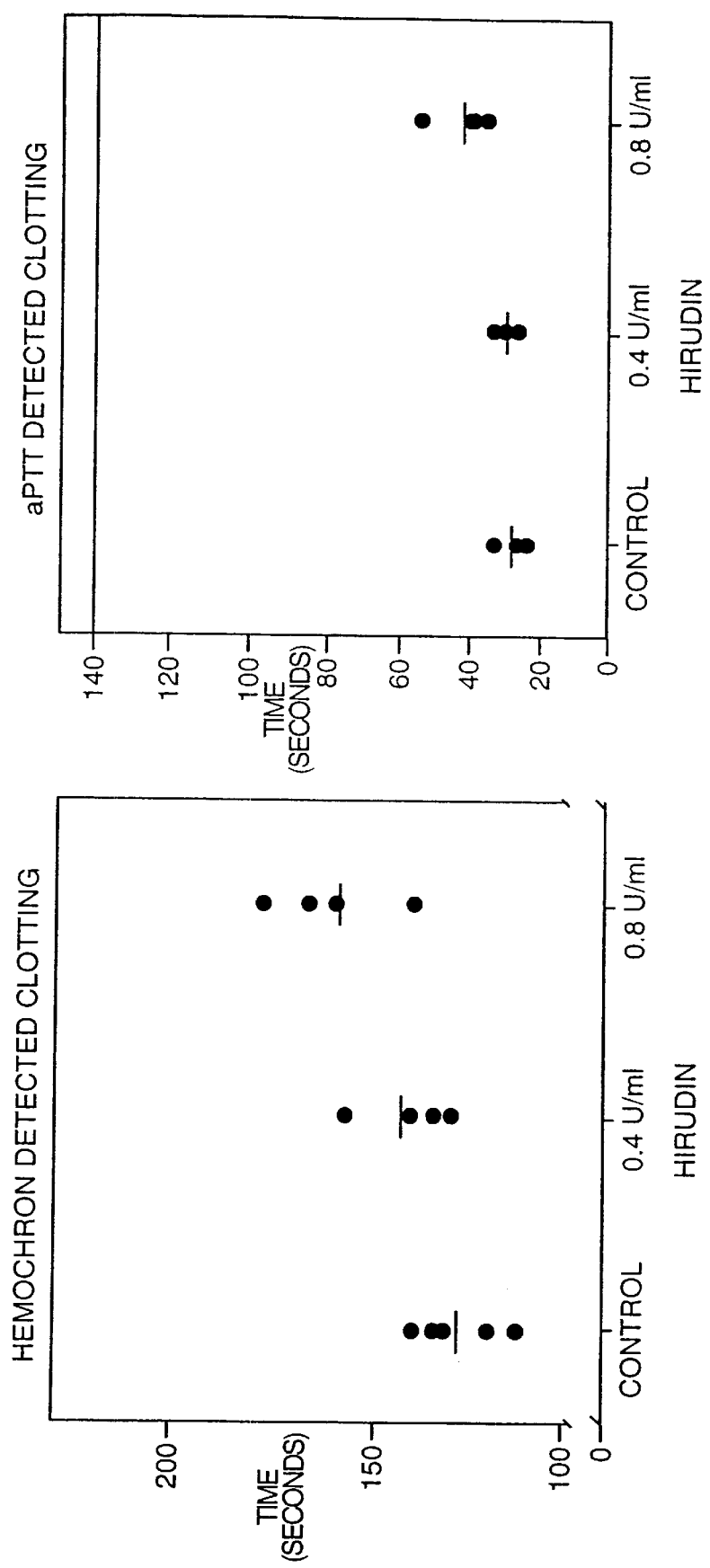
FIGS. 20A and 20B are graphs showing effect of hirudin on time to clot. Shown are hemochron-detected clotting (FIG. 20A) and aPTT detected clotting (FIG. 20B).

FIGS. 20A and 20B are explained further as follows. The effect of hirudin on the time to clot. Blood from healthy subjects was treated with 200 μg/ml of CTI and exposed also to 0.4 and 0.8 anti-IIa U/ml of hirudin. Clotting was initiated with 20 pM tissue factor and detected with an ACT instrument. Results from 5 individuals are represented by a circles. Hirudin prolonged the time to clot at each concentration tested (p<0.05). Prolongation of the aPTT was detected only with 0.8 U/ml of hirudin.

B. Recombinant tick anticoagulant (rTAP)

Blood from 8 subjects was exposed to 0.4 anti-Xa U/ml of recombinant tick anticoagulant peptide (rTAP), a specific inhibitor of factor Xa. See FIGS. 21A and 21B. rTAP significantly prolonged the time to clot (by 229 seconds, p<0.05) but had no effect on the aPTT.

Figure 21B:
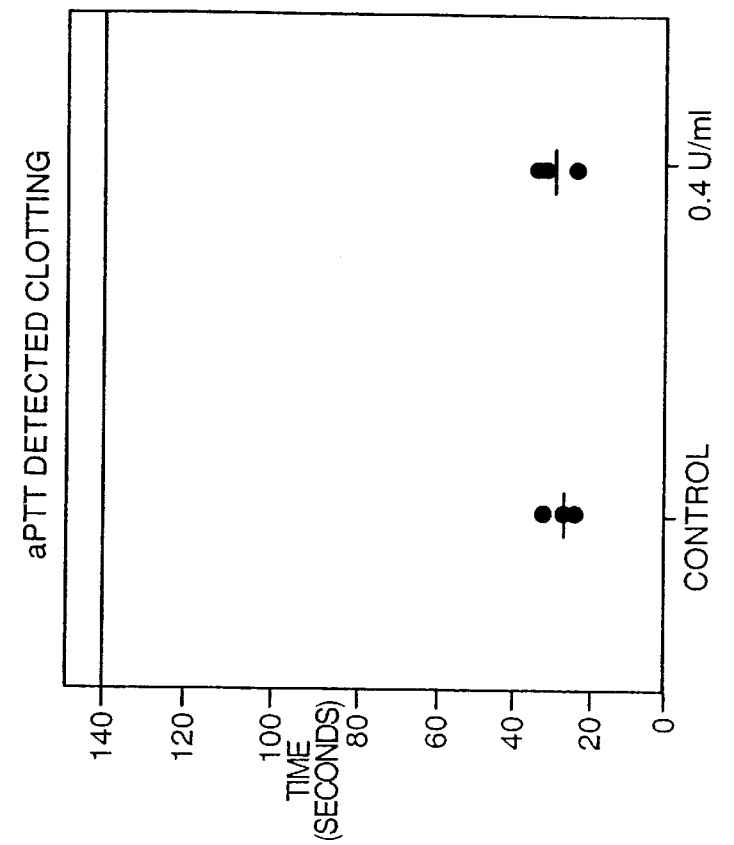
FIGS. 21A and 21B are graphs showing effect of tick anticoagulant peptide (rTAP) on clotting time. Shown are hemochron-detected clotting (FIG. 21A) and aPTT detected clotting (FIG. 21B).
Figure 21A:
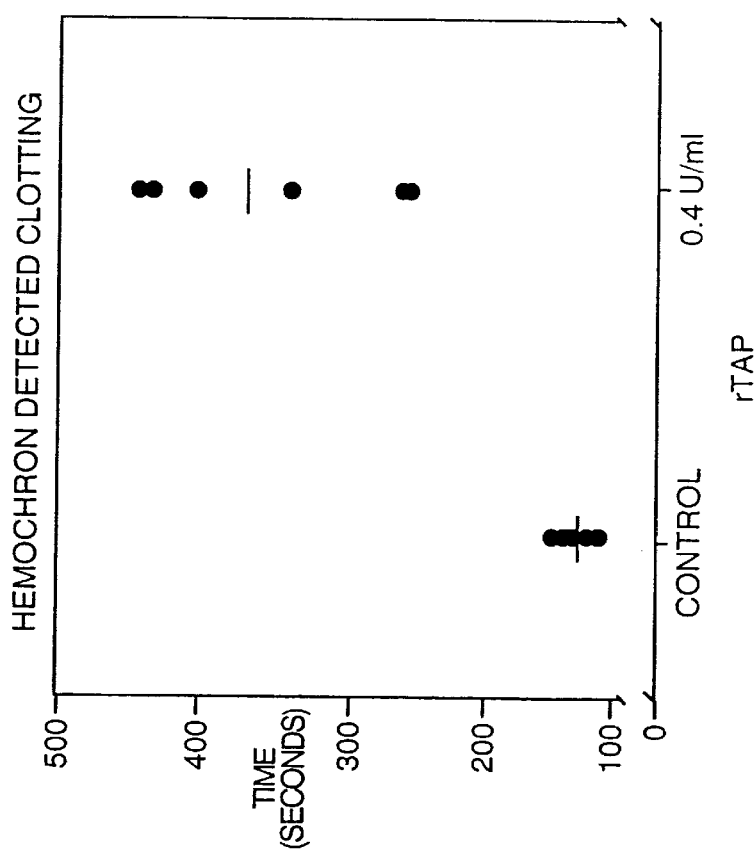

FIGS. 21A and 21B are explained in more detail as follows. The effect of tick anticoagulant peptide (rTAP) on the time to clot. Blood from healthy subjects was treated with 200 μg/ml of CTI and exposed also to 0.4 anti-Xa U/ml of rTAP. Clotting was initiated with 20 pM tissue factor and detected with an ACT instrument. Results from eight individuals are represented by circles. rTAP prolonged the time to clot p<0.05). The aPTT was not affected by rTAP.

C. Heparin

Blood from 6 healthy subjects was exposed to 0.25 and 0.4 anti-IIa/Xa U/ml of heparin. These concentrations were chosen to correspond to the range of concentrations attained in clinical practice. Both the time to clot and the aPTT were prolonged with increasing concentrations of heparin (p=0.001 for each, FIGS. 22A and 22B).

Figures 22A, 22B:
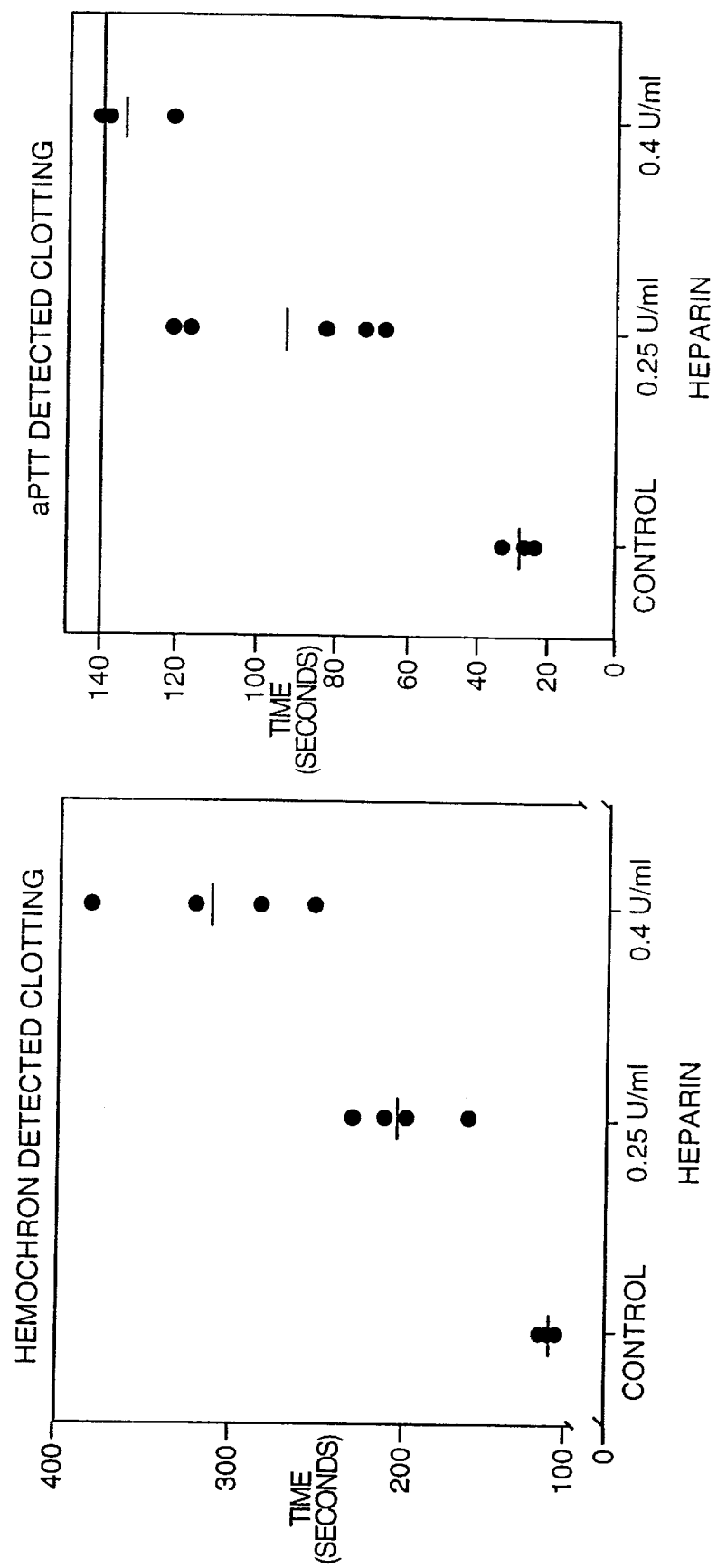
FIGS. 22A and 22B are graphs showing effect of heparin on clotting time. Shown are hemochron-detected clotting (FIG. 22A) and aPTT detected clotting (FIG. 22B)

FIGS. 22A and 22B are explained as follows. The effect of heparin on the time to clot. Blood from healthy subjects was treated with 200 μg/ml of CTI and exposed also to 0.25 and 0.4 anti-IIa U/ml of heparin. Clotting was initiated with 20 pM tissue factor and detected with an ACT instrument. Results from six individuals are represented by circles. Heparin prolonged both the time to clot and the aPTT (p=0.001 for each).

D. Enoxaparin

Blood from 5 healthy subjects was exposed to 0.4 and 0.8 anti-Xa U/ml of enoxaparin. These concentrations were chosen to correspond to those achieved in patients with acute coronary syndromes. The time to clot and the aPTT increased with increasing concentrations of enoxaparin (p=0.001 for each, FIGS. 23A and 23B).

FIGS. 23A and 23B are explained more fully as follows. The effect of enoxaparin on the time to clot. Blood from healthy subjects was treated with 200 μg/ml of CTI and exposed also to 0.4 and 0.8 anti-Xa/IIa U/ml of enoxaparin. Clotting was initiated with 20 pM tissue factor and detected with an ACT instrument. Results from five individuals are represented by circles. Enoxaparin prolonged the time to clot and the aPTT (p=0.001 for each).

E. Antibody reactive against platelet surface glycoprotein gp IIb/IIIa (abciximab) combined with heparin.

The addition of 3 μg/ml of abciximab to 0.1 anti-IIa/Xa U/ml of heparin was evaluated in blood from five healthy subjects. The addition of abciximab prolonged the time to clot further compared with that seen with heparin alone (by 62 seconds, p<0.05, FIGS. 24A and 24B). The aPTT was not affected by the addition of abciximab.

Figures 24A, 24B:
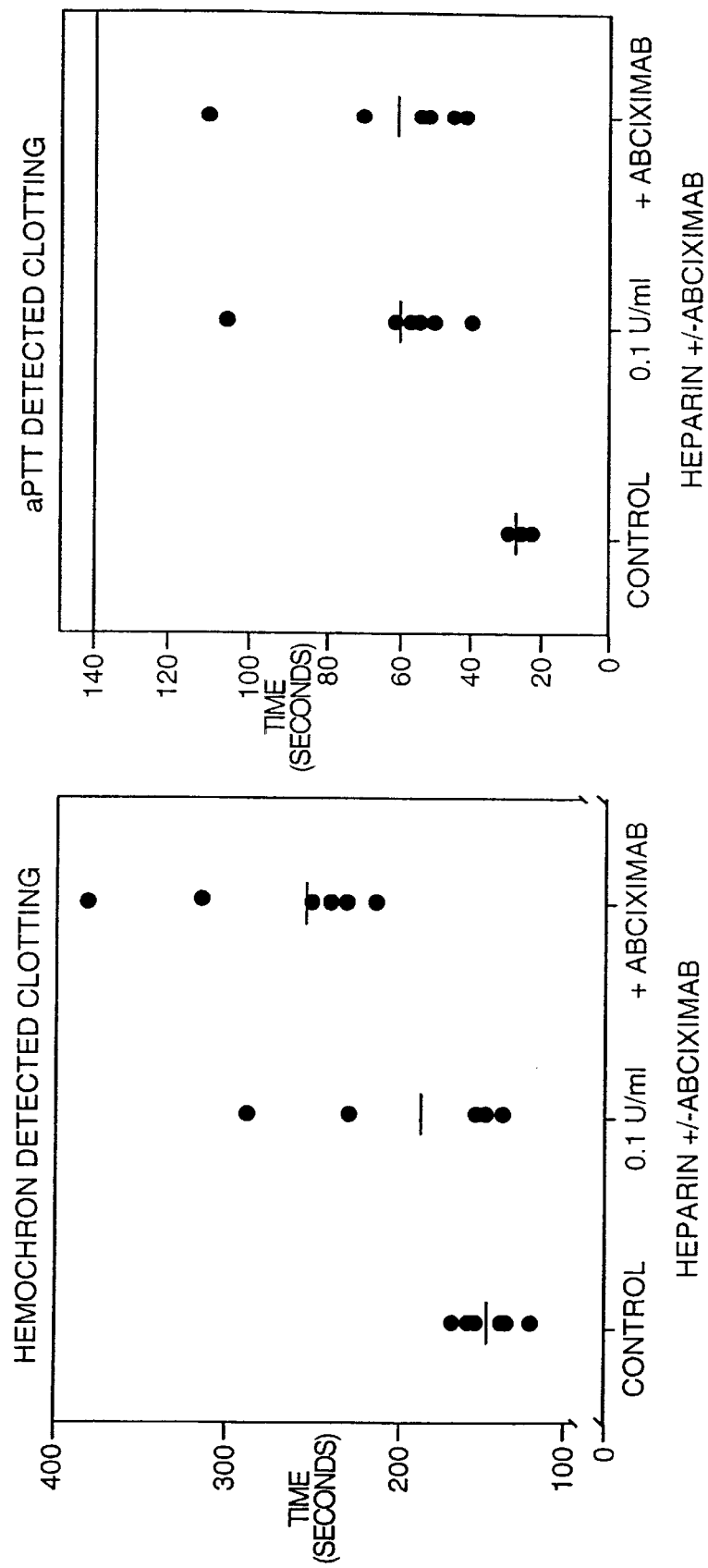
FIGS. 24A and 24B are graphs showing effect of a combination of heparin and abciximab (a commercially available monoclonal antibody against platelet glycoprotein gpII$_b$-III$_a$) on clotting time. Shown are hemochron-detected clotting (FIG. 24A) and aPTT detected clotting (FIG. 24B).
Figures 25A, 25B:
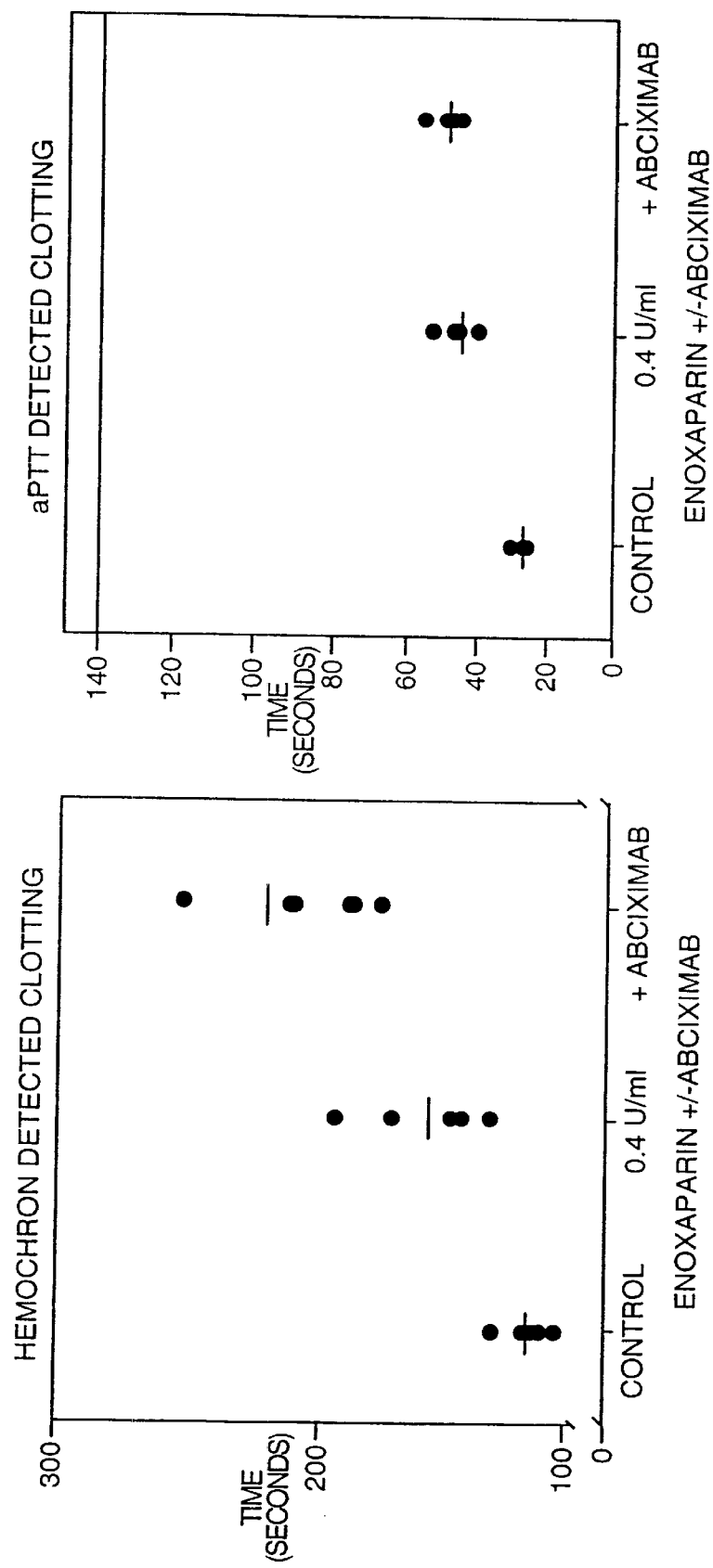
FIGS. 25A and 25B are graphs showing effect of a combination of enoxaparin and abciximab on clot time. Shown are hemochron-detected clotting (FIG. 25A) and aPTT detected clotting (FIG. 25B).

FIGS. 24A and 25B are explained in more detail as follows. The effect of the combination of heparin and abciximab on the time to clot. Blood from healthy subjects was treated with 200 μg/ml of CTI and exposed also to 0.1 anti-IIa U/ml of heparin alone and in combination with 3 μg/ml of abciximab. Clotting was initiated with 20 pM tissue factor and detected with an ACT instrument. Results from five individuals are represented by circles. The combination prolonged the time to clot compared with heparin alone (p<0.05). The addition of abciximab to heparin did not prolong further the aPTT.

F. Antibody reactive against platelet surface glycoprotein gp IIb /IIIa (abciximab) combined with enoxaparin The combination of enoxaparin (0.4 anti-Xa U/ml) and abciximab (3 µg/ml) was characterized in blood from 5 healthy subjects. The addition of abciximab to enoxaparin prolonged the time to clot further compared with that seen with enoxaparin alone (by 52 seconds, p<0.05, FIGS. 25A and 25B). The aPTT was not affected by the addition of abciximab.

FIGS. 25A and 25B are described as follows. The effect of the combination of enoxaparin and abciximab on the time to clot. Blood from healthy subjects was treated with 200 µg/ml of CTI and exposed also to 0.4 anti-Xa U/ml of enoxaparin alone and in combination with 3 µg/ml of abciximab. Clotting was initiated with 20 pM tissue factor and detected with an ACT instrument. Results from five individuals are represented by circles. The combination prolonged the time to clot compared with enoxaparin alone (p<0.05). The addition of abciximab to enoxaparin did not prolong further the aPTT.

Examples 16–19 above provide for an improved assessment of therapeutic efficacy of modern antithrombotic agents.. The assay shown features tissue factor initiated clotting in minimally altered whole blood. Results were reproducible in 20 volunteers (mean time to clot=118±9 seconds). Hirudin (0.4 anti-IIa U/ml) and tick anticoagulant peptide (0.4 anti-Xa U/ml) increased the clot time by 21 and 229 seconds, without prolonging the aPTT. The addition of abciximab (3 µg/ml) to heparin and enoxaparin further prolonged the clot time by 62 and 52 seconds. The assay should facilitate improved dose selection and monitoring of multicomponent antithrombotic, antiplatelet and fibrinolytic therapy.

In particular, experimental results were reproducible in 20 volunteers (mean time to clot=118±9 seconds). Hirudin (0.4 anti-IIa U/ml) and tick anticoagulant peptide (0.4 anti-Xa U/ml) increased the clot time by 21 and 229 seconds, without prolonging the aPTT. The addition of abciximab (3 µg/ml) to heparin and enoxaparin further prolonged the clot time by 62 and 52 seconds. As discussed, the assay should facilitate improved dose selection and monitoring of multicomponent antithrombotic, antiplatelet and fibrinolytic therapy.

The following Materials and Methods were used as needed in Examples 16–19 above.

1. Materials and Methods

Blood samples were obtained from healthy individuals and the contact pathway of coagulation was inhibited with corn trypsin inhibitor(a specific factor XIIa inhibitor without effect on other coagulation factors.). Clotting was initiated with relipidated tissue factor and detected with a Hemochron ACT instrument. Results were reproducible with samples from 20 healthy volunteers (mean time to clot=118±9 seconds). In other studies, blood was exposed to pharmacologic concentrations of antithrombotic and antiplatelet agents in vitro. Hirudin (0.4 anti-IIa U/ml) prolonged the time to clot by an average of 21 seconds (p<0.05) compared with a 3 second prolongation of the aPTT. Tick anticoagulant peptide, a direct inhibitor of factor Xa (0.4 anti-Xa U/ml), prolonged the time to clot by an average of 229 seconds (p<0.05) compared to a 3 second prolongation of the aPTT. Additive effects of antiplatelet agents were readily detectable in contrast to the case with aPTT assays. Thus, addition of 3 µg/ml abciximab to 0.1 anti-IIa/Xa U/ml of heparin and to 0.4 anti-Xa U/ml of enoxaparin prolonged the times to clot by 62 and 52 seconds, respectively (p<0.05 for each).

2. Subjects

With the use of a protocol approved by the University of Vermont Institutional Review Board, blood was obtained by peripheral venipuncture from healthy volunteers. Subjects had not ingested aspirin, nonsteroidal anti-inflammatory, or other medications for at least 10 days. All subjects provided written informed consent.

Blood was harvested between 0900 and 1200 hours. Phlebotomies were performed with 19 gauge butterfly needles and a two syringe technique with which the first three ml of blood were discarded. Blood samples were drawn into syringes containing corn trypsin inhibitor (CTI, Enzyme Research Laboratories, South Bend, Ind.) alone in concentrations ranging from 32 to 300 µg/ml or in combination with selected pharmacologic concentrations of heparin (0.1, 0.25 and 0.4 anti-IIa/Xa U/ml), enoxaparin (0.4 and 0.8 anti-Xa U/ml, Rhone-Poulenc Rorer), hirudin (0.4 and 0.8 anti-IXa U/ml, Sigma), recombinant tick anticoagulant peptide (rTAP, 0.4 anti-Xa U/ml, kindly provided by Corvass International), or abciximab (3 µg/ml, Eli Lilly). The concentrations of heparin, enoxaparin and abciximab were chosen to simulate those attained in clinical practice and equivalent anti-IIa and anti-Xa concentrations of hirudin and rTAP -were chosen. Final volumes were 1 part anticoagulant to 9 parts blood.

3. Clotting Times

A 400 µl aliquot of blood was added to a K-resin ACT tube kindly provided by International Technidyne without the glass beads traditionally used to activate the contact pathway. Lipidated tissue factor (1-60 pM, American Diagnostica, Greenwich, Conn.) was added to K-resin tubes before addition of blood.

The K-resin tubes containing tissue factor and blood were placed promptly in a Hemochron ACT instrument. The time to clot was detected by the displacement of a dependent magnet within the rotating tube when fibrin strands formed. The blood was maintained at 37° C. throughout the assay procedure.

4. Statistical Analysis

Values are means±standard deviations. Significance of differences was determined with the use of analysis of variance. Differences between treatments were assessed with the use of Student-Newman-Keuls tests. Significance was defined as p<0.05.

EXAMPLE 20

Effect of Thrombocytopenia on the Tissue Factor

The risk of spontaneous bleeding is relatively low until the platelet count drops below about 10,000 $mm^3$. The biological basis for this apparent threshold is unclear, in part because of the limitations of currently available laboratory tests. To elucidate the relationship between thrombocytopenia and coagulation, we used a model of the tissue factor pathway recently described by this laboratory [Rand M D, et al., (1996) *Blood* 88:3432]. The coagulation reaction has been examined in freshly drawn, minimally altered whole blood with varying platelet counts (5,000 –309,000/$mm^3$) from 5 normal donors and from a patient following high dose cytosine arabinoside chemotherapy. Coagulation was initiated by tissue factor (12.5 pM), contact activation suppressed by corn trypsin inhibitor, and quenched samples were collected during the course of the reaction. Analyses were performed for thrombin-antithrombin complex formation (TAT), fibrinopeptide A (FPA) and platelet degranulation (osteonectin release). Clotting was detected near the end of the initiation phase at 4.1±0.7 minutes (s.d., n=11) and was essentially unchanged for platelet counts ranging from 11,000–309,000 platelets/mm³. In contrast, all platelet counts≦11,000/ mm³, clotting was prolonged on average to 8.5±2.9 minutes (s.d., n=3); clinically the patient had petechiae at these platelet counts. The maximum rate of thrombin (TAT) generation is achieved after the initial clot is detected (i.e., during the propagation phase) and is correlated with platelet concentration in the normal and patient donors, ranging from approximately 69 nM/min at <112,000/mm³ to 128 nM/min at 289,000/mm³). However at the reduced platelet counts associated with clinical bleeding, thrombin generation occurred more slowly (17.8 nM/min at <11,000 plts/mm³ and only 4.4 nM/min at 5,000/mm³). For example, when the patient platelet count dropped to 9,000 plts/mm³, TAT generation fell to 17.6 nM/min; sixteen hours after platelet transfusion, the platelet count was 47,000/mm³ and the TAT rate had risen to 48.1 nM/min. In contrast to the TAT data, FPA release profiles correlated poorly with platelet count. Platelet degranulation assays (osteonectin release) reflected complete platelet activation within one minute of clot time for platelet counts about 112,000 platelets/mm³. At lower platelet concentrations, the data were inconclusive due to assay limitations. This study shows that prolongation of the clotting time and, in particular, impaired thrombin generation are detected by the tissue factor pathway assay when platelet counts drop to levels associated with clinical bleeding. This whole blood assay should be useful to more fully characterize the contribution of platelet number and function to coagulation.

This example shows that severe thrormbocytopenia is associated with impaired coagulation and thrombin generation in the current assay. As a result, this assay represents a convenient ex vivo test for platelet deficiency which can be performed at the point-of-care, supplanting many prior assays which are less convenient (platelet counting), prone to error (template bleeding time), or provide significant patient discomfort (template bleeding time).

Figure 26:
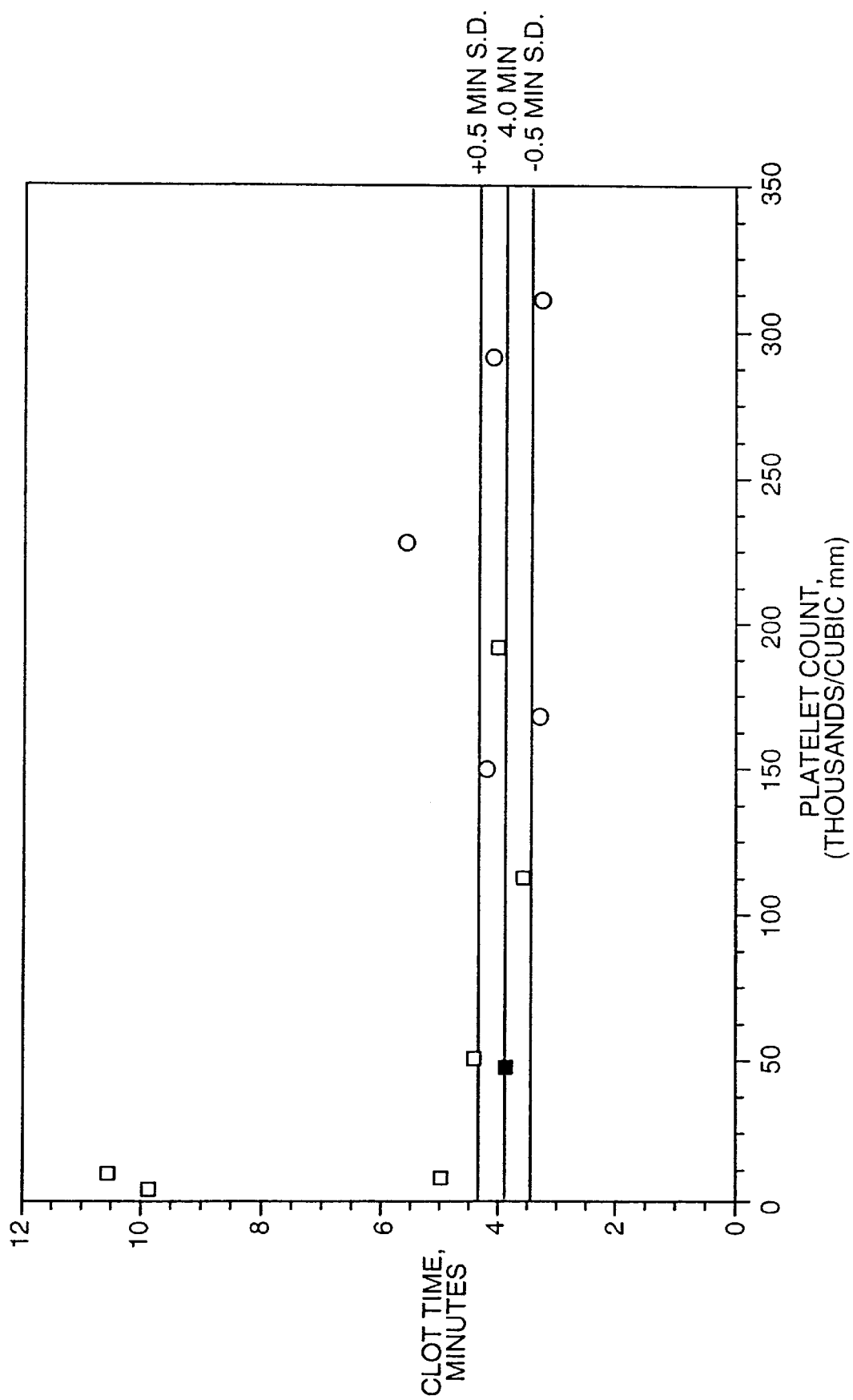
FIG. 26 is a graph showing tissue factor initiated clotting in whole blood.

FIG. 26 shows that tissue factor initiated clotting in whole blood from donors and a patient with varying levels of platelets. Twelve experiments were performed in whole blood under the conditions described in Example 7, with a few minor modifications. A tissue factor concentration of 12.5 pM was used. Blood was drawn from five normal donors with platelet levels between 148,000–309,000/mm3 (O). In addition, blood was obtained from a patient at various stages of arabinoside chemotherapy (darkened box, open box; seven experiments) exhibiting platelet counts between 5,000–193,000/mm3. In blood from the five normal donors and from the patient prior to chemotherapy, clotting occurred on average at 4.0±0.5 minutes (standard deviation). Immediately following one of the patient experiments (platelet count=9,000/mm3), a platelet transfusion was given and a follow-up experiment was performed 16 hours later (darkened box). At the very lowest platelet counts where severe thrombocytopenia is expected on the basis of platelet count (≦11,000/mm3), the clot time in the patient's blood was significantly prolonged (average of 8.5±2.9 minutes) in comparison with the normal time. Platelet transfusion adjusted the patient platelet count to 47,000/mm3, which decreased the clot time back into the normal range (limits indicated by the horizontal lines).

Figure 27:
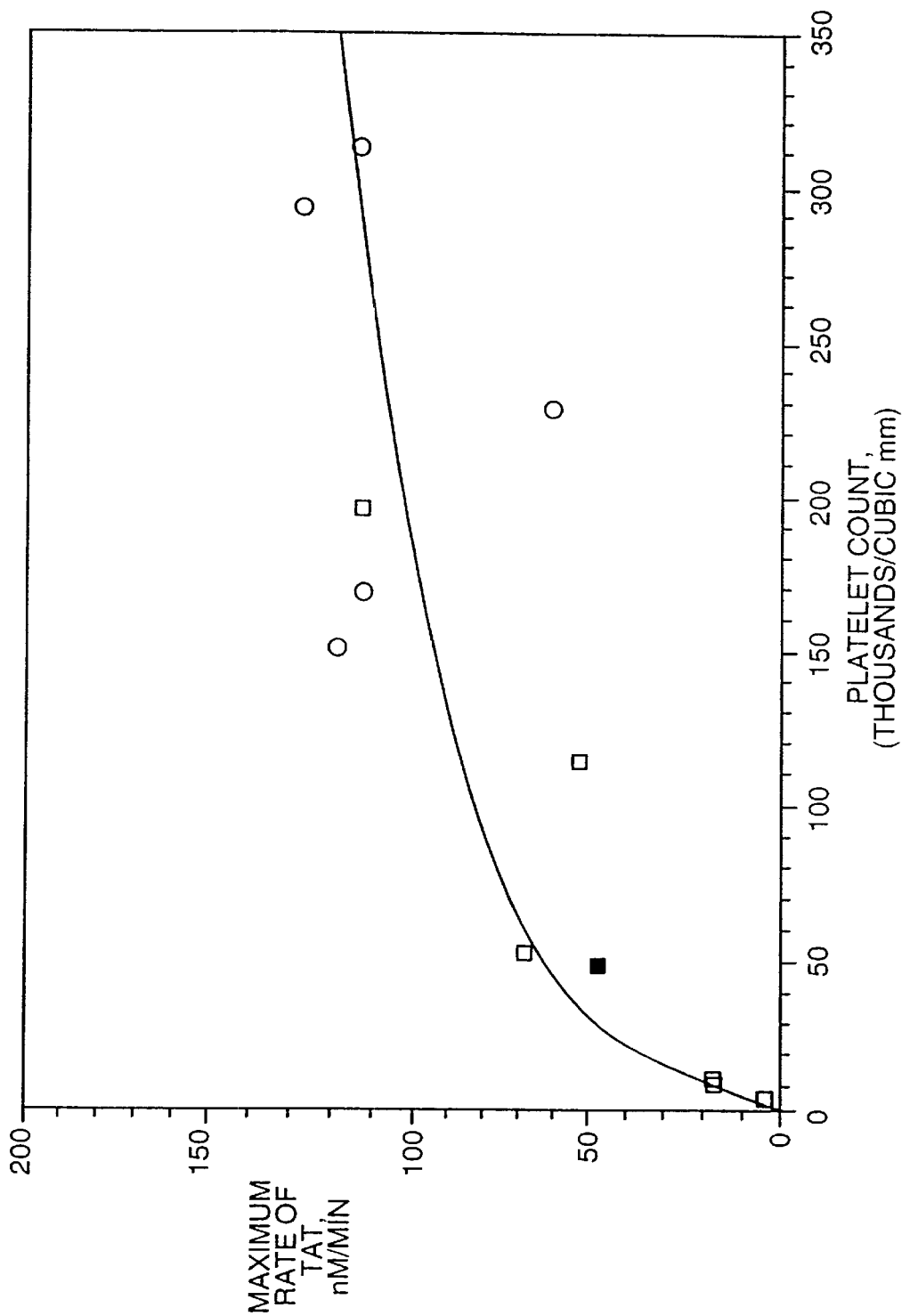
FIG. 27 is a graph showing thrombin generation during whole blood coagulation with varying platelet count.

FIG. 27 shows maximum rates of thrombin generation in the propagation phase during whole blood coagulation with varying platelet count. For each of the twelve experiments described in FIG. 26 above, the maximum rate of thrombin generation was determined using an immunoassay for thrombin-antlthrombin (TAT) complex. The resulting rates are shown as a function of platelet count. In blood from normal donors (O, platelet counts between 148,000–309,000/mm3), thrombin generation rates ranged from 69 to 128 nM/min. In the patient's blood (open box), three experiments were performed where severe thrombocytopenia was indicated by low platelet counts (≦11,000/mm3). In these three experiments, thrombin levels were below 17.8 nM/min. In one particular experiment at 9,000 platelets/mm3, and significantly increased the rate of thrombin generation to 48 nM/min, just below the observed lower limit for the normal range. A follow-up platelet transfusion (darkened box) elevated the patients to 47,000/mm3, and significantly increased the rate of thrombin generation to 48 nM/min, just below the observed lower limit for the normal range.

The following materials and methods were used as needed in this Example.

1. Preparation of corn trypsin inhibitor.

Corn trypsin inhibitor was prepared according to Hojima, et al. supra, with a few modifications. Dry popcorn seed from a local grocery was extracted in 01.1 M Tris/0.15<M NaCl (pH 8.0) until no further prolongation of the aPTT in normal plasma was observed. Acetone precipitation was performed as described, and the inhibitory fraction (67–86% cut) was resuspended and dialyzed in 0.040 M Tris-HCl, pH 7.5 and applied to a column (2.5×60 cm) of DEAE-Sephacel. The major peak of inhibitory activity was eluted with a linear salt gradient (0–1 M NaCl), pooled and applied to a second column (2.5×94 cm) of Sephadex G-50 in 0.04 M Tris-HCl, pH 7.5. This final pooled fraction was dialyzed overnight (3000 molecular weight cutoff) versus 10 mM ammonium bicarbonate, pH 7.8, then pyophilized to dryness. The isolated protein exhibited a single band at 14,000 molecular weight, and was reconstituted in HEBS (HEPES, 20 mM; NaCl, 150 mM; pH 7.4). No attempt was made to further purify the isoforms of this inhibitor, all of which exhibit similar inhibitory potential with factor Xiia.

2. Preparation of tissue factor/lipid reagent

Tissue factor 5 nM) was re-lipidated into small unilammelar vesicles. See Y. Barenholz et al. (1997) *Biochem* 16:2806. of 25 mol % PC (10 μM total lipid) in HBS plus calcium (2 mM) for 30 minutes at 37° C. See J. H. Lawson et al. (1994) *J. Biol. Chem.* 269:23357. Concentrated sucrose (60% w/v) was subsequently added to the relipidation mixture to 10% final in order to stabilize the vesicles for long-term freezer storage (up to 12 months). Aliquots of the reagent (200 μL) were stored at −20° C., which could be rehydrated 60 minutes before each experiment and used with reproducible results.

3 Human donors

Five normal donors and one patient receiving arabinoside chemotherapy were recruited and advised according to a protocol approved by the University of Vermont Human Studies Committee. See Rand M D et al. (1996) *Blood* 88:3432. The five normal individuals (age range 22–36) were selected by excluding donors with a personal or familial history of thrombosis/hemorrhage, or regular aspirin or drug use. Individuals selected as normal controls typically exhibited values in the normal range for the PT (11.6–13.8 seconds), aPTT (27–36 seconds), fibrinogen and platelet counts (172,000–376,000 mm³). On the day of the experiment, samples were drawn to determine cell count, PT, aPTT and fibrinogen.

A brief history for the patient is provided below. A 51 year old female administrative assistant developed fatigue and was found to have a pancytopenia. A bone marrow examination was considered non-diagnostic. A repeat bone marrow examination 6 months later showed myelodysplasia with 28% blasts and a normal karyotype. One month later her bone marrow examination showed 35% blasts, and she was begun on induction chemotherapy with idarubicin/cytosine arabioside. After the first course of treatment, her bone marrow contained 14% blasts. A second course of the same drugs resulted in a complete remission. Because the patient did not have a related bone marrow donor, she received 3 courses of high dose cytosine arabinoside (3 gm/m2 every 12 hours on days one, three and five). She tolerated the consolidation chemotherapy very well but required periodic transfusions of red blood cells and platelets for cytopenias. A search for an unrelated donor failed to identify a match. The patient currently is in complete remission on no medication. Her most recent blood counts showed a hemoglobin 13.0 gm, hematocrit 37.9, white count 5,120/cmm and platelet count 212,000/mm$^3$.

4. Coagulation in whole blood

The protocol employed is a modification of Rand, et al. (1996) Blood 88:3432, performed at the General Clinical Research Center, Fletcher Allen Health Care (Burlington, Vt.). Clotting in freshly drawn, non-anticoagulated whole blood was carried out in 16 capped polystyrene culture tubes as described. Reagents were loaded in the following amounts: corn trypsin inhibitor (all tubes, to give 100 µg/mL blood); relipidated TF (lipid: protein=2000) in HBS with 5 mM calcium (all tubes in each series except phlebotomy control tube, to give 12.5 pM TF/mL blood). No more than 50 µL reagent were loaded in each tube. The zero tube of each series was pre-treated using 1 mL inhibitor cocktail (containing 50 mM EDTA and 20 mM benzamidine-HCl in HBS, pH 7.4) and 10 µL of 10 mM FPRck (diluted in 0.01 M HCl).

Patient or normal donor blood was drawn by venipuncture under a protocol approved by the Human Studies Committee at the University of Vermont, as described in Rand M D et al. (1996) Blood 88:3432 Clotting was initiated by delivery into the reagent-loaded tubes, and with periodic quenching of the tubes with inhibitor cocktail and FPRck as described above. A series of quenched samples were obtained following reaction progress up to 20 minutes after initiation. An aliquot from each tube was filtered to remove cellular contaminants for osteonectin assays (200 µL, 0.2 µm AcroDisc, Gelman Sciences, Ann Arbor, Mich.). The remaining serum and cell pellets/clots were aliquotted to screw cap tubes, frozen and stored at −20° C. for immunoblot or immunoassay analysis.

5. Immunoassay analyses

The following analytes were estimated using commercial ELISA kits according to the instructions provided by the manufacturers: thrombin-antithrombin-III (Enzygnost TAT, Behring); fibrinopeptide A (Asserachrom FPA, Diagnostica Stage/American Bioproducts, New Jersey); and platelet osteonctin (a gift from Dr. Richard Jenny, Hematologic Technologies, Inc. Essex Junction, Vt.). Corrections for sample dilution by added quench solution (1.00 mL) and hematocrit (typically 40% of the total blood volume) were performed as described (ref. 7). Results were analyzed on a V max microliter plate reader (Molecular Devices, Menlo Park, Calif.) equipped with SOFTMaz ver. 2.0 software and an IBM Personal System 2 Model 30/286 PC. Additional details of the analyses have been provided previously. See Rand M D et al. (1996) Blood 88:3432; and Cawthem, K M, et al. (1998) Blood 918:4581.

At least some of the information in this example was presented at the 40$^{th}$ Annual Meeting of the American Society of Hematology, Miami, Fla. (December 1998).

EXAMPLE 21

Assay for Monitoring Relevant Coagulation Reactions in Plasma

Clinical evaluations of the coagulation of plasma have traditionally been performed by prothrombin time (PT) and activated partial thromboplastin time (aPTT) measurements. The PT is performed at high tissue factor (TF) and lipid concentrations, under conditions that lead to rapid clotting (11–15s) of recalcified citrate plasma. Due to high tissue factor concentrations, the PT assay is sensitive to deficiencies in the classical extrinsic pathway (factors, I, II, V, VII and X) and does not reflect the contributions of factors VIII, factor IX or factor XI in the coagulation reaction. The aPTT test contains lipid plus initiators of the contact pathway and is sensitive to factors I, II, V, VIII, IX, X, XI, XII, prekallikrein and high molecular weight kininogen. An assay which takes advantage of a broader range of clot times available at low TF concentrations by excluding interference due to spurious initiation by the contact pathway by using corn trypsin inhibitor (CTI) was developed. This assay permits complete establishment of calcium equilibria of citrated plasma prior to initiation. At low tissue factor concentrations ($\leq 0.5$ nM) the reaction occurs at a much slower rate than the classical PT, and is therefore sensitive to those plasma factors reflective of the physiological system. At 0.5 nM TF, 100 µg/ml CTI, 50 µM phosphatidyl serine/phosphatidyl choline (25:75, PCPS) and 30 mM CaCl$_2$ citrate, plasma clots at 82±6s. Under these conditions, the assay is sensitive to deficiencies of factor V (306s), factor VII (230s), factor VIII (189s) and factor IX (189s). Examination of the relationship between this assay and the International Normalized Ratio (INR) from a cohort of 150 individual patients on Coumadin therapy was evaluated. Compared with normal (INR, 1, 82±6s), plasma with INR of 2 clot at 211±8s while plasma with an INR of 4.3 clot at 616±9s. A nearly linear relationship between clot time and INR is observed. This assay has also been used to standardize several commercial sources of Thromboplastin reagent to be equivalent to the recombinant relipidated TF produced in our laboratory. Simplastin Excel, Thromboplastin-HS, Thromboplastin-M, Thrombosplastin (Sigma) standardized at INR of 1 were equivalent in clot time up to an INR of 4.3. The assay is sensitive to therapeutic agents including heparin (0–3 U/ml), tissue factor pathway inhibitor (TFPI) [0–60 nM], an experimental anticoagulant monoclonal factor IX antibody (0–1000 µg/ml) and various specific proprietary anticoagulants under evaluation. As illustrated by these observations, we have established a comprehensive assay has been established, applicable to a wide variety of relevant coagulation reactions.

EXAMPLE 22

A Novel Bedside, Tissue Factor-Dependent Clotting Assay

Optimal use of modem antiplatelet and antithrombotic drugs requires improved methods for assessment of therapeutic efficacy. Conventional in vitro assays of coagulation are distorted by interactions of cellular and protein constituents with glass and plastic. An assay was developed in which clotting is initiated in contact pathway-inhibited whole blood by the addition of picomolar concentrations of lipidated tissue factor and detected with a Hemochrom ACT instrument. Blood samples were obtained from 20 healthy subjects. The contact pathway was inhibited with corn trypsin inhibitor (a specific inhibitor of factor XIIa). Coagulation was initiated by addition of tissue factor (10 pM). The time to clot was 118 9 (S.D.) seconds. Blood was exposed in vitro to selected concentrations of hirudin (0.4 anti-IIa U/ml), recombinant tick anticoagulant peptide (rTAP, 0.4 anti-Xa U/ml) heparin (0.1 anti-IIa/Xa U/ml) and enoxaparin (0.4 anti-Xa U/ml) which increased the time to clot by 21, 229, 41, and 46 seconds, respectively (p<0.05 for each). By comparison, the aPTT was increased 34 and 15 seconds by heparin and enoxaparin, respectively, but not affected by hirudin or rTAP. The combination of abcixirmab (3 $\mu$g/ml) and heparin prolonged the time to clot by 102 seconds (a 61 second increment over that with heparin alone, p<0.05). Similarly, the combination of abciximab did not affect the aPTT. In contrast, the addition of abciximab did not affect the aPTT. Thus, the assay developed exhibits increased sensitivity permitting detection of additive and synergistic effects of diverse anticoagulants and antiplatelet drugs. Its use should facilitate optimal titration of therapy at point-of-care to meet the changing needs of individual patients.

All patents and publications disclosed herein are incorporated by reference.

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed is:

1. A method for inhibiting clotting of a blood product, the method comprising adding corn trypsin inhibitor (CTI) to the blood product in an amount sufficient to inhibit the clotting, wherein the blood product is platelet deficient plasma.

2. The method of claim 1, wherein clot time of the blood product is prolonged between about 10 seconds to about 3600 seconds when compared to a control without CTI.

3. The method of claim 1, wherein clot time of the blood product has an International Normalized Ratio (INR) of between about 1 to 6.5.

4. The method of claim 1, wherein the method is responsive to a concentration of Factor VIII or IX in the range of between about 0 units/ml to about 2 units/ml.

5. The method of claim 1, wherein the method includes adding the plasma to a reaction tube comprising CTI.

6. The method of claim 5, wherein the reaction tube further includes a buffered citrate salt.

7. The method of claim 1, wherein the method further comprises adding relipidated tissue factor (TF) to the plasma in an amount sufficient to provide between about 0.001 nM to 5 nM TF.

8. The method of claim 1, wherein the plasma is treated with at least one anti-coagulant prior to adding the corn trypsin inhibitor (CTI).

9. The method of claim 8, wherein the anti-coagulant is citrate and the citrate-treated plasma is recalcified before adding the CTI with a coagulation-effective amount of a calcium salt.

10. The method of claim 9, wherein the amount of corn trypsin inhibitor (CTI) is sufficient to prolong clotting time by between about 10 to about 3600 seconds when compared to a control without CTI.

11. The method of claim 10, wherein the amount of corn trypsin inhibitor (CTI) is between about 20 $\mu$g to about 500 $\mu$g per milliliter of the recalcified plasma.

12. The method of claim 1 further comprising adding an antibody to the blood product, wherein the antibody is capable of specifically binding a blood coagulation factor, and the antibody is added in an amount sufficient to inhibit clotting.

13. A method for assaying clotting in plasma, the method comprising:
a) treating blood with a solution comprising an amount of a calcium-chelating agent sufficient to inhibit clotting,
b) subjecting the blood to conditions conducive to producing plasma,
c) freezing the plasma,
d) contacting the frozen plasma with an amount of corn trypsin inhibitor (CTI) sufficient to inhibit clotting,
e) thawing the frozen plasma,
f) recalcifying the thawed plasma; and
g) assaying the clotting in the plasma.

14. A method for assaying clotting in plasma, the method comprising the steps of:
a) treating blood with a solution comprising an anticoagulation effective amount of corn trypsin inhibitor (CTI) and a calcium-chelating agent,
b) subjecting the blood to conditions conducive to producing plasma,
c) recalcifying the plasma; and
d) assaying the clotting in the recalcified plasma.

15. A method for assaying clotting in plasma, the method comprising:
a) treating blood with a solution comprising an amount of a calcium-chelating agent sufficient to inhibit clotting,
b) subjecting the blood to conditions conducive to making plasma,
c) contacting the plasma with an amount of corn trypsin inhibitor (CTI) sufficient to inhibit clotting,
d) recalcifying the plasma; and
e) assaying the recalcified plasma,
wherein step a) of the method further comprises adding corn trypsin inhibitor (CTI)to the blood.

16. A method for assaying clotting in plasma, the method comprising:
a) treating blood with a solution comprising an amount of a calcium-chelating agent sufficient to inhibit clotting,
b) subjecting the blood to conditions conducive to producing plasma,
c) freezing the plasma,
d) contacting the frozen plasma with an amount of corn trypsin inhibitor (CTI) sufficient to inhibit cloning,
e) thawing the frozen plasma,
f) recalcifying the thawed plasma; and
g) assaying the clotting in the plasma,
wherein the amount of corn trypsin inhibitor (CTI) added at step d) of the method is sufficient to prolong clotting time in excess of about 1000 seconds.

17. The method of claim 16, wherein the amount of corn trypsin inhibitor (CTI) is from between about 0.02 to about 1 mg CTI per milliliter of blood.

18. The method of claim 16, wherein step g) of the method further comprises adding to the plasma between about 1 mM and about 10 mM of a mixture of phoshotidylserine (25 mol. %) and phoshotidylcholine (75% mol. %) (PSPC) in an amount sufficient to provide from between about 0.01 $\mu$M to 500 $\mu$M of lipid in the plasma.

19. The method of claim 16, wherein step g) of the method further comprises adding to the plasma tissue factor (TF) in an amount sufficient to provide between about 0.001 to 5 nM TF in the plasma.

20. A method for assaying clotting in plasma, the method comprising the steps of:
   a) treating blood with a solution comprising an anti-coagulation effective amount of corn trypsin inhibitor (CTI) and a calcium-chelating agent,
   b) subjecting the blood to conditions conducive to producing plasma,
   c) recalcifying the plasma; and
   d) assaying the clotting in the recalcified plasma,
wherein the amount of corn trypsin inhibitor (CTI) added at step a) of the method is sufficient to prolong cloning time in excess of about 10 seconds to about 3600 seconds.

21. The method of claim 20, wherein the amount of corn trypsin inhibitor (CTI) is from between about 0.02 to 1 mg CTI per milliliter of blood.

22. The method of claim 20, wherein the method further comprises adding tissue factor to the blood after the CTI in step a) and step d) of the method further comprises adding to the plasma between about 500 to about 2000 mole excess of phoshphotidylserine (25 mol. %) and phosphatidyicholine (75 mol. %) when compared to the amount of tissue factor added in step a).

23. The method of claim 20, wherein step d) of the method further comprises adding tissue factor (TF) to the plasma in an amount sufficient to provide between about 0.001 to 5 nM TF in the plasma.

24. A method for monitoring blood coagulation, the method comprising contacting a blood sample with an amount of corn trypsin inhibitor (CTI) sufficient to reduce or eliminate blood coagulation; and monitoring the coagulation of the blood sample, wherein the blood sample is plasma contacted with lipidated tissue factor, an anti-thrombotic agent, or an anti-platelet agent, and further wherein the monitoring comprises measuring coagulation.

25. The method of claim 24, wherein the anti-thrombotic or anti-platelet agent is one of hirudin, recombinant tick anti-coagulant, enoxaparin, or abciximab.

26. A method for monitoring blood coagulation, the method comprising contacting a blood sample with an amount of corn trypsin inhibitor (CTI) sufficient to reduce or eliminate blood coagulation; and monitoring the coagulation of the blood sample, wherein the blood sample is plasma, wherein the method further comprises adding to the plasma an antibody capable of specifically binding a blood coagulation factor, and wherein the antibody is added to the plasma in an amount sufficient to inhibit the coagulation.

* * * * *

UNITED STATES PATENT AND TRADEMARK OFFICE
CERTIFICATE OF CORRECTION

| | |
|---|---|
| PATENT NO. | : 6,566,140 B2 |
| DATED | : May 20, 2003 |
| INVENTOR(S) | : Kenneth G. Mann, Mathew D. Rand and Kevin M. Cawthern |

It is certified that error appears in the above-identified patent and that said Letters Patent is hereby corrected as shown below:

Column 1,
Line 12, please insert the following text:

-- STATEMENT OF GOVERNMENT SUPPORT

Funding for this invention was provided in part by the Government of the United States of America, through Grant No. HL46703, by the National Institutes of Health. The Government has certain rights in this invention. --

Signed and Sealed this

Fifth Day of April, 2005

JON W. DUDAS
*Director of the United States Patent and Trademark Office*